US006812326B2

(12) United States Patent
Sato

(10) Patent No.: US 6,812,326 B2
(45) Date of Patent: Nov. 2, 2004

(54) TREX, A NOVEL GENE OF TRAF-INTERACTING EXT GENE FAMILY AND DIAGNOSTIC AND THERAPEUTIC USES THEREOF

(75) Inventor: Taka-Aki Sato, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 145 days.

(21) Appl. No.: 09/809,920

(22) Filed: Mar. 16, 2001

(65) Prior Publication Data

US 2003/0139584 A1 Jul. 24, 2003

Related U.S. Application Data

(63) Continuation of application No. PCT/US99/21654, filed on Sep. 17, 1999, which is a continuation-in-part of application No. 09/156,191, filed on Sep. 17, 1998, now abandoned.

(51) Int. Cl.[7] .................................................. C07K 1/00
(52) U.S. Cl. ....................... 530/350; 435/325; 435/366; 435/536; 435/23.1; 435/24.5; 435/24.1
(58) Field of Search .......................... 530/350; 435/325, 435/366, 320.1, 375; 536/23.1, 24.5, 24.1, 23.5; 514/44

(56) References Cited

PUBLICATIONS

Saito et al., Biochemical and Biophysical Research Communications, vol. 243, 1998, pp. 61–66.*
Van Hul et al., Genomics, vol. 47, 1998, pp. 230–237.*
Anderson, Nature, vol. 392, Apr. 30, 1998, pp. 25–30.*
Miller et al., the FASEB Journal, vol. 9, Feb. 1995, pp. 190–196.*

SwisProt database Accession No. 043909; O00225; sequence of human EXL3 protein.*
GenEmbl database Accession No. AB011091, nucleic acid sequence of KIAA0519 mRNA.*
GenEmbl database Accession No. AF001690, nucleic acid sequence of human EXTL3 mRNA.*
Ahn, J. et al. (1995) "Cloning of the Putative Tumor Suppressor Gene for Hereditary Multiple Exostoses (EXT1)" Nat. Genet. 11: 137–143.
Anderson, W.F. (1998) "Human gene therapy," Nature 392 (Supplement): 25–30.
Branch, A.D. (1998) "A good antisense molecule is hard to find," TIBS 23: 45–50.

(List continued on next page.)

Primary Examiner—Sean McGarry
Assistant Examiner—James D. Schultz
(74) Attorney, Agent, or Firm—John P. White; Cooper & Dunham LLP

(57) ABSTRACT

This invention provides an isolated nucleic acid molecule encoding a Tumor necrosis factor Receptor-Associated Factor protein-interacting hereditary multiple extoses (TREX) protein and vectors comprising the isolated nucleic acid encoding TREX. This invention also provides a purified TREX protein and antibodies thereto. This invention further provides oligonucleotides capable of specifically hybridizing with the isolated nucleic acid molecule encoding TREX. This invention further provides an antisense oligonucleotide against a genomic DNA molecule encoding TREX. This invention further provides methods of: (1) inhibiting TREX protein interaction, (2) inhibiting overexpression of TREX protein, and (3) inhibiting growth of a tumor. This invention further provides assays for: (1) screening for compounds that inhibit TREX binding, (2) detecting predispositions to cancer comprising TREX mutations, and (3) diagnosing cancer comprising TREX mutations. Finally, this invention provides pharmaceutical compositions comprising oligonucleotides that prevent overexpression of TREX, or antibodies that inhibit binding of TREX.

12 Claims, 35 Drawing Sheets

OTHER PUBLICATIONS

Cheng, G. and Baltimore, D. (1996) "TANK, a Co–Inducer with TRAF2 of TNF– and CD40L–mediated NF–kappaB Activation," *Genes & Dev.* 10: 963–973.

Lee S.Y. et al. (1997) "TRAF–interacting Protein (TRIP): A Novel Component of the Tumor Necrosis Factor Receptor (TNFR)—and CD30–TRAF Signaling Complexes that Inhibits TRAF2–mediated NF–kappa Activation," *J. Exp. Med.* 185: 1275–1285.

Lee, S.Y. et al. (1997) "TRAF2 is Essential for JNK but Not NF–kappaB Activation and Regulates Lymphocyte Proliferation and Survival," *Immunity* 7: 703–713.

Rothe, M. et al. (1996) "I–TRAF is a Novel TRAF–Interacting Protein that Regulates TRAF–Mediated Signal Transduction," *Proc. Natl. Acad. Sci. USA* 93: 8241–8246.

Saito, et al. (1998) "Structure, Chromosomal Location, and Expression Profile of EXTR1 and EXTR2, New Members of the Multiple Exostoses Gene Family. Biochemical and Biophysical Research Communications," *Biochem Biophys. Res. Commun.* 243(1): 61–66.

Sato, T. et al. (1995) "A Novel Member of the TRAF Family of Putative Signal Transducing Proteins Binds to the Cytosolic Domain of CD40," *FEBS Letter* 358: 113–118.

Stickens, D. et al (1996) "The EXT2 Multiple Exostoses Gene Defines A Family of Putative Tumor Suppressor Genes," *Nat. Genet.* 14: 25–32.

Van Hul, et al. (1998) "Identification of a Third EXT–like Gene (EXTL3) Belonging to the EXT Gene Family," *Genomics* 47 (2): 230–237.

Wise, C.A. et al. (1997) "Identification and Localization of the Gene for EXTL, a Third Member of the Multiple Exostoses Gene Family," *Genome Research* 7: 10–16.

Yeh, W.C. et al. (1997) "Early Lethality, Functional NF–kappaB Activation, and Increases Sensitivity to TNF–Induced Cell Death in TRAF2–Deficient Mice," *Immunity* 7: 715–725.

* cited by examiner

FIG. 1A-1

```
Murine TREX    1   MTGYTMLRNGGVGNGGQTCMLRWSNRIRLTWLSFTLRFIILVFFPLIAHYYLTTLDEADEA
Human  TREX    1   MTGYTMLRNGGAGNGGQTCMLRWSNRIRLTWLSFTLFVILVFFPLIAHYYLTTLDEADEA Murine TREX   61   GKRIFGPRAGSELCEVKHVLDLCRIRESVSEELLQLEAKRQELNSETAKLNLKIEACKKS
Human  TREX   61   GKRIFGPRVGNELCEVKHVLDLCRIRESVSEELLQLEAKRQELNSEPAKLNLKHEACKKS Murine TREX  121   IENAKQDILQLKNVISQTEHSYKELMAQNQPKLSLPIRLLPEKDDAGLPPPKVTRGCRLH
Human  TREX  121   IENAKQDILQLKNVISQTEHSYKELMAQNQPKLSLPIRLLPEKDDAGLPPPKATRGCRLH Murine TREX  181   NCFDYSRCPLTSGFPVVYDSDQFAFGSYLDPLVKQAFQATVRANVYVTENARATACLYVV
Human  TREX  181   NCFDYSRCPLTSGFPVVYDSDQFVFGSYLDPLVKQAFQATARANVYVTENADIACLYVI Murine TREX  241   LVGEMQEPTVLRPADLEKQLFSLPHMRTDGHNHVIINLSRKSDTQNLLYNVSTGRH-VAQ
Human  TREX  241   LVGEMQEPVVLRPAELEKQLMSLPHMRTDGHNHVIINLSRKSDTQNLLYNVSTGRAMVAQ Murine TREX  300   STLVAAQYRAGFDLVVSPLVHAMSEPNFMEIPPQQVPVKRKYLFTFQGEKIESLRSSLQEA
Human  TREX  301   SIFYIVQIRPGFDLVVSPLVHAMSEPNFMEIPPQQVPVKRKYLFTFQGEKIESLRSSLQEA Murine TREX  360   RSFEEEMEGDPPADYDDRIIATLKAVQDSKLDQVLVEFTCKNQPKPSLPTEWALCGERED
Human  TREX  361   RSFEEEMEGDPPADYDDRIIATLKAVQDSKLDQVLVEFTCKNQPKPSLPTEWALCGERED Murine TREX  420   RLELLKLSTFALIITPGDPRLLISSGCATRLFEALEVGAVPVVLGEQVQLPYHDMLQWNE
Human  TREX  421   RLELLKLSTFALIITPGDPRLVISSGCATRLFEALEVGAVPVVLGEQVQLPYQDMLQWNE Murine TREX  480   AALVVPKPRVTEVHFLLRSLSDSDLLAMRRQGRFLWETYFSTADSIFNTVLAMIRTRIQI
Human  TREX  481   AALVVPKPRVTEVHFLLRSLSDSDLLAMRRQGRFLWETYFSTADSIFNTVLAMIRTRIQI
```

FIG. 1A-2

```
Murine TREX  540  PAAPIREEVAAEIPHRSGKAAGTDPNMADNGDLDLGPVETEPPYASPKYLRNFTLTVTDC
Human   TREX  541  PAAPIREEAAAEIPHRSGKAAGTDPNMADNGDLDLGPVETEPPYASPRYLRNFTLTVTDF Murine TREX  600  YRGWNSAPGRFHLFPHTPFDPVLPSEAKFLGSSTGFRPIGGGAGGSGKEFQAALGGNVQR
Human   TREX  601  YRSWNCAPGPFHLFPHTPFDPVLPSEAKFLGSSTGFRPIGGGAGGSGKEFQAALGGNVPR Murine TREX  660  EQFTVVMLTYEREEVLMNSLERLNGLPYLNKVVVWNSPKLPSEDLLWPDIGVPIMVVRT
Human   TREX  661  EQFTVVMLTYEREEVLMNSLERLNGLPYLNKVVVWNSPKLPSEDLLWPDIGVPIMVVRT Murine TREX  720  EKNSLNNRFLPWNEIETEAILSIDDDAHLRHDEIMFGFMVWREARDRIVGFPGRYHAWDI
Human   TREX  721  EKNSLNNRFLPWNEIETEAILSIDDDAHLRHDEIMFGFRVWREARDRIVGFPGRYHAWDI Murine TREX  780  PHQSWLYNSNYSCELSMVLTGAAFFHKYYAYLYSYVMPQAIRDMVDEYINCEDIAMNFLV
Human   TREX  781  PHQSWLYNSNYSCELSMVLTGAAFFHKYYAYLYSYVMPQAIRDMVDEYINCEDIAMNFLV Murine TREX  840  SHITRKPPIKVTSRWTFRCPGCPQALSHDDSHFERHKCINFFVKVYGYMPLLYTQFRVD
Human   TREX  841  SHITRKPPIKVTSRWTFRCPGCPQALSHDDSHFERHKCINFFVKVYGYMPLLYTQFRVD Murine TREX  900  SVLFKTRLPHDKTKCFKFI
Human   TREX  901  SVLFKTRLPHDKTKCFKFI
```

FIG. 1C

```
hTREX   414  LQGE-----REDHLALIKLSHEAIITPGDPRIIVISSQCATRLFEAIEVGAVPHVLGEQVQLRYQDMLQ
hEXT2   299  RCHK-----HQVFDYPQVLQESTEGVVL--RGARI----GQA-VLSDVLQAGCVPNVIADSYILPFSEVLD
hEXT1   311  RQDRDNTEYEKYHYREMLHNATFCIVP--RGRRI-------GSF-RFLEALQAACVPVVISNGWELPFSEVIN
hEXTL1  251  RQEQDPGPGQT-QRQETLPNATHGHVSS----IS---GHRPE-----AAS-REQALQAGIPVLSPRWELPESEVID
rib-2   317  KLSQENCSLERR-H-QLIGSSHEV---------FLPSEMFFQDPISSQLGTHIHSNSQLPQDLIE hTREX   478  WNEAALMVEKPRVTEHFLIRBLSDSDLAWTRGGRFLHTVEPTADSIFNIVIAMTRTRII
hEXT2   358  WKRATSVVPEEKMSDVYSIHQSIPQRQEEMQRAARWFNEAFQSIKAHALATEQIENDRII
hEXT1   374  WNQAAVIGDERLLLQIPSTIRQIHQDKTILIQTQIMEAVYLRQTQFLIDAVIEIQDRII
hEXTL1  313  WTKAAIVADERLPLQVLAALIQEMSPARVIFLRQTQFLLDAVFSSVEKVIHTTIEVIQDRII
rib-2   377  WRRHTYRLPFARLPEAHFIVQHFEISDHIEAHVGHLFYSTVLADRHLLARSLIAALRYKL
```

FIG. 1D

Human

Mouse

FIG. 2A  *In vivo* binding
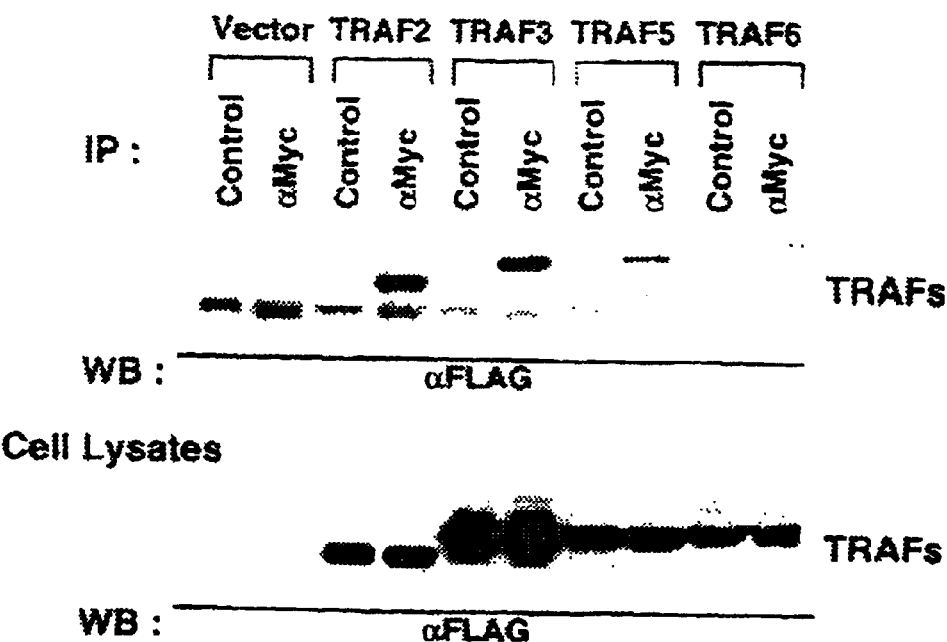
FIG. 2B
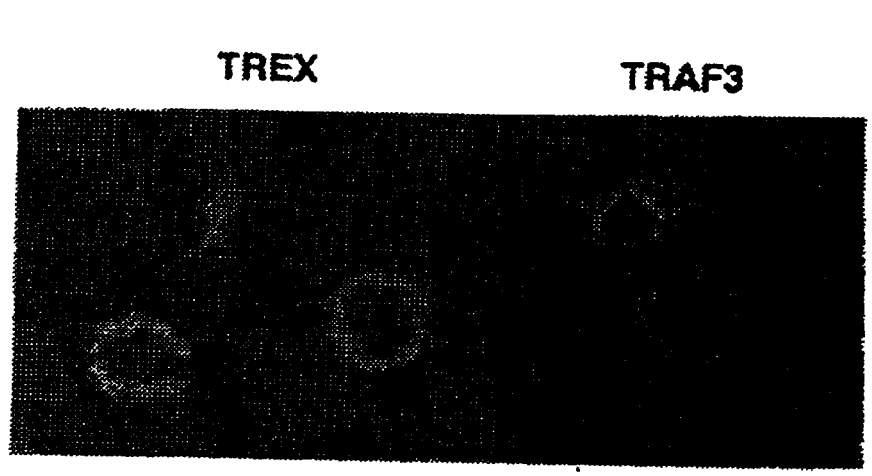

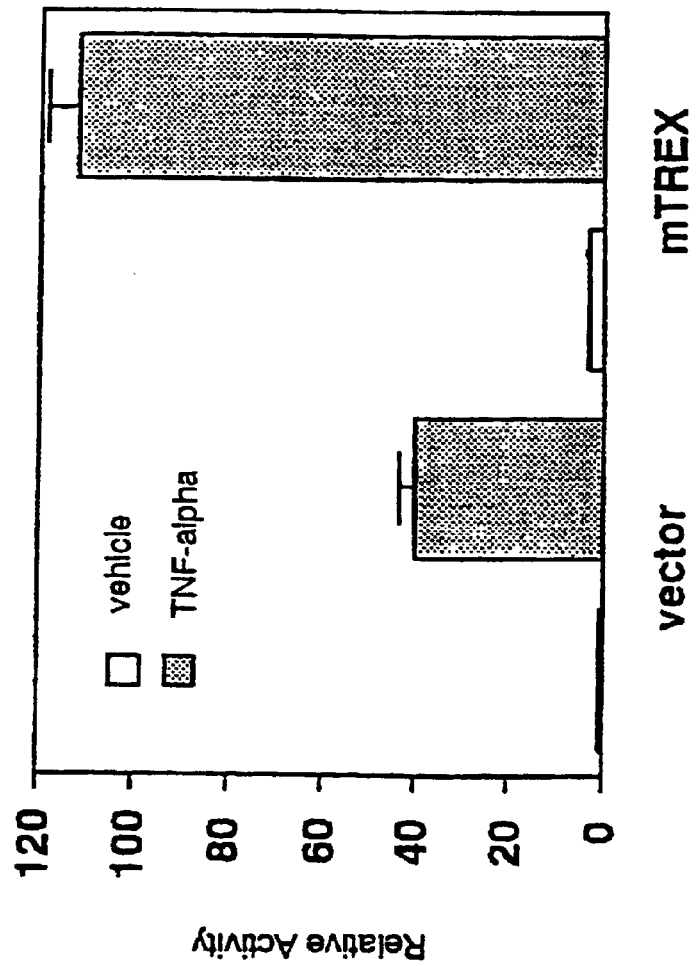

FIG. 7A-1

```
cctgatcgtt ggtagtggca tggaggacgg ggctggcatt tcagactgcc agctgttttt
accagccgct gcatcacttg aatagaagct atgcatattg gctggccgac aaagccaagg
gacaaaagct atggccgtta aaatggtccc tctgagtcca gggctctttc cctggctttt
agcaccatgg atctcttcct tttcatccca tcagcaatgt ggtaccttct tctacttgat
gatgacagct gatacttcag atttgcctga ctaaggttag aaacctgaat cgctgtgagg
aagatgaaat tccatttta cttggtgcct tgtgcaggga gcacactgat ccttccagaa
acttgtgtgt gaaaagaggt tgcgttttgt cagacagact catggttatg gcgagcgatc
cgacgtgatc agagtgggca agaggcacag cgaactcatg acaggctata ccatgttgcg
gaatggggga gtggggaacg gtggtcagac ctgtatgctg cgctggtcca atcgcatccg
gctgacatgg ctgagtttca cgctgttcat catcctcgtc ttcttccccc tcattgctca
ctattacctc accactctgg acgaggcaga cgaggctggc aagcgcatct tcggccctcg
ggctggcagt gagctctgtg aggtaaagca tgtccttgat ctctgtcgga ttcgtgagtc
tgtgagcgaa gagcttctac agctcgaagc caagcggcag gagctgaaca gcgagattgc
caagctgaac ctcaagattg aagcctgtaa gaagagcata gagaatgcca agcaggacct
gctgcagctc aagaatgtca ttagccagac agagcactcc tacaaggagc tgatggccca
gaaccagccc aaactgtccc tgcccatccg actgctccct gagaaggacg atgccggcct
tccaccccc aaggtcactc ggggttgccg ccttcacaac tgctttgatt actctcgttg
tcctctgacg tctggctttc ccgtctacgt ctatgacagt gaccagtttg cctttgggag
ctacctggac cctttggtca agcaggcttt tcaggctaca gtgagagcca acgtttatgt
tacagaaaat gcggccatcg cctgcctgta tgtggtgtta gtgggagaaa tgcaagagcc
cactgtgctg cggcctgccg accttgaaaa gcagctgttt tctctgccac actggaggac
agatgggcac aaccacgtca ttatcaacct gtcccggaag tcagacacac agaatctact
gtacaacgtc agtacaggcc gccatgtggc ccagtccacc ctctatgctg cccagtacag
agctggcttt gacctggtcg tgtcacccct tgtccatgct atgtctgaac ccaacttcat
ggaaatccca ccgcaggtgc cagttaagcg gaaatatctc ttcactttcc agggcgagaa
gatcgagtct ctgagatcta gccttcagga ggcccgttcc ttcgaggaag agatggaggg
cgaccctccg gccgactatg acgatcgcat cattgccacc ctaaaggctg tacaggacag
```

FIG. 7A-2

```
caagctggat caggtgctgg tagaattcac ttgcaaaaac cagccgaagc ctagcctgcc
gactgagtgg gcactgtgtg gggagcggga agaccgcctg gagttactga agctctccac
cttcgccctc atcatcactc ccggggaccc gcgcctgctc atttcatctg ggtgtgccac
gcggctcttc gaggccctgg aggtgggggc cgtgccggtg gtgctcgggg agcaggtgca
gctcccgtac cacgacatgc tgcagtggaa cgaggccgcc ctggtggtgc ccaagcctcg
cgtcacagag gtccacttcc tgttacgaag tctttcagac agtgatctgt tggccatgag
gcggcaaggc cgctttctct gggagaccta cttctccacc gcagacagta tttttaatac
cgtgctggcc atgattagga ctcgaattca gatccagct gctcccatcc gggaagaggt
agcggctgag atcccccatc gttcaggcaa agcagctgga actgacccca acatggctga
caatggggac ctggacctgg ggccggtaga gacagaacca ccctatgcct cacctaaata
cctccgcaat ttcactctga ctgtcacaga ctgttaccgt ggctggaact ctgcccggg
acggttccat ctttttcccc acacacctt tgatcctgtg ttgccctctg aggccaaatt
cttgggctca gggactggat ttcggccgat cggtggcggg gctgggggct ctggcaagga
gttccaggca gcgctcggag gcaatgtcca gcgggagcag ttcacagttg tgatgctgac
ctacgagcgg gaggaagtgc tcatgaactc cctggagaga ctcaacggcc tcccctacct
gaacaaggta gtggtggtgt ggaactctcc caagctgccc tcggaggacc ttttgtggcc
agacattggt gtcccatca tggtcgtccg tactgagaag aacagtttga acaatcggtt
cttgccctgg aatgagattg agacagaggc catactgtcc atcgacgatg atgctcacct
ccgccatgat gaaatcatgt ttgggttttg ggtgtggaga gaagcacgtg atcgcattgt
gggtttccct ggccggtacc atgcgtggga catcccgcac cagtcctggc tctacaattc
caactactcc tgtgagctgt ccatggtgct gacgggcgct gccttctttc acaagtatta
tgcctacctg tattcttatg tgatgcccca ggccatccgg gacatggtgg acgagtacat
caactgtgag gatatcgcca tgaacttcct tgtctcccac atcacacgga accccccat
caaggtgaca tcaaggtgga cttttcgatg cccagggtgc cctcaggccc tgtcccatga
tgactctcat tttcacgagc ggcacaagtg tatcaacttt tttgtcaagg tgtacggcta
tatgcctctc ttgtacacac agttcagggt ggactccgtg ctcttcaaga cccgcctgcc
ccatgacaag accaagtgct tcaagttcat ctagggcctt gcagttctga ggagacaatg
agcagagcga gggggagtca ccctcaaggt tcccaaggtg tcgaaggtcc ttggggacat
ctgtcgggca gggccaagac ccttttgctgg gagaggcagc aggaagagtg gaaagggata
gctgtctttc attttgaagt cagccacact gggcctggga tcctggtcag agactcaggn
cgtctgcaca gggcactgac tgatagcgaa cactgaggac tgttcataag cccaggaca
```

FIG. 7B-1

```
         10         20         30         40         50         60
cctgatcgttggtagtggcatggaggacggggctggcatttcagactgccagctgttttt 70         80         90        100        110        120
accagccgctgcatcacttgaatagaagctatgcatattggctggccgacaaagccaagg 130        140        150        160        170        180
gacaaaagctatggccgttaaaatggtccctctgagtccagggctcttTcctggctttt 190        200        210        220        230        240
agcaccatggatctcttccttttcatcccatcagcaatgtggtaccttcttctacttgat 250        260        270        280        290        300
gatgacagctgatacttcagatttgcctgactaaggttagaaacctgaatcgctgtgagg 310        320        330        340        350        360
aagatgaaatttccatttTacttggtgccttgtgcagggagcacactgatccttccagaa 370        380        390        400        410        420
acttgtgtgtgaaaagaggttgcgttttgtcagacagactcatggttatggcgagcgatc 430        440        450        460        470        480
cgacgtgatcagagtgggcaagaggcacagcgaactcatgacaggctataccatgttgcg
                                                 M  T  G  Y  T  M  L  R 490        500        510        520        530        540
gaatggggggagtggggaacggtggtcagacctgtatgctgcgctggtccaatcgcatccg
 N  G  G  V  G  N  G  G  Q  T  C  M  L  R  W  S  N  R  I  R 550        560        570        580        590        600
gctgacatggctgagtttcacgctgttcatcatcctcgtcttcttccccctcattgctca
 L  T  W  L  S  F  T  L  F  I  I  L  V  F  F  P  L  I  A  H 610        620        630        640        650        660
ctattacctcaccactctggacgaggcagacgaggctggcaagcgcatcttcggccctcg
 Y  Y  L  T  T  L  D  E  A  D  E  A  G  K  R  I  F  G  P  R 670        680        690        700        710        720
ggctggcagtgagctctgtgaggtaaagcatgtccttgatctctgtcggattcgtgagtc
 A  G  S  E  L  C  E  V  K  H  V  L  D  L  C  R  I  R  E  S
```

FIG. 7B-2

```
       730       740       750       760       770       780
tgtgagcgaagagcttctacagctcgaagccaagcggcaggagctgaacagcgagattgc
 V  S  E  E  L  L  Q  L  E  A  K  R  Q  E  L  N  S  E  I  A 790       800       810       820       830       840
caagctgaacctcaagattgaagcctgtaagaagagcatagagaatgccaagcaggacct
 K  L  N  L  K  I  E  A  C  K  K  S  I  E  N  A  K  Q  D  L 850       860       870       880       890       900
gctgcagctcaagaatgtcattagccagacagagcactcctacaaggagctgatggccca
 L  Q  L  K  N  V  I  S  Q  T  E  H  S  Y  K  E  L  M  A  Q 910       920       930       940       950       960
gaaccagcccaaactgtccctgcccatccgactgctccctgagaaggacgatgccggcct
 N  Q  P  K  L  S  L  P  I  R  L  L  P  E  K  D  D  A  G  L 970       980       990      1000      1010      1020
tccaccccccaaggtcactcggggttgccgccttcacaactgctttgattactctcgttg
 P  P  P  K  V  T  R  G  C  R  L  H  N  C  F  D  Y  S  R  C 1030      1040      1050      1060      1070      1080
tcctctgacgtctggcttccccgtctacgtctatgacagtgaccagtttgcctttgggag
 P  L  T  S  G  F  P  V  Y  V  Y  D  S  D  Q  F  A  F  G  S 1090      1100      1110      1120      1130      1140
ctacctggacccttggtcaagcaggcttttcaggctacagtgagagccaacgtttatgt
 Y  L  D  P  L  V  K  Q  A  F  Q  A  T  V  R  A  N  V  Y  V 1150      1160      1170      1180      1190      1200
tacagaaaatgcggccatcgcctgcctgtatgtggtgttagtgggagaaatgcaagagcc
 T  E  N  A  A  I  A  C  L  Y  V  V  L  V  G  E  M  Q  E  P 1210      1220      1230      1240      1250      1260
cactgtgctgcggcctgccgaccttgaaaagcagctgtttctctgccacactggaggac
 T  V  L  R  P  A  D  L  E  K  Q  L  F  S  L  P  H  W  R  T 1270      1280      1290      1300      1310      1320
agatgggcacaaccacgtcattatcaacctgtcccggaagtcagacacacagaatctact
 D  G  H  N  H  V  I  I  N  L  S  R  K  S  D  T  Q  N  L  L 1330      1340      1350      1360      1370      1380
gtacaacgtcagtacaggccgccatgtggcccagtccaccctctatgctgcccagtacag
 Y  N  V  S  T  G  R  H  V  A  Q  S  T  L  Y  A  A  Q  Y  R 1390      1400      1410      1420      1430      1440
agctggctttgacctggtcgtgtcacccccttgtccatgctatgtctgaacccaacttcat
 A  G  F  D  L  V  V  S  P  L  V  H  A  M  S  E  P  N  F  M 1450      1460      1470      1480      1490      1500
ggaaatcccaccgcaggtgccagttaagcggaaatatctcttcactttccagggcgagaa
 E  I  P  P  Q  V  P  V  K  R  K  Y  L  F  T  F  Q  G  E  K
```

FIG. 7B-3

```
         1510       1520       1530       1540       1550       1560
   gatcgagtctctgagatctagccttcaggaggcccgttccttcgaggaagagatggaggg
    I   E   S   L   R   S   S   L   Q   E   A   R   S   F   E   E   M   E   G 1570       1580       1590       1600       1610       1620
   cgaccctccggccgactatgacgatcgcatcattgccaccctaaaggctgtacaggacag
    D   P   P   A   D   Y   D   D   R   I   I   A   T   L   K   A   V   Q   D   S 1630       1640       1650       1660       1670       1680
   caagctggatcaggtgctggtagaattcacttgcaaaaaccagccgaagcctagcctgcc
    K   L   D   Q   V   L   V   E   F   T   C   K   N   Q   P   K   P   S   L   P 1690       1700       1710       1720       1730       1740
   gactgagtgggcactgtgtggggagcgggaagaccgcctggagttactgaagctctccac
    T   E   W   A   L   C   G   E   R   E   D   R   L   E   L   L   K   L   S   T 1750       1760       1770       1780       1790       1800
   cttcgccctcatcatcactcccggggacccgcgcctgctcatttcatctgggtgtgccac
    F   A   L   I   I   T   P   G   D   P   R   L   L   I   S   S   G   C   A   T 1810       1820       1830       1840       1850       1860
   gcggctcttcgaggccctggaggtgggggccgtgccggtggtgctcggggagcaggtgca
    R   L   F   E   A   L   E   V   G   A   V   P   V   V   L   G   E   Q   V   Q 1870       1880       1890       1900       1910       1920
   gctcccgtaccacgacatgctgcagtggaacgaggccgccctggtggtgcccaagcctcg
    L   P   Y   H   D   M   L   Q   W   N   E   A   A   L   V   V   P   K   P   R 1930       1940       1950       1960       1970       1980
   cgtcacagaggtccacttcctgttacgaagtctttcagacagtgatctgttggccatgag
    V   T   E   V   H   F   L   L   R   S   L   S   D   S   D   L   L   A   M   R 1990       2000       2010       2020       2030       2040
   gcggcaaggccgctttctctgggagacctacttctccaccgcagacagtatttttaatac
    R   Q   G   R   F   L   W   E   T   Y   F   S   T   A   D   S   I   F   N   T 2050       2060       2070       2080       2090       2100
   cgtgctggccatgattaggactcgaattcagatcccagctgctcccatccgggaagaggt
    V   L   A   M   I   R   T   R   I   Q   I   P   A   A   P   I   R   E   E   V 2110       2120       2130       2140       2150       2160
   agcggctgagatcccccatcgttcaggcaaagcagctggaactgaccccaacatggctga
    A   A   E   I   P   H   R   S   G   K   A   A   G   T   D   P   N   M   A   D 2170       2180       2190       2200       2210       2220
   caatggggacctggacctggggccggtagagacagaaccaccctatgcctcacctaaata
    N   G   D   L   D   L   G   P   V   E   T   E   P   P   Y   A   S   P   K   Y 2230       2240       2250       2260       2270       2280
   cctccgcaatttcactctgactgtcacagactgttaccgtggctggaactctgcccggg
    L   R   N   F   T   L   T   V   T   D   C   Y   R   G   W   N   S   A   P   G
```

FIG. 7B-4

```
         2290      2300      2310      2320      2330      2340
     acggttccatcttttccccacacacccctttgatcctgtgttgccctctgaggccaaatt
      R   F   H   L   F   P   H   T   P   F   D   P   V   L   P   S   E   A   K   F 2350      2360      2370      2380      2390      2400
     cttgggctcagggactggatttcggccgatcggtggcggggctggggctctggcaagga
      L   G   S   G   T   G   F   R   P   I   G   G   G   A   G   G   S   G   K   E 2410      2420      2430      2440      2450      2460
     gttccaggcagcgctcggaggcaatgtccagcgggagcagttcacagttgtgatgctgac
      F   Q   A   A   L   G   G   N   V   Q   R   E   Q   F   T   V   V   M   L   T 2470      2480      2490      2500      2510      2520
     ctacgagcgggaggaagtgctcatgaactccctggagagactcaacggcctcccctacct
      Y   E   R   E   E   V   L   M   N   S   L   E   R   L   N   G   L   P   Y   L 2530      2540      2550      2560      2570      2580
     gaacaaggtagtggtggtgtggaactctcccaagctgccctcggaggaccttttgtggcc
      N   K   V   V   V   V   W   N   S   P   K   L   P   S   E   D   L   L   W   P 2590      2600      2610      2620      2630      2640
     agacattggtgtccccatcatggtcgtccgtactgagaagaacagtttgaacaatcggtt
      D   I   G   V   P   I   M   V   V   R   T   E   K   N   S   L   N   N   R   F 2650      2660      2670      2680      2690      2700
     cttgccctggaatgagattgagacagaggccatactgtccatcgacgatgatgctcacct
      L   P   W   N   E   I   E   T   E   A   I   L   S   I   D   D   D   A   H   L 2710      2720      2730      2740      2750      2760
     ccgccatgatgaaatcatgtttgggttttgggtgtggagagaagcacgtgatcgcattgt
      R   H   D   E   I   M   F   G   F   W   V   W   R   E   A   R   D   R   I   V 2770      2780      2790      2800      2810      2820
     gggtttccctggccggtaccatgcgtgggacatcccgcaccagtcctggctctacaattc
      G   F   P   G   R   Y   H   A   W   D   I   P   H   Q   S   W   L   Y   N   S 2830      2840      2850      2860      2870      2880
     caactactcctgtgagctgtccatggtgctgacgggcgctgccttctttcacaagtatta
      N   Y   S   C   E   L   S   M   V   L   T   G   A   A   F   F   H   K   Y   Y 2890      2900      2910      2920      2930      2940
     tgcctacctgtattcttatgtgatgccccaggccatccgggacatggtggacgagtacat
      A   Y   L   Y   S   Y   V   M   P   Q   A   I   R   D   M   V   D   E   Y   I 2950      2960      2970      2980      2990      3000
     caactgtgaggatatcgccatgaacttccttgtctcccacatcacacggaaacccccat
      N   C   E   D   I   A   M   N   F   L   V   S   H   I   T   R   K   P   P   I 3010      3020      3030      3040      3050      3060
     caaggtgacatcaaggtggacttttcgatgcccagggtgccctcaggccctgtcccatga
      K   V   T   S   R   W   T   F   R   C   P   G   C   P   Q   A   L   S   H   D
```

FIG. 7B-5

```
     3070      3080      3090      3100      3110      3120
tgactctcattttcacgagcggcacaagtgtatcaacttttttgtcaaggtgtacggcta
  D  S  H  F  H  E  R  H  K  C  I  N  F  F  V  K  V  Y  G  Y 3130      3140      3150      3160      3170      3180
tatgcctctcttgtacacacagttcagggtggactccgtgctcttcaagacccgcctgcc
  M  P  L  L  Y  T  Q  F  R  V  D  S  V  L  F  K  T  R  L  P 3190      3200      3210      3220      3230      3240
ccatgacaagaccaagtgcttcaagttcatctagggccttgcagttctgaggagacaatg
  H  D  K  T  K  C  F  K  F  I  *

3250      3260      3270      3280      3290      3300
agcagagcgagggggagtcaccctcaaggttcccaaggtgtcgaaggtccttggggacat 3310      3320      3330      3340      3350      3360
ctgtcgggcagggccaagacccttτgctgggagaggcagcaggaagagtggaaagggata 3370      3380      3390      3400      3410      3420
gctgtctttcattttgaagtcagccacactgggcctgggatcctggtcagagactcaggn 3430      3440      3450      3460      3470
cgtctgcacagggcactgactgatagcgaacactgaggactgttcataagcccaggaca
```

FIG. 8A-1

```
ggcgggtccc tgagctggaa gccggagagc aagccctgga ggttcactct ttcaagaagt
cgtgtgctga ggtgtaatgc tacacaagtc agaggaagga agggtcctga aacacatggc
ctgattgttg gcaaaggcat cataagaagc tggcatttat ttctgttcta acctattact
gtataactgt gaatagacac tatgcatatt tgttggtcag caaaaccaag aaacaagagc
tatggcattt gaaaaagtct gtctgattcc agggtgtttt tcctgggttt catcatcagg
tacctcctcc ctttcatctc agcaagaatg tggcacctit tatcgtttga taaagattaa
ggacatgttc tttggtcaac agccagaact taaaatctgc tggaataggg tcagagacca
tttcagctgc agctgaggaa aatgaaatgt tcattttatt tggtgccttg tctggggagc
acactaactc ttctggaaac gtgtcagtga aacagagatc gttttgtgga atagcaaccc
atggttatgg cgagtgaccc gacgtgatct gggggcagg ctgcagagga ctcatgacag
gctataccat gctgcggaat gggggcgcgg ggaacggagg tcagacctgc atgctgcgct
ggtccaaccg catccgcctc acgtggctca gcttcacgct ctttgtcatc ctggtcttct
tcccgctcat cgcccactat tacctcacca ctctggatga ggctgatgag gcaggcaagc
ggattttfgg tccccgggtg gggaacgagc tgtgcgaggt gaagcacgtg ctggatctgt
gccgcatccg ggagtcggtg agtgaagagc tcctgcagct ggaggccaag cgccaagagc
tgaacagcga gatcgccaag ctgaatctga agatcgaagc ctgtaagaag agcattgaga
acgccaagca ggacctgctc cagctcaaga atgtcatcag ccagaccgag cattcctaca
aggagctcat ggcccagaac cagcccaagc tgtccctgcc catccgactg ctcccagaga
aggacgatgc cggcctcct cccccgaagg ccactcgggg ctgccggcta cacaactgct
ttgattattc tcgttgccct ctcacctctg gcttcccggt ctacgtctat gacagtgacc
agtttgtctt tggcagctac ctggatccct tggtcaagca ggcttttcag gcgacagcac
gagctaacgt ttatgttaca gaaaatgcag acatcgcctg cctttacgtg atactagtgg
gagagatgca ggagcccgtg gtgctgcggc ctgctgagct ggagaagcag ttgtattccc
tgccacactg gcggacggat ggacacaacc atgtcatcat caatctgtca cgtaagtcag
atacacagaa ccttctctat aacgtcagta ctggccgtgc catggtggcc cagtccacct
tctacactgt ccagtacaga cctggctttg acttggtcgt atcaccgctg gtccatgcca
tgtctgagcc caacttcatg gaaatcccac cacaggtgcc ggtgaagcgg aaatatctct
tcaccttcca gggcgagaag attgagtctc tgaggtctag ccttcaggag gcccgctcct
tcgaagagga aatggagggc gaccctcccg ccgactacga tgaccggatc attgccaccc
tgaaggcggt gcaggacagc aagctggatc aggtcctggt ggaattcacc tgcaaaaacc
```

FIG. 8A-2

```
agcccaaacc cagcctgccg actgagtggg cactgtgtgg agagcgggag gaccgcttgg
aattgctgaa gctctccacc ttcgccctca tcattacccc cggggaccct cgcttggtta
tttcctctgg gtgtgcaaca cggctcttcg aagccctgga agtcggtgcc gtcccggtgg
tgctggggga gcaggtccag cttccctacc aggacatgct gcagtggaac gaggcggccc
tggtggtgcc aaagcctcgt gttaccgagg ttcatttcct gctcagaagc ctctccgata
gtgacctcct ggctatgagg cggcaaggcc gctttctctg ggagacttac ttctccactg
ctgacagtat ttttaatacc gtgctggcta tgattaggac tcgcatccag atcccagccg
ctcccatccg ggaagaggcg gcagctgaga tcccccaccg ttcaggcaag gcggctggaa
ctgaccccaa catggctgac aacggggacc tggacctggg gccagtggag acggagccgc
cctacgcctc acccagatac ctccgcaatt tcactctgac tgtcactgac ttttaccgca
gctggaactg tgctccaggg cctttccatc ttttccccca cactccctt gaccctgtgt
tgccctcaga ggccaaattc ttgggctcag ggactggctt tcggcctatt ggtggtggag
ctgggggttc tggcaaggaa tttcaggcag cgcttggagg caatgttccc cgagagcagt
tcacggtggt gatgttgact tatgagcggg aggaagtgct tatgaactct ttagagaggc
tgaatggcct cccttacctg aacaaggtcg tggtggtgtg gaattctccc aagctgccat
cagaggacct tctgtggcct gacattggcg ttcccatcat ggtggtccgt actgagaaga
acagtttgaa caaccgattc ttaccctgga atgaaattga gacagaggcc atcctgtcca
ttgatgacga tgctcacctc cgccatgacg aaatcatgtt tggggttccgg gtgtggagag
aagctcggga ccgcatcgtg ggcttccctg gccgttacca cgcatgggac atcccccatc
agtcctggct ctacaactcc aactactcct gtgagctgtc catggtgctg acaggtgctg
ccttctttca caagtattat gcctacctgt attcttatgt gatgcccag gccatccggg
acatggtgga tgaatacatc aactgtgagg acattgccat gaacttcctt gtctcccaca
tcactcggaa gcccccatc aaggtgacct cacggtggac attccgatgc ccaggatgcc
ctcaggccct gtctcatgat gactcccact ccacgagcg gcacaagtgc atcaacttct
tcgtgaaggt gtacggctac atgccctcc tgtacacgca gttcagggtg gattctgtgc
tcttcaagac acgcctgccc catgacaaga ccaagtgctt caagttcatc tagggcagc
gcacggtctg gggaagagga tgagcagagg gaggaagatg gctcccaagg ttcctaggca
ttgcaggacc ttgggcacat ctgctggtgg gtgcccaga gcctctgctg gaaggggcag
caggaggagt ggaaggaaac cgctgccttt atcttgaagt cagccacact gggcctggag
ccctgggcgg agtccccggg gttccccaca cagggcactg actgatagct tacactgagg
actgtggcga ctctgcagag tcactcacac cgttcgtacg cccaggacag ctggttcgtg
gtttttacat tcaataacaa ctattatgat tatttaaaaa gagaaagttt cagatttgcc
attcaaggct tatttatata tatgtgtgtg tatataaata catgcacaca cttgcataca
```

FIG. 8A-3

```
tatatatttt tggctggggg agtgtgagtt ttgccttcct aagggaggga ccgcgcaggc
tcctttgttc tgtattctgg cggagatggg tcctggcctt gtgtcactgg cttatcctta
aagatcatct cccatcctcc ccagcgccat ctgtgtgcag caaccagaaa gggatgaact
tggccctctt gcgggcctgg acaaggtctc ttccttaccc tttctgttgc cagtcagcaa
cctgtaactc acattctctt cccagtgaat ccctgggagc gcctgaccct ggtgggctgt
tcagcttcct gctgctgggg ccagcgattt ttgaggattt atctttaggc caggcttgcc
tccgtactta tccctgctct cccatttctc tcttgtttga gagagaatga ggaagcaaag
agtgagaaag aatagggggct gaagacgcca ctcccagatg gctctttcta tcctgctctt
ctgttgaaac acacgtgctg tgggcctcag gcgtttctga agtgctcttt cttggattgg
acaggagatc agcagcgtgc acatctgctg tggtctgaag tggtttgcag gtcagcctcc
tctccctagt gtagagcaag ccagtgtcct tcgaggaacc cacccggctg gccgggaagt
tttacagcaa ggcgcctgcc ttgggataat tccttggtga aattcacctt cccccgcct
ctgtctggag ccccatcctg tgttatctgt ggttttgga ccctaatgt cagcttggct
gtaggactcc ccgaggtttg gtatgtgcta gaacaatggg aggctgtgat ttgctgtgta
agctcacatc cagccttgga atctaacggg cattcacaac ccgagttacc actttccact
ccctgcttag gattctgttc cctgggctga aactgaaata agctaatttt ttgggtcacg
gtggcagtag gggaacctag gagggtgtga gtggcatttg tcaggatttt agcccatgac
gtgtttcttg aaccctactt tctggaagtg gagttgactc tggaagtttt ctagcaactg
aacaaaagct caggtttgtc ctggtcatgc acatgcctta agccagttcc gtcttccta
gaccttggca tcctgtgctt ctatttcttg gaatacgttc tcctctgacc tgcctgtacc
acgtgggtcc tcttcaagta ctgttttgaa gctgggctct tttgtgtagc tcccacccac
ctgtagggct agctcggctt aagggaactc tccccattgg caaaccggac cggccgccg
ccaggactgt gtttccaaag gttccccgcc cccaaccca gcatcagcct gtagctcccc
tgctgaggca gtgtggttat gttcccagca gtggggtca gacgcccttc ctcagaactt
tctagttgcc ctctacctga ctcctgactt gtattccttt tagcagtagc cttcttccct
cggggagcca aagagtgtgg tgtgtggcgc tatattgtgg ctgctatttc atctggtttc
ttttaatgtg aggaactcac atactgactt cagtgggact cggtgagccg gggccgtctg
tgtggtggga ccccctttag cgggactcag tgagctgggg ccgtctgtgt ggtggagcca
gggcctctcc ctttagtgga gccaggttgt cgggcccga atgtcactgg tggatctaag
aagggctgag tggtctgaca ccaaaacatg ccgcaggag ggctgtggtg ccggtgcttc
caacaaggac agccctcctt gaccctgaaa ggaacactgg cttgaaggac tgcagacagg
ctctgagggg cacgccctcc tcagcgagag gcagcaaggt ggccacagtg tcactggtca
ggtgcttctc accacgggaa agccgccgac ctgtgactcg cttgagatgg gaaagcggcg
ccacagaccc cgggtctcct tggctgtctg tgggccgccc ctggccacct tgtcctggct
cgcagggtgc aggagcgcct cgttctctgg gtggccggct tgctgctccg gtttgggctg
tcttaccata acaccgtccc agggctctgc aggccactgt gagcgctggc tccctgggca
gtgctcctcc gtgtggactg tgcctcaggc cagggctcac cagctggggt cctgtccgga
aggatgggat ctttctggga gctgcgccgg acagagtggg gagctcctag tttgtggggg
gaagctttga tatccatgcc acgtccatcc accccacccc ttttcgtcac gagcacaatg
gtcttacatt ggattttgt aaaaaataa aaataaatgg agactttaac tc
```

FIG. 8B-1

```
         10        20        30        40        50        60
ggcgggtccctgagctggaagccggagagcaagccctggaggttcactctttcaagaagt 70        80        90       100       110       120
cgtgtgctgaggtgtaatgctacacaagtcagaggaaggaagggtcctgaaacacatggc 130       140       150       160       170       180
ctgattgttggcaaaggcatcataagaagctggcatttatttctgttctaacctattact 190       200       210       220       230       240
gtataactgtgaatagacactatgcatatttgttggtcagcaaaaccaagaaacaagagc 250       260       270       280       290       300
tatggcatttgaaaaagtctgtctgattccagggtgttttcctgggtttcatcatcagg 310       320       330       340       350       360
tacctcctcccttctcatctcagcaagaatgtggcaccttttatcgtttgataaagattaa 370       380       390       400       410       420
ggacatgttctttggtcaacagccagaacttaaaatctgctggaatagggtcagagacca 430       440       450       460       470       480
tttcagctgcagctgaggaaaatgaaatgttcatttttatttggtgccttgtctggggagc 490       500       510       520       530       540
acactaactcttctggaaacgtgtcagtgaaacagagatcgttttgtggaatagcaaccc 550       560       570       580       590       600
atggttatggcgagtgacccgacgtgatctgggggcaggctgcagaggactcatgacag
                                                         M  T  G 610       620       630       640       650       660
gctataccatgctgcggaatgggggcgcggggaacggaggtcagacctgcatgctgcgct
 Y  T  M  L  R  N  G  A  G  N  G  G  Q  T  C  M  L  R  W 670       680       690       700       710       720
ggtccaaccgcatccgcctcacgtggctcagcttcacgctctttgtcatcctggtcttct
 S  N  R  I  R  L  T  W  L  S  F  T  L  F  V  I  L  V  F  F
```

FIG. 8B-2

```
       730        740        750        760        770        780
tcccgctcatcgcccactattacctcaccactctggatgaggctgatgaggcaggcaagc
  P  L  I  A  H  Y  Y  L  T  T  L  D  E  A  D  E  A  G  K  R 790        800        810        820        830        840
ggatttttggtccccgggtggggaacgagctgtgcgaggtgaagcacgtgctggatctgt
  I  F  G  P  R  V  G  N  E  L  C  E  V  K  H  V  L  D  L  C 850        860        870        880        890        900
gccgcatccgggagtcggtgagtgaagagctcctgcagctggaggccaagcgccaagagc
  R  I  R  E  S  V  S  E  E  L  L  Q  L  E  A  K  R  Q  E  L 910        920        930        940        950        960
tgaacagcgagatcgccaagctgaatctgaagatcgaagcctgtaagaagagcattgaga
  N  S  E  I  A  K  L  N  L  K  I  E  A  C  K  K  S  I  E  N 970        980        990       1000       1010       1020
acgccaagcaggacctgctccagctcaagaatgtcatcagccagaccgagcattcctaca
  A  K  Q  D  L  L  Q  L  K  N  V  I  S  Q  T  E  H  S  Y  K 1030       1040       1050       1060       1070       1080
aggagctcatggcccagaaccagcccaagctgtccctgcccatccgactgctcccagaga
  E  L  M  A  Q  N  Q  P  K  L  S  L  P  I  R  L  L  P  E  K 1090       1100       1110       1120       1130       1140
aggacgatgccggcctccctcccccgaaggccactcggggctgccggctacacaactgct
  D  D  A  G  L  P  P  P  K  A  T  R  G  C  R  L  H  N  C  F 1150       1160       1170       1180       1190       1200
ttgattattctcgttgccctctcacctctggcttcccggtctacgtctatgacagtgacc
  D  Y  S  R  C  P  L  T  S  G  F  P  V  Y  V  Y  D  S  D  Q 1210       1220       1230       1240       1250       1260
agtttgtctttggcagctacctggatcccttggtcaagcaggcttttcaggcgacagcac
  F  V  F  G  S  Y  L  D  P  L  V  K  Q  A  F  Q  A  T  A  R 1270       1280       1290       1300       1310       1320
gagctaacgtttatgttacagaaaaatgcagacatcgcctgcctttacgtgatactagtgg
  A  N  V  Y  V  T  E  N  A  D  I  A  C  L  Y  V  I  L  V  G 1330       1340       1350       1360       1370       1380
gagagatgcaggagcccgtggtgctgcggcctgctgagctggagaagcagttgtattccc
  E  M  Q  E  P  V  V  L  R  P  A  E  L  E  K  Q  L  Y  S  L 1390       1400       1410       1420       1430       1440
tgccacactggcggacggatggacacaaccatgtcatcatcaatctgtcacgtaagtcag
  P  H  W  R  T  D  G  H  N  H  V  I  I  N  L  S  R  K  S  D 1450       1460       1470       1480       1490       1500
atacacagaaccttctctataacgtcagtactggccgtgccatggtggcccagtccacct
  T  Q  N  L  L  Y  N  V  S  T  G  R  A  M  V  A  Q  S  T  F
```

FIG. 8B-3

```
       1510      1520      1530      1540      1550      1560
tctacactgtccagtacagacctggctttgacttggtcgtatcaccgctggtccatgcca
 Y  T  V  Q  Y  R  P  G  F  D  L  V  V  S  P  L  V  H  A  M 1570      1580      1590      1600      1610      1620
tgtctgagcccaacttcatggaaatcccaccacaggtgccggtgaagcggaaatatctct
 S  E  P  N  F  M  E  I  P  P  Q  V  P  V  K  R  K  Y  L  F 1630      1640      1650      1660      1670      1680
tcaccttccagggcgagaagattgagtctctgaggtctagccttcaggaggcccgctcct
 T  F  Q  G  E  K  I  E  S  L  R  S  S  L  Q  E  A  R  S  F 1690      1700      1710      1720      1730      1740
tcgaagaggaaatggagggcgaccctcccgccgactacgatgaccggatcattgccaccc
 E  E  E  M  E  G  D  P  P  A  D  Y  D  D  R  I  I  A  T  L 1750      1760      1770      1780      1790      1800
tgaaggcggtgcaggacagcaagctggatcaggtcctggtggaattcacctgcaaaaacc
 K  A  V  Q  D  S  K  L  D  Q  V  L  V  E  F  T  C  K  N  Q 1810      1820      1830      1840      1850      1860
agcccaaacccagcctgccgactgagtgggcactgtgtggagagcgggaggaccgcttgg
 P  K  P  S  L  P  T  E  W  A  L  C  G  E  R  E  D  R  L  E 1870      1880      1890      1900      1910      1920
aattgctgaagctctccaccttcgccctcatcattaccccggggacccctcgcttggtta
 L  L  K  L  S  T  F  A  L  I  I  T  P  G  D  P  R  L  V  I 1930      1940      1950      1960      1970      1980
tttcctctgggtgtgcaacacggctcttcgaagccctggaagtcggtgccgtcccggtgg
 S  S  G  C  A  T  R  L  F  E  A  L  E  V  G  A  V  P  V  V 1990      2000      2010      2020      2030      2040
tgctgggggagcaggtccagcttccctaccaggacatgctgcagtggaacgaggcggccc
 L  G  E  Q  V  Q  L  P  Y  Q  D  M  L  Q  W  N  E  A  A  L 2050      2060      2070      2080      2090      2100
tggtggtgccaaagcctcgtgttaccgaggttcatttcctgctcagaagcctctccgata
 V  V  P  K  P  R  V  T  E  V  H  F  L  L  R  S  L  S  D  S 2110      2120      2130      2140      2150      2160
gtgacctcctggctatgaggcggcaaggccgctttctctgggagacttacttctccactg
 D  L  L  A  M  R  R  Q  G  R  F  L  W  E  T  Y  F  S  T  A 2170      2180      2190      2200      2210      2220
ctgacagtatttttaataccgtgctggctatgattaggactcgcatccagatcccagccg
 D  S  I  F  N  T  V  L  A  M  I  R  T  R  I  Q  I  P  A  A 2230      2240      2250      2260      2270      2280
ctcccatccgggaagaggcggcagctgagatccccaccgttcaggcaaggcggctggaa
 P  I  R  E  E  A  A  A  E  I  P  H  R  S  G  K  A  A  G  T
```

FIG. 8B-4

```
     2290      2300      2310      2320      2330      2340
ctgaccccaacatggctgacaacggggacctggacctggggccagtggagacggagccgc
  D  P  N  M  A  D  N  G  D  L  D  L  G  P  V  E  T  E  P  P 2350      2360      2370      2380      2390      2400
cctacgcctcacccagatacctccgcaatttcactctgactgtcactgacttttaccgca
  Y  A  S  P  R  Y  L  R  N  F  T  L  T  V  T  D  F  Y  R  S 2410      2420      2430      2440      2450      2460
gctggaactgtgctccagggccttttccatcttttcccccacactccctttgaccctgtgt
  W  N  C  A  P  G  P  F  H  L  F  P  H  T  P  F  D  P  V  L 2470      2480      2490      2500      2510      2520
tgccctcagaggccaaattcttgggctcagggactggctttcggcctattggtggtggag
  P  S  E  A  K  F  L  G  S  G  T  G  F  R  P  I  G  G  G  A 2530      2540      2550      2560      2570      2580
ctgggggttctggcaaggaatttcaggcagcgcttggaggcaatgttccccgagagcagt
  G  G  S  G  K  E  F  Q  A  A  L  G  G  N  V  P  R  E  Q  F 2590      2600      2610      2620      2630      2640
tcacggtggtgatgttgacttatgagcgggaggaagtgcttatgaactctttagagaggc
  T  V  V  M  L  T  Y  E  R  E  E  V  L  M  N  S  L  E  R  L 2650      2660      2670      2680      2690      2700
tgaatggcctcccttacctgaacaaggtcgtggtggtgtggaattctcccaagctgccat
  N  G  L  P  Y  L  N  K  V  V  V  V  W  N  S  P  K  L  P  S 2710      2720      2730      2740      2750      2760
cagaggaccttctgtggcctgacattggcgttcccatcatggtggtccgtactgagaaga
  E  D  L  L  W  P  D  I  G  V  P  I  M  V  V  R  T  E  K  N 2770      2780      2790      2800      2810      2820
acagtttgaacaaccgattcttaccctggaatgaaattgagacagaggccatcctgtcca
  S  L  N  N  R  F  L  P  W  N  E  I  E  T  E  A  I  L  S  I 2830      2840      2850      2860      2870      2880
ttgatgacgatgctcacctccgccatgacgaaatcatgtttgggttccgggtgtggagag
  D  D  D  A  H  L  R  H  D  E  I  M  F  G  F  R  V  W  R  E 2890      2900      2910      2920      2930      2940
aagctcgggaccgcatcgtgggcttccctggccgttaccacgcatgggacatcccccatc
  A  R  D  R  I  V  G  F  P  G  R  Y  H  A  W  D  I  P  H  Q 2950      2960      2970      2980      2990      3000
agtcctggctctacaactccaactactcctgtgagctgtccatggtgctgacaggtgctg
  S  W  L  Y  N  S  N  Y  S  C  E  L  S  M  V  L  T  G  A  A 3010      3020      3030      3040      3050      3060
ccttctttcacaagtattatgcctacctgtattcttatgtgatgccccaggccatccggg
  F  F  H  K  Y  Y  A  Y  L  Y  S  Y  V  M  P  Q  A  I  R  D
```

FIG. 8B-5

```
      3070      3080      3090      3100      3110      3120
acatggtggatgaatacatcaactgtgaggacattgccatgaacttccttgtctcccaca
   M   V   D   E   Y   I   N   C   E   D   I   A   M   N   F   L   V   S   H   I 3130      3140      3150      3160      3170      3180
tcactcggaagcccccatcaaggtgacctcacggtggacattccgatgcccaggatgcc
   T   R   K   P   P   I   K   V   T   S   R   W   T   F   R   C   P   G   C   P 3190      3200      3210      3220      3230      3240
ctcaggccctgtctcatgatgactcccacttccacgagcggcacaagtgcatcaacttct
   Q   A   L   S   H   D   D   S   H   F   H   E   R   H   K   C   I   N   F   F 3250      3260      3270      3280      3290      3300
tcgtgaaggtgtacggctacatgccctcctgtacacgcagttcagggtggattctgtgc
   V   K   V   Y   G   Y   M   P   L   L   Y   T   Q   F   R   V   D   S   V   L 3310      3320      3330      3340      3350      3360
tcttcaagacacgcctgccccatgacaagaccaagtgcttcaagttcatctaggggcagc
   F   K   T   R   L   P   H   D   K   T   K   C   F   K   F   I   *

3370      3380      3390      3400      3410      3420
gcacggtctggggaagaggatgagcagagggaggaagatggctcccaaggttcctaggca 3430      3440      3450      3460      3470      3480
ttgcaggaccttgggcacatctgctggtgggtggcccagagcctctgctggaaggggcag 3490      3500      3510      3520      3530      3540
caggaggagtggaaggaaaccgctgcctttatcttgaagtcagccacactgggcctggag 3550      3560      3570      3580      3590      3600
ccctgggcggagtccccggggttccccacacagggcactgactgatagcttacactgagg 3610      3620      3630      3640      3650      3660
actgtggcgactctgcagagtcactcacaccgttcgtacgcccaggacagctggttcgtg 3670      3680      3690      3700      3710      3720
gttttacattcaataacaactattatgattatttaaaaagagaaagtttcagatttgcc 3730      3740      3750      3760      3770      3780
attcaaggcttatttatatatatgtgtgtgtatataaatacatgcacacacttgcataca 3790      3800      3810      3820      3830      3840
tatatattttggctgggggagtgtgagttttgcctttctaagggagggaccgcgcaggc
```

FIG. 8B-6

```
          3850      3860      3870      3880      3890      3900
tcctttgttctgtattctggcggagatgggtcctggccttgtgtcactggcttatcctta 3910      3920      3930      3940      3950      3960
aagatcatctcccatcctccccagcgccatctgtgtgcagcaaccagaaagggatgaact 3970      3980      3990      4000      4010      4020
tggccctcttgcgggcctggacaaggtctcttccttacccttctgttgccagtcagcaa 4030      4040      4050      4060      4070      4080
cctgtaactcacattctcttcccagtgaatccctgggagcgcctgaccctggtgggctgt 4090      4100      4110      4120      4130      4140
tcagcttcctgctgctggggccagcgattttgaggatttatctttaggccaggcttgcc 4150      4160      4170      4180      4190      4200
tccgtacttatccctgctctcccatttctctcttgtttgagagagaatgaggaagcaaag 4210      4220      4230      4240      4250      4260
agtgagaaagaataggggctgaagacgccactcccagatggctcttctatcctgctctt 4270      4280      4290      4300      4310      4320
ctgttgaaacacacgtgctgtgggcctcaggcgtttctgaagtgctctttcttggattgg 4330      4340      4350      4360      4370      4380
acaggagatcagcagcgtgcacatctgctgtggtctgaagtggtttgcaggtcagcctcc 4390      4400      4410      4420      4430      4440
tctccctagtgtagagcaagccagtgtccttcgaggaacccaccggctggccgggaagt 4450      4460      4470      4480      4490      4500
tttacagcaaggcgcctgccttgggataattccttggtgaaattcaccttcccccgcct 4510      4520      4530      4540      4550      4560
ctgtctggagccccatcctgtgttatctgtggttttggacccctaatgtcagcttggct 4570      4580      4590      4600      4610      4620
gtaggactccccgaggtttggtatgtgctagaacaatgggaggctgtgatttgctgtgta
```

FIG. 8B-7

```
     4630      4640      4650      4660      4670      4680
agctcacatccagccttggaatctaacgggcattcacaacccgagttaccactttccact 4690      4700      4710      4720      4730      4740
ccctgcttaggattctgttccctgggctgaaactgaaataagctaattttttgggtcacg 4750      4760      4770      4780      4790      4800
gtggcagtaggggaacctaggagggtgtgagtggcatttgtcagggatttagcccatgac 4810      4820      4830      4840      4850      4860
gtgtttcttgaaccctactttctggaagtggagttgactctggaagttttctagcaactg 4870      4880      4890      4900      4910      4920
aacaaaagctcaggtttgtcctggtcatgcacatgccttaagccagttccgtcttcccta 4930      4940      4950      4960      4970      4980
gaccttggcatcctgtgcttctatttcttggaatacgttctcctctgacctgcctgtacc 4990      5000      5010      5020      5030      5040
acgtgggtcctcttcaagtactgttttgaagctgggctcttttgtgtagctcccacccac 5050      5060      5070      5080      5090      5100
ctgtagggctagctcggcttaagggaactctccccattggcaaaccggacccggccgccg 5110      5120      5130      5140      5150      5160
ccaggactgtgtttccaaaggttccccgccccaacccagcatcagcctgtagctcccc 5170      5180      5190      5200      5210      5220
tgctgaggcagtgtggttatgttcccagcagtgggggtcagacgcccttcctcagaactt 5230      5240      5250      5260      5270      5280
tctagttgccctctacctgactcctgacttgtattccttttagcagtagccttcttccct 5290      5300      5310      5320      5330      5340
cggggagccaaagagtgtggtgtgtggcgctatattgtggctgctatttcatctggtttc 5350      5360      5370      5380      5390      5400
ttttaatgtgaggaactcacatactgacttcagtgggactcggtgagccggggccgtctg
```

FIG. 8B-8

```
        5410      5420      5430      5440      5450      5460
tgtggtgggaccccctttagcgggactcagtgagctggggccgtctgtgtggtggagcca 5470      5480      5490      5500      5510      5520
gggcctctccctttagtggagccaggttgtcgggccccgaatgtcactggtggatctaag 5530      5540      5550      5560      5570      5580
aagggctgagtggtctgacaccaaaacatgccgcagggagggctgtggtgccggtgcttc 5590      5600      5610      5620      5630      5640
caacaaggacagccctccttgaccctgaaaggaacactggcttgaaggactgcagacagg 5650      5660      5670      5680      5690      5700
ctctgaggggcacgccctcctcagcgagaggcagcaaggtggccacagtgtcactggtca 5710      5720      5730      5740      5750      5760
ggtgcttctcaccacgggaaagccgccgacctgtgactcgcttgagatgggaaagcggcg 5770      5780      5790      5800      5810      5820
ccacagacccgggtctccttggctgtctgtgggccgcccctggccaccttgtcctggct 5830      5840      5850      5860      5870      5880
cgcagggtgcaggagcgcctcgttctctgggtggccggcttgctgctccggtttgggctg 5890      5900      5910      5920      5930      5940
tcttaccataacaccgtcccagggctctgcaggccactgtgagcgctggctccctgggca 5950      5960      5970      5980      5990      6000
gtgctcctccgtgtggactgtgcctcaggccagggctcaccagctggggtcctgtccgga 6010      6020      6030      6040      6050      6060
aggatgggatctttctgggagctgcgccggacagagtgggcagctcctagtttgtgggg 6070      6080      6090      6100      6110      6120
gaagctttgatatccatgccacgtccatccacccacccctttcgtcacgagcacaatg 6130      6140      6150      6160      6170
gtcttacattggatttttgtaaaaaaataaaaataaatggagacttta actc
```

FIG. 9A

```
Murine TREX   1  MTGYTMLRNGGVGNGGQTCMLRWSNRIRLTWLSFTLFIILVFFPLIAHYYLTTLDEADEA
Human  TREX   1  MTGYTMLRNGGAGNGGQTCMLRWSNRIRLTWLSFTLFVILVFFPLIAHYYLTTLDEADEA Murine TREX  61  GKRIFGPRAGSELCEVKHVLDLCRIRESVSEELLQLEAKRQELNSEIAKLNLKIEACKKS
Human  TREX  61  GKRIFGPRVGNELCEVKHVLDLCRIRESVSEELLQLEAKRQELNSEIAKLNLKIEACKKS Murine TREX 121  IENAKQDLLQLKNVISQTEHSYKELMAQNQPKLSLPIRLLPEKDDAGLPPPKVTRGCRLH
Human  TREX 121  IENAKQDLLQLKNVISQTEHSYKELMAQNQPKLSLPIRLLPEKDDAGLPPPHATRGCRLH Murine TREX 181  NCFDYSRCPLTSGFPVYVYDSDQFAFGSYLDPLVKQAFQATMRANVYVTENAAIACLYVV
Human  TREX 181  NCFDYSRCPLTSGPPVYVYDSDQFVFGSYLDPLVKQAFQATARANVYVTENADIACLYVI Murine TREX 241  LVGEMQEPTVLRPADLEKQLFSLPHWRTDGHNHVIINLSRKSDTQNLLYNVSTGRH-VAQ
Human  TREX 241  LVGEMQEPVVLRPAELEKQLMSLPHWRTDGHNHVIINLSRKSDTQNLLYNVSTGRAMVAQ Murine TREX 300  STLVAADYRAGFDLVVSPLVHAMSEPNFMEIPPQVPVKRKYLFTFQGEKIESLRSSLQEA
Human  TREX 301  STFKTVDYRPGFDLVVSPLVHAMSEPNFMEIPPQVPVKRKYLFTFQGEKIESLRSSLQEA Murine TREX 360  RSFEEEMEGDPPADYDDRIIATLKAVQDSKLDQVLVEFTCKNQPKPSLPTEWALCGERED
Human  TREX 361  RSFEEEMEGDPPADYDDRIIATLKAVQDSKLDQVLVEFTCKNQPKPSLPTEWALCGERED Murine TREX 420  RLELLKLSTPALIITPGDPRLLISSGCATRLFEALEVGAVPVVLGEQVQLPYHDMLQWNE
Human  TREX 421  RLELLKLSTPALIITPGDPRLVISSGCATRLFEALEVGAVPVVLGEQVQLPYQDMLQWNE Murine TREX 480  AALVVPKPRVTEVHFLLRSLSDSDLLAMRRQGRFLWETYFSTADSIFNTVLAMIRTRIQI
Human  TREX 481  AALVVPKPRVTEVHFLLRSLSDSDLLAMRRQGRFLWETYFPTADSIFNTVLAMIRTRIQI Murine TREX 540  PAAPIREEVAAEIPHRSGKAAGTDPNMADNGDLDLGPVETEPPYASPKYLRNFTLTVTDC
Human  TREX 541  PAAPIREEAAAEIPHRSGKAAGTDPNMADNGDLDLGPVETEPPYASPRYLRNFTLTVTDF Murine TREX 600  YRGWNSAPGRFHLFPHTPFDPVLPSEAKFLGSGTGFRPIGGGAGGSGKEFQAALGGNVQR
Human  TREX 601  YRSWNCAPGPFHLFPHTPFDPVLPSEAKFLGSGTGFRPIGGGAGGSGKEFQAALGGNVPR Murine TREX 660  EQFTVVMLTYEREEVLMNSLERLNGLPYLNKVVVVWNSPKLPSEDLLWPDIGVPIMVVRT
Human  TREX 661  EQFTVVMLTYEREEVLMNSLERLNGLPYLNKVVVVWNSPKLPSEDLLWPDIGVPIMVVRT Murine TREX 720  EKNSLNNRFLPWNEIETEAILSIDDDAHLRHDEIMFGFWVWREARDRIVGFPGRYHAWDI
Human  TREX 721  EKNSLNNRFLPWNEIETEAILSIDDDAHLRHDEIMFGFRVWREARDRIVGFPGRYHAWDI Murine TREX 780  PHQSWLYNSNYSCELSHVLTGAAFFHKYYAYLYSYVMPQAIRDMVDEYINCEDIAMNFLV
Human  TREX 781  PHQSWLYNSNYSCELSHVLTGAAFFHKYYAYLYSYVMPQAIRDMVDEYINCEDIAMNFLV Murine TREX 840  SHITRKPPIKVTSRWTFRCPGCPQALSHDDSHFHERHKCINPFVKVYGYMPLLYTQFRVD
Human  TREX 841  SHITRKPPIKVTSRWTFRCPGCPQALSHDDSHFHERHKCINFFVKVYGYMPLLYTQFRVD Murine TREX 900  SVLFKTRLPHDKTKCFKFI
Human  TREX 901  SVLFKTRLPHDKTKCFKFI
```

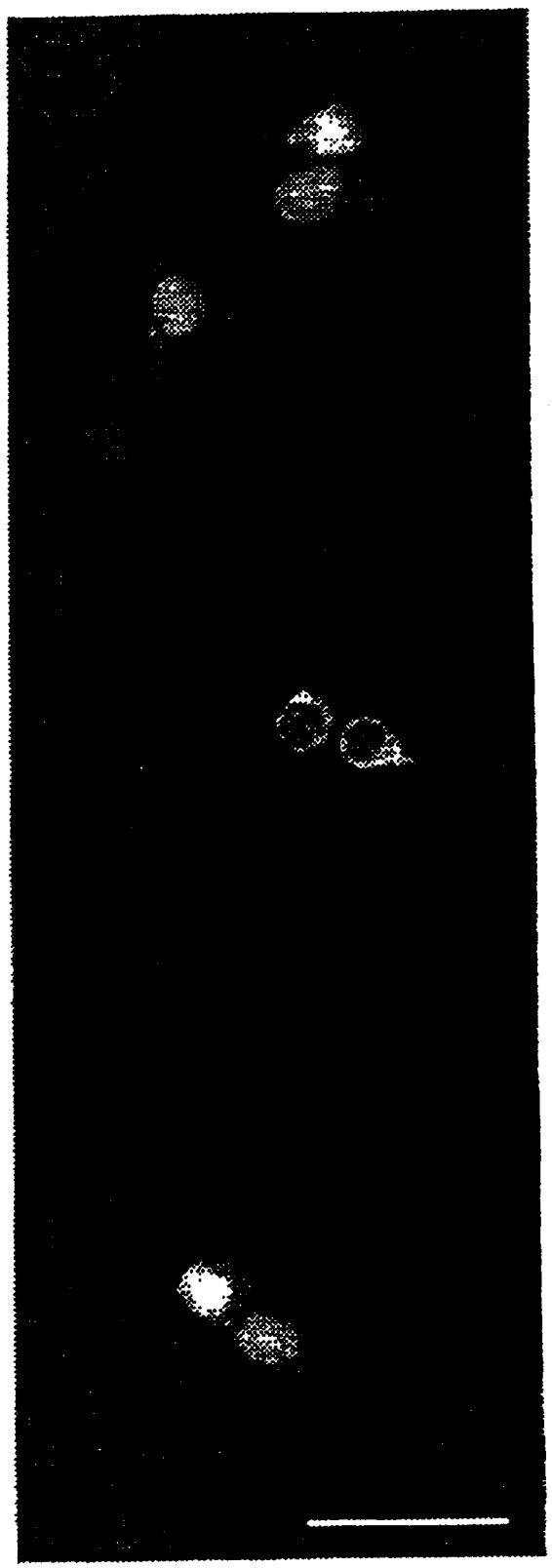
FIG. 11D-a
FIG. 11D-b
FIG. 11D-c

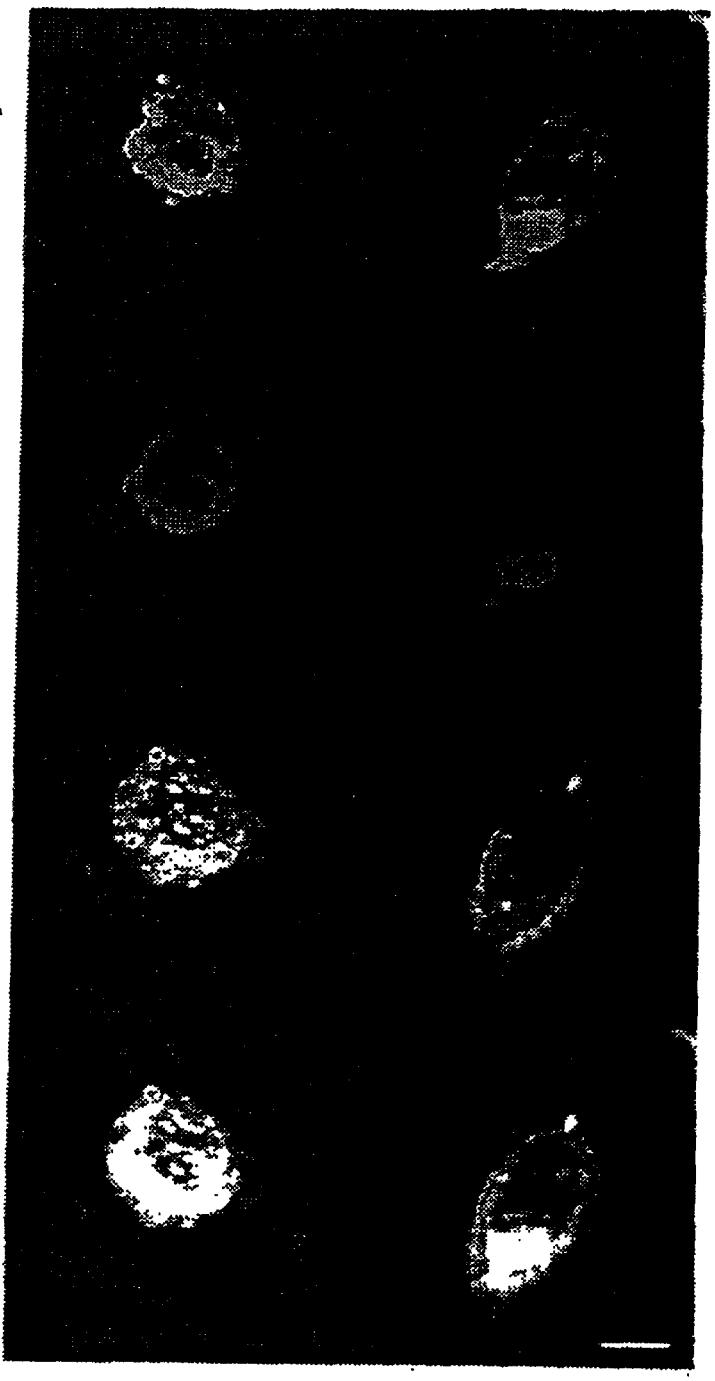

TREX, A NOVEL GENE OF TRAF-INTERACTING EXT GENE FAMILY AND DIAGNOSTIC AND THERAPEUTIC USES THEREOF

This application is a continuation of PCT International Application No. PCT/US99/21654, filed 17 Sep. 1999, designating the United States of America, which is a continuation-in-part and claims priority of U.S. Ser. No. 09/156,191, filed Sep. 17, 1998, now abandoned the contents of which are hereby incorporated by reference into the present application.

STATEMENT REGARDING FEDERALLY FUNDED RESEARCH

The invention disclosed herein was made in part with Government support under NIH Grant No. R01GM55147. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Tumor necrosis factor (TNF) receptor-associated factor (TRAF) proteins contribute to signal transduction induced by TNF receptor family signaling. TRAF3 cloned as binding protein to the cytoplastic domain of CD40, a member of TNF receptor superfamily, is believed to be involved in signaling pathway induced by CD40, Lymphotoxin (LT) β receptor, CD30 ligation (1–7). Here we report molecular cloning of a novel TRAF-interacting protein named as TREX because of TRAF-interacting EXT (hereditary multiple exostoses) gene family protein. TREX has highly homologous sequence to the EXT gene family, a candidate of tumor suppressor gene. TREX strongly interacts with TRAF2 and TRAF3, and TREX and TRAF protein colocalize in mammalian cells. Moreover, overexpression of TREX modulates NF-kB activity induced by TRAF-mediated signaling. These findings indicate that TREX and the other EXT gene family proteins can function as a mediator in receptor signaling and could be involved in tumorigenesis.

SUMMARY OF THE INVENTION

This invention provides an isolated nucleic acid molecule encoding a Tumor necrosis factor Receptor-Associated Factor (TRAF) protein-interacting hereditary multiple extoses (TREX) protein.

This invention provides an isolated nucleic acid molecule encoding a mutant homolog of the mammalian Tumor necrosis factor Receptor-Associated Factor (TRAF) protein-interacting hereditary multiple extoses (TREX) protein whose mutant sequences (genetic alterations) are shown in Table 3 infra.

This invention provides a vector comprising the isolated nucleic acid molecule encoding a Tumor necrosis factor Receptor-Associated Factor (TRAF) protein-interacting hereditary multiple extoses (TREX) protein.

This invention provides a purified mammalian Tumor necrosis factor Receptor-Associated Factor (TRAF) protein-interacting hereditary multiple extoses (TREX) protein.

This invention provides a protein comprising substantially the amino acid sequence set forth in FIG. 1A (SEQ ID NOS: 2 and 4).

This invention provides an oligonucleotide comprising a nucleic acid molecule of at least 15 nucleotides capable of specifically hybridizing with a unique sequence included within the sequence of an isolated nucleic acid molecule encoding a Tumor necrosis factor Receptor-Associated Factor (TRAF) protein-interacting hereditary multiple extoses (TREX) protein.

This invention provides an antisense oligonucleotide comprising a sequence capable of specifically hybridizing with a unique sequence included within an mRNA molecule encoding a Tumor necrosis factor Receptor-Associated Factor (TRAF) protein-interacting hereditary multiple extoses (TREX) protein.

This invention provides an antisense oligonucleotide comprising a sequence capable of specifically hybridizing with a unique sequence included within a genomic DNA molecule encoding a Tumor necrosis factor Receptor-Associated Factor (TRAF) protein-interacting hereditary multiple extoses (TREX) protein.

This invention provides a monoclonal antibody directed to an epitope of a Tumor necrosis factor Receptor-Associated Factor (TRAF) protein-interacting hereditary multiple extoses (TREX) protein.

This invention provides a method of inhibiting TREX protein interaction with a TRAF protein comprising administering a ligand comprising an amino acid domain which binds to a EXT C domain of the TREX protein so as to inhibit binding of the TREX protein to the TRAF protein.

This invention provides a method of inhibiting overexpression of TREX protein comprising administering any of the above-described antisense oligonucleotides which bind to an mRNA molecule encoding a human Tumor necrosis factor Receptor-Associated Factor (TRAF) protein-interacting hereditary multiple extoses (TREX) protein so as to inhibit overexpression of the human TREX protein.

This invention provides a method of inhibiting growth of a tumor cell comprising blocking a TRAF interacting site of a TREX protein by administering a ligand capable of binding to the TRAF interacting site of a TREX protein.

This invention provides a pharmaceutical composition comprising an amount of any of the above-described oligonucleotides effective to prevent overexpression of a TREX protein and a pharmaceutically acceptable carrier capable of passing through a cell membrane.

This invention provides a pharmaceutical composition comprising an amount of any of the above-described antibodies effective to block binding of a TREX protein to a TRAF protein and a pharmaceutically acceptable carrier capable of passing through a cell membrane.

This invention provides a method of treating an abnormality in a subject, wherein the abnormality is alleviated by the inhibition of binding of a TREX protein and a TRAF protein which comprises administering to the subject an effective amount of the above described pharmaceutical composition effective to block binding of the TREX protein and the TRAF protein in the subject, thereby treating the abnormality in the subject.

This invention provides a method of treating an abnormality in a subject, wherein the abnormality is alleviated by the inhibition of overexpression of a TREX protein which comprises administering to the subject an effective amount of the above-described pharmaceutical composition effective to inhibit overexpression of the TREX protein, thereby treating the abnormality in the subject. In a preferred embodiment the abnormality is cancer, a hereditary multiple extosis or an autoimmune disease.

This invention provides a method of screening for a chemical compound which inhibits TREX protein and TRAF protein binding comprising: (a) incubating the chemical compound with a TREX protein and a TRAF protein; (b) contacting the incubate of step (a) with an affinity medium under conditions so as to bind a TREX protein-TRAF protein complex, if such a complex forms; and (c) measuring the amount of the TREX protein-TRAF protein complex formed in step (b) so as to determine whether the compound is capable of interfering with the formation of the complex between the TREX protein-TRAF protein.

This invention provides a method of preventing inhibition of a CD40 signal-dependent NF-kB activation comprising administering any of the above-described antisense oligonucleotides which bind to an mRNA molecule encoding a human Tumor necrosis factor Receptor-Associated Factor (TRAF) protein-interacting hereditary multiple extoses (TREX) protein so as to prevent inhibition of CD40 signal-dependent NF-kB activation.

This invention provides a method of preventing inhibition of activation of a CD40 signal-dependent NF-kB comprising administering a ligand comprising an amino acid domain which binds to a EXT C domain of the TREX protein so as to inhibit binding of the TREX protein to the TRAF protein, thereby preventing inhibition of activation of a CD40 signal-dependent NF-kB.

This invention provides a method of preventing upregulation of a TNF receptor typeII signal-dependent NF-kB activation comprising administering any of the above-described antisense oligonucleotides which bind to an mRNA molecule encoding a human Tumor necrosis factor Receptor-Associated Factor (TRAF) protein-interacting hereditary multiple extoses (TREX) protein so as to prevent upregulation of a TNF receptor typeII (TNFRII) signal-dependent NF-kB activation.

This invention provides a method of preventing upregulation of activation of a TNF receptor typeII (TNFRII)-signal-dependent NF-kB comprising administering a ligand comprising an amino acid domain which binds to a EXT C domain of the TREX protein so as to inhibit binding of the TREX protein to the TRAF protein, thereby preventing upregulation of activation of a TNF receptor typeII-signal-dependent NF-kB.

This invention provides a method of detecting a predisposition to cancer which comprises detecting of a mutation in a nucleic acid encoding TREX protein in the sample from the subject.

This invention provides a TREX nucleic acid probe comprising a sequence capable of specifically hybridizing with a unique sequence included within the above-described isolated DNA molecule encoding a Tumor necrosis factor Receptor-Associated Factor (TRAF) protein-interacting hereditary multiple extoses (TREX) protein.

This invention provides a method of diagnosing cancer in a subject which comprises: a) obtaining DNA from the sample of a subject suffering from cancer; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a genetic alteration of a nucleic acid molecule encoding a TREX protein, wherein the nucleic acid is labeled with a detectable marker; e) detecting labeled bands which have hybridized to the nucleic acid probe in step (d), wherein the sequence of a genetic alteration of a nucleic acid molecule encoding a TREX protein creates a unique band pattern specific to the DNA of subjects suffering from cancer; f) preparing DNA obtained from a sample of a subject for diagnosis by steps (a-e); and g) comparing the detected band pattern specific to the DNA obtained from a sample of subjects suffering from cancer from step (e) and the DNA obtained from a sample of the subject for diagnosis from step (f) to determine whether the patterns are the same or different and to diagnose thereby predisposition to cancer if the patterns are the same.

This invention provides a method of diagnosing cancer in a subject which comprises: a) obtaining RNA from the sample of the subject suffering from cancer; b) separating the RNA sample by size fractionation; c) contacting the resulting RNA species with a nucleic acid probe capable of specifically hybridizing with a unique sequence included within the sequence of a nucleic acid molecule encoding a mutated TREX protein, wherein the sequence of the nucleic acid molecule encoding the mutated TREX protein is labeled with a detectable marker; d) detecting labeled bands which have hybridized to the RNA species to create a unique band pattern specific to the RNA of subjects suffering from cancer; e) preparing RNA obtained from a sample of a subject for diagnosis by steps (a-d); and f) comparing the detected band pattern specific to the RNA obtained from a sample of subjects suffering from cancer from step (d) and the RNA obtained from a sample of the subject for diagnosis from step (f) to determine whether the patterns are the same or different and to diagnose thereby predisposition to cancer if the patterns are the same.

BRIEF DESCRIPTION OF THE FIGURES

Figure 1D:
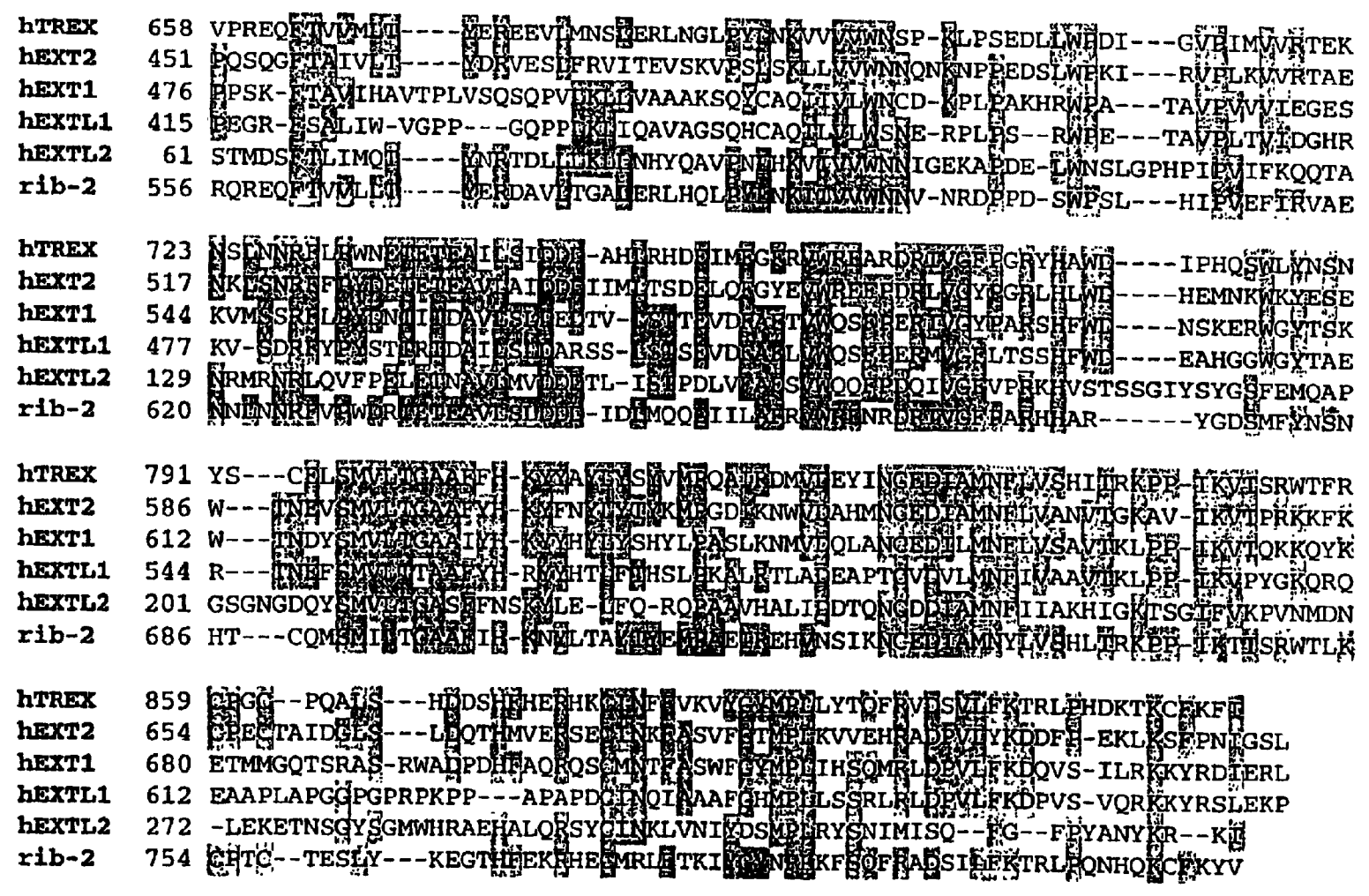

FIGS. 1A-1F. Amino acid sequences of TREX and expression of TREX. FIG. 1A, Predicted amino acid sequences of mouse and human TREX. Identical residues are boxed. Partial clones obtained by two-hybrid screening are indicated by brackets. Isoleucine and leucine residues that form putative isoleucine zipper motif are boxed and darkly shaded. FIG. 1B, Schematic representation of putative domain structure of EXT gene family proteins. Conserved domains are indicated as EXT-N and EXT-C domain. FIG. 1C, Sequence alignments of EXT-N domain. Conserved residues are shaded. FIG. 1D, Sequence alignments of EXT-C domain. Conserved residues are shaded. FIG. 1E, Northern blot analysis of TREX mRNA. Multiple tissue northern blot (Clontech) were probed with human or mouse TREX cDNA. FIG. 1F, Expression of TREX protein in human cells. Cell lysates of KM12L4 cell line were immunoprecipitated with either rabbit preimmune IgG or rabbit anti-TREX antibody. TREX proteins were detected with anti-TREX antibody (107 kDa).

FIGS. 2A-B. Intracellular association of TREX and TRAF family proteins. FIG. 2A, 293 T cells were transiently transfected with myc-tagged TREX together with FLAG-tagged TRAFs. Cell lysates were immunoprecipitated with preimmune rabbit IgG (Control) or rabbit anti-myc antibody (αmyc). Coimmunoprecipitated TRAF proteins were analyzed by Western blotting using anti-FLAG antibody. Expression of TRAF proteins was monitored by Western blotting using cell lysates (bottom). FIG. 2B, Colocalization of TREX and TRAF3 in mammalian cells. COS7 cells were transfected with myc-tagged TREX or TRAF3. Myc-tagged TREX (R-phycoerythrin, red) localized around nucleus as similar with TRAF3 (FITC, green).

FIG. 4. TREX upregulates NF-κB activity induced by TNFα-induced NF-κB activation in human embryonic kidney 293 cell. 293 human embryo kidney cells were maintained in MEM containing 10% FCS, 100 µg/ml penicillin G and 100 µg/ml streptomycin. For reporter assay, $10^6$ cells were seeded on 100 mm dishes and grown for 3 days in 5% $CO_2$ at 37° C. The cells were transfected with reporter DNA (luciferase) and either empty (pcDNA3.1(−)/MYC HIS) or mTREX expression plasmid (pcDNA3.1(−)/MYC HIS-m TREX) by the calcium phosphate precipitation method. After 12 h, the cells were treated with or without 20 ng/ml TNF-alpha. After an additional incubation for 12 h, the cells were washed with PBS and then the luciferase activities were determined by using Dual luciferase reporter assay system (Promega).

FIG. 5A shows the cohybridization to normal human metaphase spreads detected with avidin FITC (green signals). FIG. 5B shows the cohybridization to normal human prophase spreads detected with anti-digoxigenin-rhodamine (red signals).

FIGS. 7A-7B. FIG. 7A. Mouse TREX cDNA nucleotides 1-3479. (SEQ ID NO: 1); Mouse TREX cDNA Genbank Accession NO. AF083550. FIG. 7B. Mouse TREX cDNA nucleotides and the predicted amino acid sequence (SEQ ID NO: 2).

FIG. 8A-8B. FIG. 8A. Human TREX cDNA nucleotides 1-6172. (SEQ ID NO: 3); Human TREX cDNA Genbank Accession NO. AF083551. FIG. 8B. Human TREX cDNA nucleotides and the predicted amino acid sequence (SEQ ID NO: 4)

FIGS. 9A-9B. Sequence alignment of mouse and human EXTL3 proteins and expression of mouse EXTL3 and mRNA in various tissues. FIG. 9A. The amino acid sequence of mouse EXTL3 (AF083550) and human EXTL3 (AF083551) were aligned by using GENETYX-MAC 9.0 Identical residues are boxed, and a putative isoleucine zipper motif is shaded. FIG. 9B. Expression of the mouse EXTL3 gene on a commercial Northern blot (Clontech) of eight different tissues using a cDNA fragment as a probe. The various tissues are labeled at the top, and the size markers are indicated on the left. A transcript of about 6 kb is present in all tissues.

FIG. 10A. HEK293 cells were transfected with pcDNA or pcDNA/EXTL3. After 12 h, the cells were stimulated with or without 20 ng/ml TNF-α for 1 h. Then, nuclear extracts prepared from the cells were analyzed by using a electrophoretic mobility shift assay with NF-κB consensus oligonucleotide. FIG. 10B. The indicated amount of pcDNA/EXTL3 was cotransfected with 500 ng of the luciferase reporter plasmid pELAM-luc and 500 ng pRL-TK into HEK293 cells. The total amount of pcDNA constructs was adjusted to 10 µg by addition of empty vector. After 12 h, the cells were treated with or without 20 ng/ml TNF-α. At 12 h after stimulation, cell lysates were prepared and subjected to a dual luciferase assay. All values representing luciferase activities were normalized and are shown as the mean±SEM of trimplicate samples. FIG. 10C The indicated amount of pcDNA/EXTL3 and 5 µg of HA-tagged human TRAF2 construct were transfected with 500 ng of the luciferase reporter plasmid pELAM-luc and 500 ng pRL-TK into HEK293 cells. The total amount of pcDNA constructs was adjusted to 10 µg by adding an empty vector. After 24 h, cell lysates were prepared and subjected to the dual luciferase assay. All values representing luciferase activities were normalized and are shown as the mean±SEM of triplicate samples.

FIGS. 11A-11Da-11Dc. Effects of EXTL3 truncation mutants on NF-κB activity. FIG. 11A. Schematic representation of truncation mutants used in this assay. TM, trans-membrane region; EXT-C, EXT-COOH domain; EXT-N, EXT-NH₂ domain. FIG. 11B. A 10-µg aliquot of pcDNA/EXTL3, pcDNA/ΔN EXTL3, pcDNA/ΔC EXTL3, or pcDNA/ΔN&C EXTL3 was transfected with 500 ng pELAM-luc and 500 ng pRL-TK into HEK293 cells. After 12 h, the cells were treated with (hatched column) or without (open column) 20 ng/ml TNF-α. At 12 h after stimulation, cell lysates were prepared and subjected to the dual luciferase assay. All values representing luciferase activities were normalized and are shown as the mean±SEM of six samples. FIG. 11C. A 5 µg of pcDNA/EXTL3, pcDNA/ΔN EXTL3, pcDNA/ΔC EXTL3, or pcDNA/ΔN&C EXTL3 and 5 µg HA-tagged human TRAF2 construct (hatched column) or empty vector (open column) were transfected with 500 ng pELAM-luc and 500 ng pRL-TK into HEK293 cells. After 24 h, cell lysates were prepared and subjected to the dual luciferase assay. All values representing luciferase activities were normalized and are shown as the mean ±SEM of seven samples. FIG. 11D. HEK293 cells cultured on cover glasses were transfected with pEGFP-N2 (a), pEGFP/EXTL3 (b), or pEGFP/ΔN EXTL3 (c). After transfection, the cells were fixed with 3.7% formalin. Then, cells were treated with 0.2% Triton X-100. Fluorescence was imaged with a confocal laser scanning microscope. Bar, 50 µm.

FIGS. 12A-12H. Effects of TRAFs on EXTL3 distribution HEK293 cells cultured on cover glasses were transfected with EGFP-tagged EXTL3 construct and FLAG-tagged TRAF2 (FIGS. 12A-12D) or TRAF3 (E-H) constructs. After transfection, the cells were fixed with 3.7% formalin. Then, cells were treated with 0.2% Triton X-100. After blocking, indirect immuno-fluorescence analysis was performed. Monoclonal anti-FLAG antibody was used as a first antibody followed by a Cy-5-conjugated second antibody. TRITC-concanavalin A was used to reveal the endoplasmic reticulum region. Fluorescence was imaged with a confocal laser scanning microscope. EXTL3 is shown in green (FIGS. 12A, 12E). The concanavalin A-stained region is shown in red (FIGS. 12B, 12F). FIG. 12C shows TRAF2 in white, and FIG. 12G shows TRAF3 in white. FIG. 12D is a merged image of FIGS. 12A, 12B, and 12C, and FIG. 12H shows a merged image of FIGS. 12E, 12F, and 12G. Bar, 10 µm.

DETAILED DESCRIPTION OF THE INVENTION

Figure 1B:
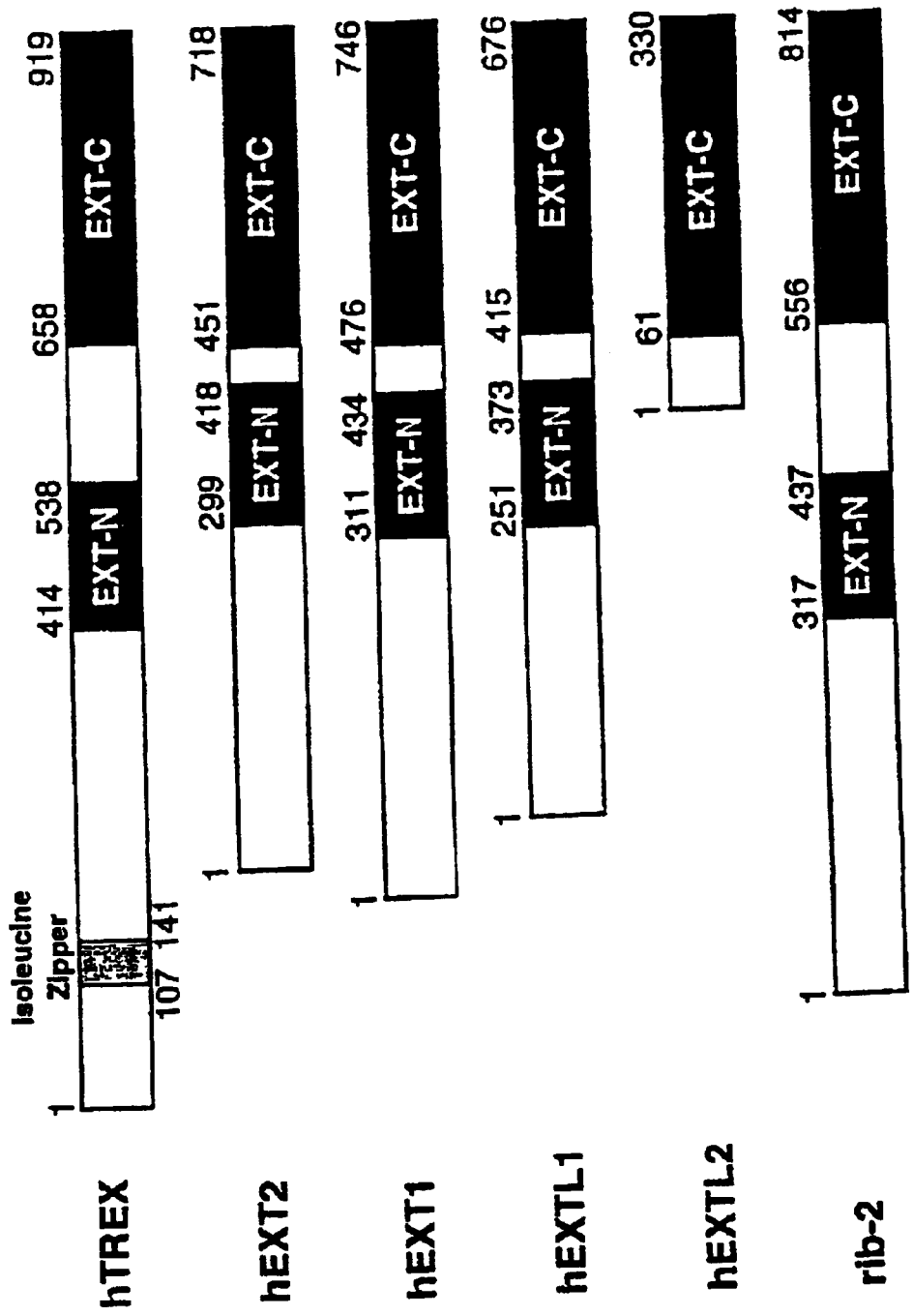

The following standard abbreviations are used throughout the specification to indicate specific nucleotides:

C=cytosine A=adenosine

T=thymidine G=guanosine

This invention provides an isolated nucleic acid molecule encoding a Tumor necrosis factor Receptor-Associated Factor (TRAF) protein-interacting hereditary multiple extoses (TREX) protein.

As used herein, tumor necrosis factor Receptor-Associated Factor (TRAF) protein-interacting hereditary multiple extoses protein (TREX) is a protein first identified as a potential tumor suppressor gene involved in tumor necrosis factor receptor (TNFR) superfamily. Furthermore, TREX is a signal modulator which bridges between TNFR and CD40-mediated signal transduction.

In an embodiment the above-described isolated nucleic acid molecule is a DNA molecule or a fragment thereof. In another embodiment the isolated DNA molecule is a cDNA molecule. In a further embodiment the DNA molecule is a genomic DNA molecule. In an embodiment the nucleic acid molecule is an RNA molecule. In another embodiment the nucleic acid molecule encodes a mammalian Tumor necrosis factor Receptor-Associated Factor (TRAF) protein-interacting hereditary multiple extoses (TREX) protein or a functionally active fragment thereof, e.g. a motif that interacts with TRAF proteins, including but not limited to motifs such as an isoleucine zipper motif and an EXT-C domain. In an embodiment the encoded mammalian Tumor necrosis factor Receptor-Associated Factor (TRAF) protein-interacting hereditary multiple extoses (TREX) protein is human Tumor necrosis factor Receptor-Associated Factor (TRAF) protein-interacting hereditary multiple extoses (TREX) protein.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, TREX, and as products for the large scale synthesis of the polypeptide (TREX) or fragments thereof (e.g. for the production of portions of the polypeptide encoding an isoleucine zipper motif, a hereditary multiple extoses C (EXT C) domain, or an isoleucine zipper motif and a hereditary multiple extoses C (EXT C) domain, portions which are involved in protein-protein interactions) by a variety of recombinant techniques. The molecule is useful for generating new cloning and expression vectors, transformed and transfected prokaryotic and eukaryotic host cells, and new and useful methods for cultured growth of such host cells capable of expression of the polypeptide (TREX) or portions thereof which comprise an isoleucine zipper motif and/or a hereditary multiple extoses C (EXT C) domain and related products.

In an embodiment the isolated nucleic acid molecule encoding the mammalian Tumor necrosis factor Receptor-Associated Factor (TRAF) protein-interacting hereditary multiple extoses (TREX) protein is a mouse, rat or human Tumor necrosis factor Receptor-Associated Factor (TRAF) protein-interacting hereditary multiple extoses (TREX) protein. In another embodiment the isolated nucleic acid molecule encodes a Tumor necrosis factor Receptor-Associated Factor (TRAF) protein-interacting hereditary multiple extoses (TREX) protein comprising an amino acid sequence as set forth in FIGS. 1 and 7B (SEQ ID NO: 2). In an embodiment the isolated nucleic acid molecule encodes a mouse TREX protein. In another embodiment the isolated nucleic acid molecule encodes a Tumor necrosis factor Receptor-Associated Factor (TRAF) protein-interacting hereditary multiple extoses (TREX) protein comprising an amino acid sequence as set forth in FIGS. 1 and 8B (SEQ ID NO: 4). In an embodiment the isolated nucleic acid molecule encodes a human TREX protein.

In an embodiment of the isolated nucleic acid molecule the encoded amino acid sequence comprises an isoleucine zipper motif and a hereditary multiple extoses C (EXT C) domain. In an embodiment the isolated nucleic acid is a fragment of the above-described nucleic acid, said fragment encoding an isoleucine zipper motif, a hereditary multiple extoses C (EXT C) domain, or an isoleucine zipper motif and a hereditary multiple extoses C (EXT C) domain. In another embodiment the Tumor necrosis factor Receptor-Associated Factor (TRAF) protein-interacting hereditary multiple extoses (TREX) protein has substantially the same amino acid sequence as set forth in FIGS. 1 and 7B (SEQ ID NO: 2). In a preferred embodiment the Tumor necrosis factor Receptor-Associated Factor (TRAF) protein-interacting hereditary multiple extoses (TREX) protein has substantially the same amino acid sequence as set forth in FIGS. 1 and 8B (SEQ ID NO: 4). In another embodiment the Tumor necrosis factor Receptor-Associated Factor (TRAF) protein-interacting hereditary multiple extoses (TREX) protein has the amino acid sequence as set forth in FIG. 1 and 7B (SEQ ID NO: 2). In preferred embodiment the Tumor necrosis factor Receptor-Associated Factor (TRAF) protein-interacting hereditary multiple extoses (TREX) protein has the amino acid sequence as set forth in FIG. 1 and 8B (SEQ ID NO: 4).

This invention provides an isolated nucleic acid molecule encoding a mutant homolog of the mammalian Tumor necrosis factor Receptor-Associated Factor (TRAF) protein-interacting hereditary multiple extoses (TREX) protein whose genetic alterations and resulting amino acid sequence(s) is set forth in Table 3, infra. In an embodiment the isolated nucleic acid molecule is a deletion mutant. In an embodiment of the deletion mutant the encoded mutant homolog comprises a tumor suppressor locus. In an embodiment of the deletion mutant the encoded mutant homolog does not comprise a tumor suppressor locus domain. In a further embodiment the above-described isolated nucleic acid molecule encoding the mammalian TREX protein comprises the genetic alterations and resulting amino acid sequence(s) as shown in Table 3, infra.

This invention provides a vector comprising the isolated nucleic acid molecule encoding a Tumor necrosis factor Receptor-Associated Factor (TRAF) protein-interacting hereditary multiple extoses (TREX) protein. In an embodiment the vector is adapted for expression in a host cell which comprises the regulatory elements necessary for expression of the nucleic acid molecule in the host cell operatively linked to the nucleic acid molecule encoding the Tumor necrosis factor Receptor-Associated Factor (TRAF) protein-interacting hereditary multiple extoses (TREX) protein so as to permit expression of the TREX protein. In another embodiment of the vector the host cell is a eukaryotic, bacterial, insect or yeast cell. In an embodiment of the vector the eukaryotic host cell is a mammalian cell. In a further embodiment the vector is a plasmid. In another embodiment of the vector comprising the nucleic acid encoding a Tumor necrosis factor Receptor-Associated Factor (TRAF) protein-interacting hereditary multiple extoses (TREX) protein the nucleic acid molecule is a DNA molecule. In an embodiment the DNA molecule is a cDNA molecule. In further embodiments, any of the above-described vectors are adapted for expression in a host cell which comprises the regulatory elements necessary for expression of the nucleic acid molecule in the host cell operatively linked to the nucleic acid molecule encoding the Tumor necrosis factor Receptor-Associated Factor (TRAF) protein-interacting hereditary multiple extoses (TREX) protein as to permit expression of the TREX protein. In an embodiment of the vector, the host cell is a eukaryotic, bacterial, insect or yeast cell. In another embodiment of the vector, the eukaryotic host cell is a mammalian cell. In a further embodiment of the vector is a plasmid.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells.

Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

One of ordinary skill in the art will easily obtain unique sequences from the cDNA cloned in plasmids. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in plasmids may further be used to screen other human tissue cDNA libraries to obtain isoforms of the nucleic acid sequences encoding TREX as well as to screen human genomic DNA to obtain the analogous nucleic acid sequences. The homologous nucleic acid sequences and isoforms may be used to produce the proteins encoded thereby.

This invention provides a method of producing a host cell operatively linked to the nucleic acid molecule encoding a Tumor necrosis factor Receptor-Associated Factor (TRAF) protein-interacting hereditary multiple extoses (TREX) protein, which comprises growing a host cell comprising any of the above-described vectors under suitable conditions permitting production of the TREX protein and recovering the TREX protein so produced. In an embodiment the method further comprising purifying the recovered TREX protein.

This invention provides a method of producing a polypeptide having the biological activity of a protein encoded by the nucleic acid molecule encoding a Tumor necrosis factor Receptor-Associated Factor (TRAF) protein-interacting hereditary multiple extoses (TREX) protein which comprises growing any of the above-described host cells under suitable conditions permitting production of the polypeptide and recovering the polypeptide so produced. In an embodiment the method further comprises purifying the recovered polypeptide.

This invention provides a purified mammalian Tumor necrosis factor Receptor-Associated Factor (TRAF) protein-interacting hereditary multiple extoses (TREX) protein. In an embodiment the purified mammalian Tumor necrosis factor Receptor-Associated Factor (TRAF) protein-interacting hereditary multiple extoses (TREX) protein is a human TREX protein.

Figures 1, 1E:
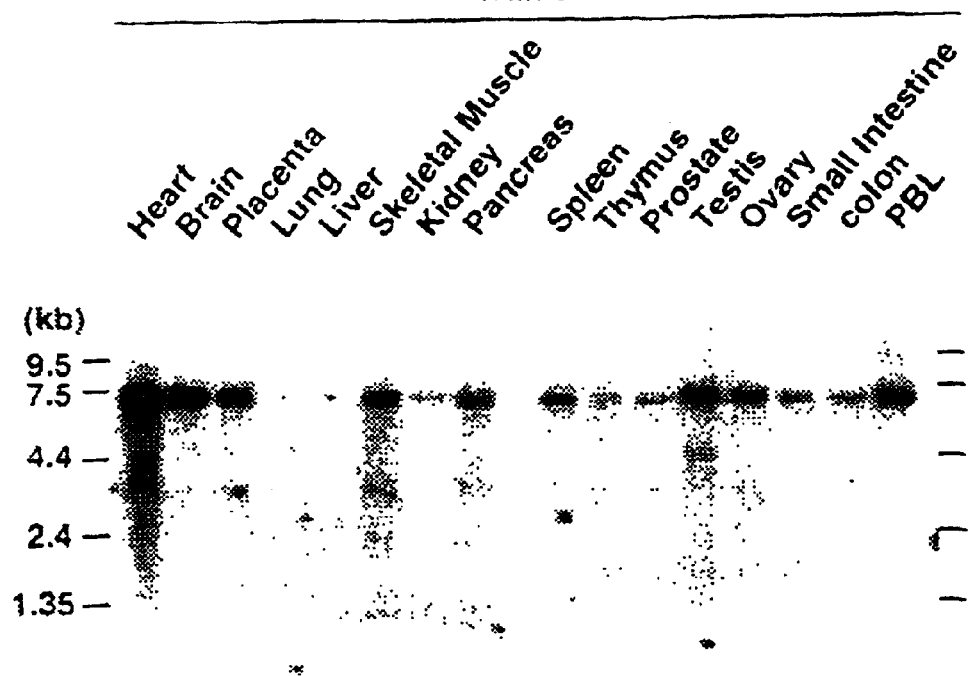

This invention provides a protein comprising substantially the amino acid sequence set forth in FIG. 1.

This invention provides an oligonucleotide comprising a nucleic acid molecule of at least 15 nucleotides capable of specifically hybridizing with a unique sequence included within the sequence of an isolated nucleic acid molecule encoding a Tumor necrosis factor Receptor-Associated Factor (TRAF) protein-interacting hereditary multiple extoses (TREX) protein. In an embodiment of the oligonucleotide the nucleic acid is DNA. In another embodiment of the oligonucleotide, the nucleic acid is RNA. In an embodiment the oligonucleotide comprises a nucleic acid molecule of at least 15 contiguous nucleotides capable of specifically hybridizing with a unique sequence included within the sequence of an isolated nucleic acid molecule encoding a Tumor necrosis factor Receptor-Associated Factor (TRAF) protein-interacting hereditary multiple extoses (TREX) protein.

This invention provides an antisense oligonucleotide comprising a sequence capable of specifically hybridizing with a unique sequence included within an mRNA molecule encoding a Tumor necrosis factor Receptor-Associated Factor (TRAF) protein-interacting hereditary multiple extoses (TREX) protein.

This invention provides an antisense oligonucleotide comprising a sequence capable of specifically hybridizing with a unique sequence included within a genomic DNA molecule encoding a Tumor necrosis factor Receptor-Associated Factor (TRAF) protein-interacting hereditary multiple extoses (TREX) protein.

This invention provides an antibody capable of binding to any of the above-described mammalian Tumor necrosis factor Receptor-Associated Factor (TRAF) protein-interacting hereditary multiple extoses (TREX) proteins. In an embodiment the antibody is a monoclonal antibody. In another embodiment the antibody is a polyclonal antibody.

This invention provides a monoclonal antibody directed to an epitope of a Tumor necrosis factor Receptor-Associated Factor (TRAF) protein-interacting hereditary multiple extoses (TREX) protein.

Polyclonal antibodies may be produced by injecting a host animal such as rabbit, rat, goat, mouse or other animal with the immunogen of this invention, e.g. a purified mammalian TREX or a purified human TREX. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual,* (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495-497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a method of inhibiting TREX protein interaction with a TRAF protein comprising administering a ligand comprising an amino acid domain which binds to a EXT C domain of the TREX protein so as to inhibit binding of the TREX protein to the TRAF protein. In an embodiment the TREX protein is a mammalian protein. In a preferred embodiment, the TREX protein is a human protein.

Inhibition of the TREX protein interaction with a TRAF protein may prevent TRAF induced NF-kB activation. Accordingly the above-described method may be used to control cell differentiation, cell proliferation, and apoptosis (programmed cell death). Accordingly, this method would be used to treat diseases such as cancer, autoimmune diseases and inflammation by inhibiting tumor cell growth and differentiation.

As used herein ligands comprising an amino acid domain which binds to a TREX protein, which binds to a TRAF binding domain, or which block TRAF binding are defined as an amino acid molecule or fragment thereof which has an amino acid sequence complementary to a TREX protein.

This invention provides a method of inhibiting overexpression of TREX protein comprising administering any of the above-described antisense oligonucleotides which bind to an mRNA molecule encoding a human Tumor necrosis factor Receptor-Associated Factor (TRAF) protein-interacting hereditary multiple extoses (TREX) protein so as to inhibit overexpression of the human TREX protein.

In an embodiment of the above-described method inhibiting overexpression of TREX protein thereby inhibits TRAF-induced CD40 signal dependent NF-kB activation. Accordingly the above-described method may be used to control cell differentiation, cell proliferation, and apoptosis (programmed cell death). Accordingly, this method would be used to treat diseases such as cancer, autoimmune diseases and inflammation by inhibiting tumor cell growth and differentiation.

In another embodiment of the above-described method the ligand is an antibody capable of binding to the TREX protein. In a further embodiment of the above-described method the antibody is a monoclonal or a polyclonal antibody.

This invention provides a method of inhibiting growth of a tumor cell comprising blocking a TRAF interacting site of a TREX protein by administering a ligand capable of binding to the TRAF interacting site of a TREX protein.

In an embodiment of the above-described method, the TRAF interacting site is a hereditary multiple extoses C (EXT C) domain. In another embodiment the tumor cell growth is inhibited in vivo or in vitro. In a further embodiment the ligand is an antibody capable of binding to the TRAF interacting site of a TREX protein. In still further embodiments the antibody is a monoclonal or a polyclonal antibody.

This invention provides a pharmaceutical composition comprising an amount of any of the above-described oligonucleotides effective to prevent overexpression of a TREX protein and a pharmaceutically acceptable carrier capable of passing through a cell membrane.

This invention provides a pharmaceutical composition comprising an amount of any of the above-described antibodies effective to block binding of a TREX protein to a TRAF protein and a pharmaceutically acceptable carrier capable of passing through a cell membrane.

This invention provides a method of administering the above-described pharmaceutical compositions comprising an amount of any of the above-described ligands, oligonucleotides or antibodies which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the above-described ligands, oligonucleotides or antibodies which are determined to be potentially therapeutic and a pharmaceutically acceptable carrier. In the subject invention an "effective amount" is any amount of the above-described ligands, oligonucleotides or antibodies which are determined to be potentially therapeutic, which, when administered to a subject suffering from a disease or abnormality against which the above-described ligands, oligonucleotides or antibodies which are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described ligands, oligonucleotides or antibodies which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described ligands, oligonucleotides or antibodies which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular ligands, oligonucleotides or antibodies in use, the strength of the preparation, the mode of administration, and the advancement of the disease condition or abnormality. Additional factors depending on the particular subject being treated will result in a need to adjust dosages, including subject age, weight, gender, diet, and time of administration.

This invention provides a method of treating an abnormality in a subject, wherein the abnormality is alleviated by the inhibition of binding of a TREX protein and a TRAF protein which comprises administering to the subject an effective amount of the above described pharmaceutical composition effective to block binding of the TREX protein and the TRAF protein in the subject, thereby treating the abnormality in the subject. In an embodiment the TRAF protein is TRAF2, TRAF3 or TRAF 5. In a preferred embodiment the abnormality is cancer, a hereditary multiple extosis or an autoimmune disease. In a further preferred embodiment the cancer is colon cancer, gastric cancer, human squamous cell carcinoma, prostate carcinoma, breast cancer, or papillary bladder cancer.

This invention provides a method of treating an abnormality in a subject, wherein the abnormality is alleviated by the inhibition of overexpression of a TREX protein which comprises administering to the subject an effective amount of the above-described pharmaceutical composition effective to inhibit overexpression of the TREX protein, thereby treating the abnormality in the subject. In a preferred embodiment the abnormality is cancer, a hereditary multiple extosis or an autoimmune disease. In a further preferred embodiment the cancer is colon cancer, gastric cancer, human head and neck squamous cell carcinoma, prostate carcinoma, breast cancer, thyroid cancer, esophageal cancer, lung cancer, colorectal cancer, ovarian cancer, papillary bladder cancer, osteosarcoma, chondrosarcoma, liposarcoma, giant cell tumor, Ewing sarcoma, and other malignant tumors.

This invention provides a method of screening for a chemical compound which inhibits TREX protein and TRAF protein binding comprising: (a) incubating the chemical compound with a TREX protein and a TRAF protein; (b) contacting the incubate of step (a) with an affinity medium under conditions so as to bind a TREX protein-TRAF protein complex, if such a complex forms; and (c) measuring the amount of the TREX protein-TRAF protein complex formed in step (b) so as to determine whether the compound is capable of interfering with the formation of the complex between the TREX protein-TRAF protein.

Additional methods for an assay to screen for drugs which inhibit the TREX-TRAF binding which are known to one of ordinary skill in the art include but are not limited to the two-hybrid screening system using yeast and mammalian cells (Fields, S. and O. Song, Nature, 340:245-246, 1989, the contents of which are hereby incorporated by reference).

In the above-described methods of screening for a chemical compound which inhibits TREX protein and TRAF protein binding association conditions, including but not limited to low salt, pH, or temperature may be used to compare the amount of TREX-TRAF complex formed without incubation with the compound.

In an embodiment the TRAF protein is TRAF2, TRAF3 or TRAF 5.

In a preferred embodiment the compound may be a CD40 receptor ligand or a CD40 antibody.

In a preferred embodiment of the above-described methods, the molecule is a peptide or a fragment thereof which comprises a TRAF binding domain. In further embodiments the TRAF protein is TRAF2, TRAF3 or TRAF 5.

This invention provides a method of preventing inhibition of activation of a CD40 signal-dependent NF-kB activation comprising administering any of the above-described antisense oligonucleotides which bind to an mRNA molecule encoding a human Tumor necrosis factor Receptor-Associated Factor (TRAF) protein-interacting hereditary multiple extoses (TREX) protein so as to prevent inhibition of activation of CD40 signal-dependent NF-kB activation.

This invention provides a method of preventing inhibition of activation of a CD40 signal-dependent NF-kB activation comprising administering a ligand comprising an amino acid domain which binds to a EXT C domain of the TREX protein so as to inhibit binding of the TREX protein to the TRAF protein, thereby preventing inhibition of activation of a CD40 signal-dependent NF-kB activation.

In a preferred embodiment of the above-described method the ligand is peptide or a fragment thereof which comprises a TRAF binding domain.

This invention provides a method of detecting a predisposition to cancer which comprises detecting of a genetic alteration in a nucleic acid encoding TREX protein in the sample from the subject. In a preferred embodiment of the above-described method the mutation is a silent point mutation or a missense point mutation. In another preferred embodiment of the above-described method the genetically altered nucleic acid encoding TREX protein is detected by contacting the nucleic acid from the sample with a TREX nucleic acid probe under conditions permitting the TREX nucleic acid probe to hybridize with the nucleic acid from the sample, thereby detecting the genetic alteration in the nucleic acid encoding TREX protein in the sample.

Methods of detecting genetic alterations in nucleic acid molecules are well known to one of ordinary skill in the art and include but are not limited to methods such as single strand conformation polymorphism detection, RNase protection assay, and PCR direct sequencing. As used herein, genetic alterations in nucleic acid molecules which may be detected include point mutations, deletions, translocations, and insertions.

In other preferred embodiments the cancer is colon cancer, gastric cancer, human head and neck squamous cell carcinoma, prostate carcinoma, breast cancer, thyroid cancer, esophageal cancer, lung cancer, colorectal cancer, ovarian cancer, papillary bladder cancer, osteosarcoma, chondrosarcoma, liposarcoma, giant cell tumor, Ewing sarcoma, and other malignant tumors. In another preferred embodiment of the above-described method the TREX nucleic acid probe comprises a nucleic acid molecule of at least 15 nucleotides which specifically hybridizes with a unique sequence included within the sequence of an isolated nucleic acid molecule encoding a Tumor necrosis factor Receptor-Associated Factor (TRAF) protein-interacting hereditary multiple extoses (TREX) protein. In an embodiment of the TREX nucleic acid probe the nucleic acid is DNA. In another embodiment of the TREX nucleic acid probe the nucleic acid is RNA.

This invention provides a TREX nucleic acid probe comprising a sequence capable of specifically hybridizing with a unique sequence included within the above-described isolated DNA molecule encoding a Tumor necrosis factor Receptor-Associated Factor (TRAF) protein-interacting hereditary multiple extoses (TREX) protein. In an embodiment the nucleic acid probe comprises a nucleic acid molecule of at least 15 contiguous nucleotides capable of specifically hybridizing with a unique sequence included within the sequence of the isolated nucleic acid molecule encoding a Tumor necrosis factor Receptor-Associated Factor (TRAF) protein-interacting hereditary multiple extoses (TREX) protein. In a further embodiment the TREX is mammalian protein. In an embodiment the mammalian TREX protein is mouse protein. In a preferred embodiment the mammalian TREX protein is human protein.

This invention provides a TREX nucleic acid probe comprising a sequence capable of specifically hybridizing with a unique sequence included within the above-described isolated mRNA molecule encoding a Tumor necrosis factor Receptor-Associated Factor (TRAF) protein-interacting hereditary multiple extoses (TREX) protein. In an embodiment the nucleic acid probe comprises a nucleic acid molecule of at least 15 contiguous nucleotides capable of specifically hybridizing with a unique sequence included within the sequence of the isolated nucleic acid molecule encoding a Tumor necrosis factor Receptor-Associated Factor (TRAF) protein-interacting hereditary multiple extoses (TREX) protein. In a further embodiment the TREX is mammalian protein. In an embodiment the mammalian TREX protein is mouse protein. In a preferred embodiment the mammalian TREX protein is human protein.

This invention provides a TREX nucleic acid probe comprising a sequence capable of specifically hybridizing with a unique sequence included within the above-described isolated genomic DNA molecule encoding a Tumor necrosis factor Receptor-Associated Factor (TRAF) protein-interacting hereditary multiple extoses (TREX) protein. In an embodiment of the method the mutation comprises a portion of a tumor suppressor locus. In an embodiment the nucleic acid probe comprises a nucleic acid molecule of at least 15 contiguous nucleotides capable of specifically hybridizing with a unique sequence included within the sequence of the isolated nucleic acid molecule encoding a Tumor necrosis factor Receptor-Associated Factor (TRAF) protein-interacting hereditary multiple extoses (TREX) protein. In a further embodiment the TREX is mammalian protein. In an embodiment the mammalian TREX protein is mouse protein. In a preferred embodiment the mammalian TREX protein is human protein.

This invention provides a method of diagnosing cancer in a subject which comprises: a) obtaining DNA from the sample of a subject suffering from cancer; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a genetically altered nucleic acid molecule encoding a TREX protein, wherein the nucleic acid is labeled with a detectable marker; e) detecting labeled bands which have hybridized to the nucleic acid probe in step (d), wherein the sequence of a genetically altered nucleic acid molecule encoding a TREX protein creates a unique band pattern specific to the DNA of subjects suffering from cancer; f) preparing DNA obtained from a sample of a subject for diagnosis by steps (a-e); and g) comparing the detected band pattern specific to the DNA obtained from a sample of subjects suffering from cancer from step (e) and the DNA obtained from a sample of the subject for diagnosis from step (f) to determine whether the patterns are the same or different and to diagnose thereby predisposition to cancer if the patterns are the same.

As used herein, genetic alterations in nucleic acid molecules which may be detected include point mutations, deletions, translocations, and insertions.

In an embodiment of the above-described method the size fractionation in step (c) is effected by a polyacrylamide or agarose gel. In another embodiment of the method the detectable marker is radioactive isotope, enzyme, dye, biotin, a fluorescent label or a chemiluminescent label. In a preferred embodiment of the above-described method, cancer associated with the expression of a mutated TREX protein is diagnosed. In further preferred embodiments of the above-described method the cancer is colon cancer, gastric cancer, human head and neck squamous cell carcinoma, prostate carcinoma, breast cancer, thyroid cancer, esophageal cancer, lung cancer, colorectal cancer, ovarian cancer, papillary bladder cancer, osteosarcoma, chondrosarcoma, liposarcoma, giant cell tumor, Ewing sarcoma, and other malignant tumors.

This invention provides a method of diagnosing cancer in a subject which comprises: a) obtaining RNA from the sample of the subject suffering from cancer; b) separating the RNA sample by size fractionation; c) contacting the resulting RNA species with a nucleic acid probe capable of specifically hybridizing with a unique sequence included within the sequence of a nucleic acid molecule encoding a mutated TREX protein, wherein the sequence of the nucleic acid molecule encoding the mutated TREX protein is labeled with a detectable marker; d) detecting labeled bands which have hybridized to the RNA species to create a unique band pattern specific to the RNA of subjects suffering from cancer; e) preparing RNA obtained from a sample of a subject for diagnosis by steps (a-d); and f) comparing the detected band pattern specific to the RNA obtained from a sample of subjects suffering from cancer from step (d) and the RNA obtained from a sample of the subject for diagnosis from step (f) to determine whether the patterns are the same or different and to diagnose thereby predisposition to cancer if the patterns are the same. In an embodiment of the method the size fractionation in step (c) is effected by a polyacrylamide or agarose gel. In another embodiment of the method the detectable marker is radioactive isotope, enzyme, dye, biotin, a fluorescent label or a chemiluminescent label. In a preferred embodiment of the above-described method, cancer associated with the expression of a mutated TREX protein is diagnosed. In further preferred embodiments of the above-described method the cancer is colon cancer, gastric cancer, human squamous cell carcinoma, prostate carcinoma, breast cancer, or papillary bladder cancer.

This invention will be better understood from the Experimental Details which follow. However, one skilled in the art will readily appreciate that the specific methods and results discussed are merely illustrative of the invention as described more fully in the claims which follow thereafter.

First Series of Experiments

Tumor necrosis factor (TNF) receptor-associated factor (TRAF) proteins contribute to signal transduction induced by TNF receptor family signaling. TRAF3 cloned as binding protein to the cytoplastic domain of CD40, a member of TNF receptor superfamily, is believed to be involved in signaling pathway induced by CD40, Lymphotoxin (LT) β receptor, CD30 ligation (1–7). Here molecular cloning of a novel TRAF-interacting protein named as TREX because of TRAF-interacting EXT (hereditary multiple exostoses) gene family protein is reported. TREX has a highly homologous sequence to the EXT gene family, a candidate of tumor suppressor gene (20-22). TREX strongly interacts with TRAF2 and TRAF3, and TREX and TRAF protein colocalize in mammalian cells. Moreover, overexpression of TREX inhibited NF-κB activity induced by TRAF-mediated signaling. These findings indicate that TREX and the other EXT gene family proteins can function as a mediator in receptor signaling and could be involved in tumorigenesis.

EXPERIMENTAL DETAILS

Methods and Materials

Two-hybrid Screening

Two-hybrid screening was performed in yeast L40 (MATa) strain cells with plasmid pBTM116 containing human TRAF3 (amino acids 82-543) subcloned in frame with the LexA as a bait and a mouse embryo cDNA library cloned into pVP16 as described previously (36). In order to obtain the clones containing cDNA encoding protein which binds specifically to TRAF3, clones that formed on histidine-deficient media and produced a blue reaction product with X-gal in filter assays (37) were cured of the LexA-TRAF3 plasmid by growing cells in tryptophan-containing medium, and then mated against a panel of yeast strains NA87-11A (MATα) containing plasmid pBTM116 that produce LexA fusion protein with lamin, Fas and CD40.

Mated cells were selected for growth in medium lacking tryptophan and leucine, and subsequently tested for the ability to trans-activate a lacZ reporter gene by growing cells on histidine-deficient media and a β-Gal colometric assay (37).

Northern Blot Analysis

Human and mouse Multiple Tissue Northern Blots (Clontech) were probed with human and mouse TREX cDNA, respectively.

Plasmid Construction and Transfection

Full length coding regions of TRAFs, TREX and their mutants were amplified by PCR and subcloned into FLAG-tagged pCR3.1 or myc-tagged pcDNA3.1 (Invitrogen). Mouse CD40 and CD40L were also amplified by PCR and subcloned into pMIKHygB. 293 cells and 293 T cells were transfected by standard calcium phosphate coprecipitation method. COS cells were transfected by use of FuGENE 6 (Boehringer Mannheim).

Production of Anti-TREX, Immunoprecipitation and Western Blot Analysis

Rabbit anti-TREX polyclonal antibody raised against a recombinant Glutathion S-transferase-fused mouse TREX protein. 293T cells ($2 \times 10^6$ cells) were transfected with the indicated plasmids. After transfection (40 hours), cell lysates were prepared in Lysis buffer (20 mM Tris (pH 7.6), 150 mM NaCl, 1% Triton X-100, 1 mM EDTA (pH 8.0), 10 μg/ml of aprotinin, 10 μg/ml of leupeptin, 5 mM Benzamidine and 1 mM PMSF) and incubated with indicated antibodies and 25 μl of 50% slurry of protein G-Sepharose. Immunoprecipitates were detected by Western blot analysis using the indicated antibody. To detect endogenous TREX protein, cell lysates of human colon carcinoma cell line KM12L4 were immunoprecipitated with anti-TREX antibody and detected by western blot analysis using anti-TREX antibody.

Immunohistochemistry

COS7 cells were transfected with TRAF3 or myc-tagged TREX. After transfection (40 hours), cells were fixed with methanol. For detection of TREX protein, Anti-myc antibody (9E10, BIOMOL) and Phycoerythrin-anti-mouse IgG (Chemicon) were used for 1st and 2nd antibody, respectively. For detection of TRAF protein, anti-TRAF3 antibody (Santa Cruz) and FITC-anti-rabbit IgG (Santa Cruz) were used for 1st and 2nd antibody, respectively.

Reporter Gene Assay 293 cells ($1 \times 10^6$ cells) were transfected with NF-κB-dependent reporter gene (pkBtkLuc), the indicated plasmids and pRL-CMV (Promega) for normalization of transfection efficiency as described previously (2). After transfection (40 hours), the cell lysates were prepared and luciferase activity measured using Dual-luciferase reporter assay system (Promega)

EXPERIMENTAL RESULTS AND DISCUSSION

TNF receptor-associated factor (TRAF) protein family members have been reported to contribute to TNF receptor-initiated signaling through direct binding to the cytoplasmic region of receptors, resulting in the activation of many signaling molecules such as transcription factor NF-κB, mitogen-activated protein kinase (MAPK), although TRAF1 and TRAF4 have not been implicated clearly (2, 8-13). Overexpression of TRAF2 activates NF-kB and JNK/SAPK via NF-κB-inducing kinase (NIK)-dependent pathway and -independent pathway, respectively (14-16). TRAF5 activates NF-κB and TRAF6 activates NF-κB and ERK/MAPK pathway (2, 9-12). Although TRAF2 is implicated to be required for protection against TNF-induced apoptosis via NF-κB-independent pathway (17, 18), TRAF5 or TRAF6 could act to activate NF-κB pathway in place of TRAF2. These observations suggest that action of TRAF proteins seem to be regulated properly in response to each receptor signaling for the expression of receptor functions. On the other hand, overexpression of TRAF3 has been demonstrated to suppress the activation of NF-κB and ERK/MAPK induced by CD40 crosslinking (2, 8). TRAF3 is implicated to be required for postnatal development and T-dependent immune responses (19), but no plausible signaling pathways or molecules via TRAF3 which lead to explain these biological functions were reported so far, in turn, the specificity and function of TRAF3-mediated signaling are still unclear.

Analyzing the signaling molecules downstream of TRAF3 would provide an understanding of the function of TRAF3 and its specificity. To identify the signaling molecules which specifically bind to TRAF3, two-hybrid screening of a mouse embryo cDNA library was performed using TRAF3 (amino acids 82-543) as a bait. In this screening, multiple cDNA clones encoding several kinds of proteins were identified by sequencing. One clone among these positive clones, showed a putative isoleucine zipper motif in its sequence (FIG. 1a). On the basis of a partial sequence, marathon PCR amplification and 5'-RACE methods were carried out, and a mouse full length sequence with an open reading frame of 2,757 bp, which encodes a 918 amino acid peptide, was obtained (FIG. 1a). Human full length cDNA with an open reading frame of 2,760 bp, which encodes a 919 amino acid peptide with 96.8% identity to the mouse sequence, was also identified by screening of a human fetal brain cDNA library and the 5'-RACE method (FIG. 1a). A BLAST data base search revealed that the C-terminal region of these clones shows significant homology to hereditary multiple exostoses (EXT) gene family proteins such as EXT1, EXT2, EXTL1, EXTL2 and C. elegans rib-2 (FIG. 1b) (20-25). Therefore, this new gene was designated as TREX (for TRAF-interacting EXT gene family protein). Based on homology searches among EXT family proteins including TREX, permitted designating the highly homologous C-terminal regions as EXT domains, which are divided into two domains, EXT-N and EXT-C domains (FIG. 1c, d). These new conserved regions might function as signaling mediators by protein-protein interaction. Surprisingly, human and mouse TREX have significant homology to C. elegans rib-2 (FIG. 1c, d) in not only the EXT domain but the region between the EXT-N and the EXT-C domains (33%, data not shown). This observation suggests that TREX protein plays a critical role in development beyond species.

Figures 1, 1E, 2:
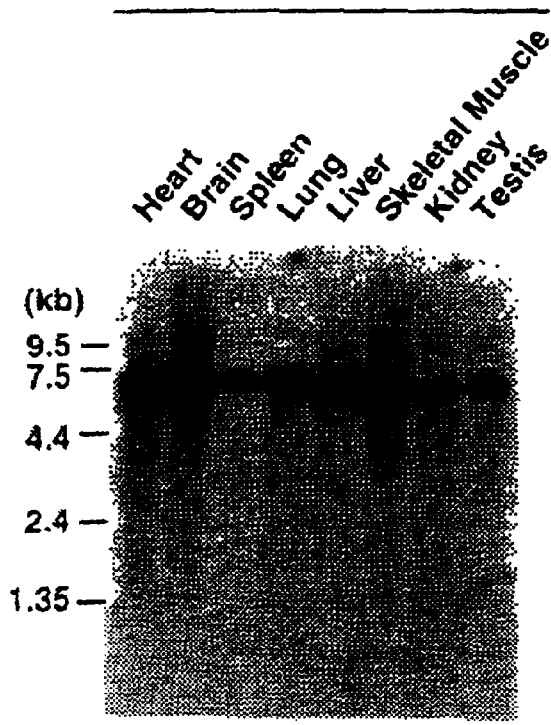
Figure 1F:
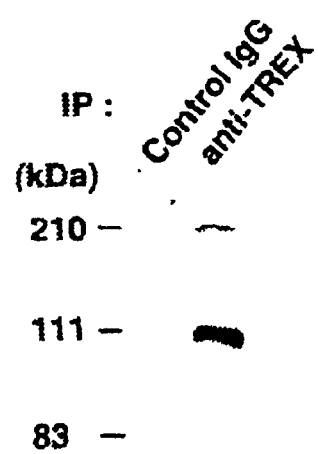

Next the expression of TREX mRNA and protein was examined. Northern blot analysis revealed about 7.0 kilobases transcript of TREX expressed in various tissues, with high expression in brain, heart, skeletal muscle (FIG. 1e). To examine the endogenous TREX protein in mammalian cells, cell lysates of human colon carcinoma cell line KM12L4 were immunoprecipitated with either a normal rabbit IgG or a rabbit anti-TREX antibody. Anti-TREX antibody detected a specific band at about 107 kDa, which is consistent with the predicted molecular weight of full length TREX (FIG. 1f).

As TREX has cloned as TRAF3-binding protein, the binding specificity to TRAF family proteins was examined. The 293T cells were transfected with TREX and TRAF expression plasmids. Coimmunoprecipitation experiments indicated that not only TRAF3 but also TRAF2 strongly and TRAF5 weakly binds to TREX (FIG. 2a). This observation leads to the consideration that TRAF proteins interact with TREX through TRAF domain, which is comparatively conserved among TRAF proteins, and that TREX and TRAF protein should colocalize in the cells. To examine the localization of TREX protein and TRAF3 protein, COS7 cells were transfected with TREX or TRAF3 expression plasmids. TRAF3 protein localized in cytoplasm, especially the region outside of the nuclear membrane, and TREX also localized around the nuclear membrane (FIG. 2b). These results suggest that TREX and TRAF proteins are physically associated in mammalian cells.

Figure 3:
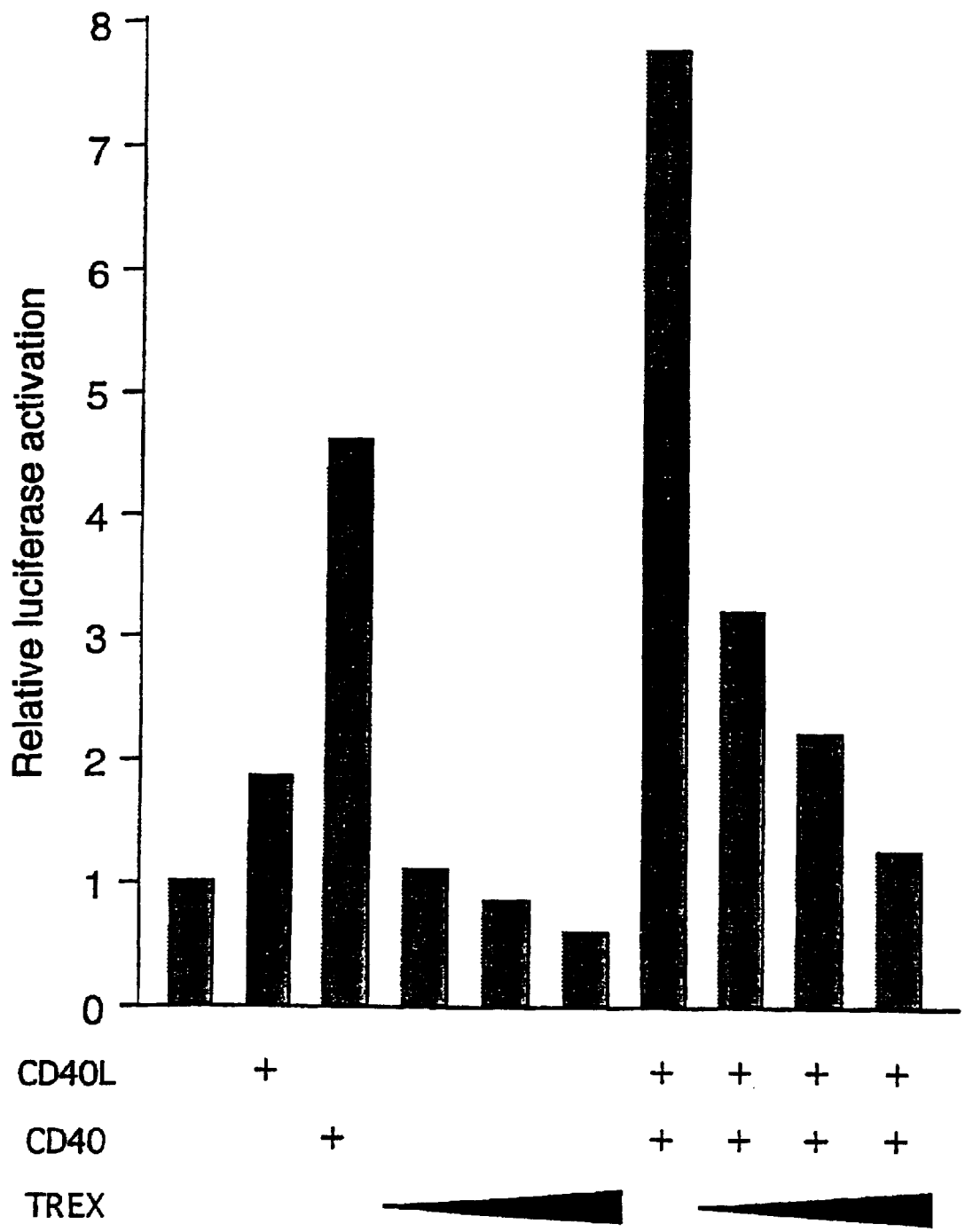
FIG. 3. TREX modulates NF-κB activity induced by TRAF-mediated signaling pathway. 293 cells were transiently transfected with NF-κB-dependent reporter gene together with several amounts of TREX in the presence of CD40 and CD40 ligand (a) or TRAF2 (b). Luciferase activities were determined and normalized by co-transfection of pRL-CMV using dual-luciferase assay kit (Promega).

The interaction of TREX and TRAF2 or TRAF3 indicated that TREX could be involved in TRAF-mediated signaling. Therefore, whether the expression of TREX protein could affect NF-kB activation induced by several stimulation was tested. 293 cells were transfected with TREX with CD40 and CD40 ligand in the presence of a NF-KB-specific reporter gene. As shown in FIG. 3, CD40 signal-dependent NF-κB activation was inhibited by overexpression of TREX in a dose dependent manner, indicating that TREX could contribute to NF-κB pathway induced by CD40 ligation. Next, applicant examined whether TREX is involved in NF-κB activation mediated TRAF2 or not.

Overexpression of TREX upregulated TRAF2-induced NF-κB activation (FIG. 4). These results suggest that TREX acts as a negative regulator of NF-κB pathway by direct interaction with TRAF2 in TNF receptor type II signaling. TRAF-interacting proteins TANK/I-TRAF and TRIP proteins, which inhibit NF-κB activity induced by TNF receptor family stimulation, were cloned by two-hybrid screening (26-28). TRIP protein was proposed to be regulated by switching with antiapoptotic protein such as c-IAP in response to the signals leading to cell activation or cell death (26). However, as the biological function of these proteins in TRAF-mediated signaling is still unknown, it is important to further analyze the activity of several signaling molecules.

Demonstrated here is the identification of a novel TRAF-interacting protein, TREX, and the contribution of TREX protein in CD40/TNF receptor type II signaling mediated by TRAF family. Furthermore, the sequence of this new protein TREX revealed a high homology to the EXT gene family and novel domains named EXT-N and EXT-C domains. This conserved sequence in the EXT domain suggests that the EXT domain might contribute to protein-protein interaction. Whether the EXT domain of the other EXT gene family proteins is involved in protein-protein interaction or not is now under investigation.

EXT gene family proteins, EXT1 and EXT2 have been cloned by positional cloning on the basis of linkage analysis in informative exostoses families (20-22). Some mutation was found in these genes, suggesting these genes should be candidate genes responsible for EXT (20-22, 29-31). Three loci have been localized. The EXT1 and EXT2 were localized on chromosome 8q24.1, 11p11-13, respectively (20, 32, 33), and the third gene EXT3 on 19p was not identified (34). Also identified was the chromosomal localization of human TREX on chromosome 8p11-12 (Shao et al., submitted), excluding TREX as a candidate gene for EXT3. It is important to investigate whether TREX could be responsive to EXT or EXT-related diseases. EXT family protein has been suggested to be a tumor suppressor gene because previous reports showed that multiple mutation in chondrosarcoma from sporadic tumors and tumors derived from malignant degeneration of exostoses (31, 35). Also identified was some infrequent mutation in TREX gene in some tumors (Shao et al., submitted), suggesting TREX might contribute to prevention of abnormal development such as transformation and tumorigenesis. The mutation of TREX gene in many kinds of tumor samples is being surveyed.

Not only mammals but also species such as C. elegans which lack bone in their body have homologous genes to the EXT gene family according to EST database search (25), suggesting that the EXT family proteins play an important role in development except bone development. A TREX-knockout mouse and rib-2-knockout C. elegans are being made. Knockout of EXT gene family genes in these species will facilitate an understanding of their function and their importance during development.

Five EXT gene family proteins were identified but the function of these gene products has been unknown. In this study, it is shown for the first time that an EXT family protein, TREX, acts as a signaling molecule mediating TNF receptor superfamily (FIGS. 3, 4). Also shown is that the EXT-domain of TREX interacts with TRAF proteins, which mediate receptor signaling through direct binding. These findings imply that the other EXT proteins could act as signaling mediators in receptor signaling. As TREX and the other EXT family proteins are easily thought to be involved in receptor signaling, the development of inhibitor(s) of signaling cascades related to TREX or the other EXT family proteins will be used to design drugs to treat many diseases including cancer.

References for the First Series of Experiments

1. Gedrich, R. W., Gilfillan, M. C., Duckett, C. S., Van Dongen, J. L. & Thompson, C. B. CD30 contains two binding sites with different specificities for members of the tumor necrosis factor receptor-associated factor family of signal transducing proteins. *J Biol Chem* 271, 12852 (1996).
2. Kashiwada, M., et al. Tumor necrosis factor receptor-associated factor 6 (TRAF6) stimulates extracellular signal-regulated kinase (ERK) activity in CD40 signaling along a ras-independent pathway. *J Exp Med* 187, 237 (1998).
3. VanArsdale, T. L. et al. Lymphotoxin-beta receptor signaling complex: role of tumor necrosis factor receptor-associated factor 3 recruitment in cell death and activation of nuclear factor kappaB. *Proc Natl Acad Sci USA* 94, 2460 (1997).
4. Force, W. R., Cheung, T. C. & Ware, C. F. Dominant negative mutants of TRAF3 reveal an important role for the coiled coil domains in cell death signaling by the lymphotoxin-beta receptor. *J Biol Chem* 272, 30835 (1997).
5. Hu, H. M., O'Rourke, K., Boguski, M. S. & Dixit, V. M. A novel RING finger protein interacts with the cytoplasmic domain of CD40. *J Biol Chem* 269, 30069 (1994).
6. Sato, T., Irie, S. & Reed, J. C. A novel member of the TRAF family of putative signal transducing proteins binds to the cytosolic domain of CD40. *Febs Lett* 358, 113 (1995).
7. Cheng, G. et al. Involvement of CRAF1, a relative of TRAF, in CD40 signaling. *Science* 267, 1494 (1995).
8. Rothe, M., Sarma, V., Dixit, V. M. & Goeddel, D. V. TRAF2-mediated activation of NF-kappa B by TNF receptor 2 and CD40. *Science* 269, 1424 (1995).
9. Ishida, T. K. et al. TRAF5, a novel tumor necrosis factor receptor-associated factor family protein, mediates CD40 signaling. *Proc Natl Acad Sci USA* 93, 9437 (1996).
10. Ishida, T. et al. Identification of TRAF6, a novel tumor necrosis factor receptor-associated factor protein that mediates signaling from an amino-terminal domain of the CD40 cytoplasmic region. *J Biol Chem* 271, 28745 (1996).

11. Nakano, H., et al. TRAF5, an activator of NF-kappaB and putative signal transducer for the lympho-toxin-beta receptor. *J Biol Chem* 271, 14661 (1996).
12. Cao, Z., Xiong, J., Takeuchi, M., Kurama, T. & Goeddel, D. V. TRAF6 is a signal transducer for interleukin-1. *Nature* 383, 443 (1996).
13. Regnier, C. H., et al. Presence of a new conserved domain in CART1, a novel member of the tumor necrosis factor receptor-associated protein family, which is expressed in breast carcinoma. *J Biol Chem* 270, 25715 (1995).
14. Song, H. Y., Regnier, C. H., Kirschning, C. J., Goeddel, D. V. & Rothe, M. Tumor necrosis factor (TNF)-mediated kinase cascades: bifurcation of nuclear factor-kappaB and c-jun N-terminal kinase (JNK/SAPK) pathways at TNF receptor-associated factor 2. *Proc Natl Acad Sci USA* 94, 9792 (1997).
15. Natoli, G., et al. Tumor necrosis factor (TNF) receptor 1 signaling downstream of TNF receptor-associated factor 2. Nuclear factor kappaB (NFkappaB)-inducing kinase requirement for activation of activating protein 1 and NFkappaB but not of c-Jun N-terminal kinase/stress-activated protein kinase. *J Biol Chem* 272, 26079 (1997).
16. Malinin, N. L., Boldin, M. P., Kovalenko, A. V. & Wallach, D. MAP3K-related kinase involved in NF-kappaB induction by TNF, CD95 and IL-1. *Nature* 385, 540 (1997).
17. Yeh, W. C., et al. Early lethality, functional NF-kappaB activation, and increased sensitivity to TNF-induced cell death in TRAF2-deficient mice. *Immunity* 7, 715 (1997).
18. Lee, S. Y., et al. TRAF2 is essential for JNK but not NF-kappaB activation and regulates lymphocyte proliferation and survival. *Immunity* 7, 703 (1997).
19. Xu, Y., Cheng, G. & Baltimore, D. Targeted disruption of TRAF3 leads to postnatal lethality and defective T-dependent immune responses. *Immunity* 5, 407 (1996).
20. Ahn, J., et al. Cloning of the putative tumour suppressor gene for hereditary multiple exostoses (EXT1). *Nat Genet* 11, 137 (1995).
21. Wuyts, W., et al. Positional cloning of a gene involved in hereditary multiple exostoses. *Hum Mol Genet* 5, 1547 (1996).
22. Stickens, D., et al. The EXT2 multiple exostoses gene defines a family of putative tumour suppressor genes. *Nat Genet* 14, 25 (1996).
23. Wuyts, W., et al. Identification and characterization of a novel member of the EXT gene family, EXTL2 [In Process Citation]. *Eur J Hum Genet* 5 382 (1997).
24. Wise, C. A., Clines, G. A., Massa, H., Trask, B. J. & Lovett, M. Identification and localization of the gene for EXTL, a third member of the multiple exostoses gene family. *Genome Res* 7, 10 (1997).
25. Clines, G. A., Ashley, J. A., Shah, S. & Lovett, M. The structure of the human multiple exostoses 2 gene and characterization of homologs in mouse and *Caenorhabditis elegans* [letter]. *Genome Res* 7, 359 (1997).
26. Lee, S. Y., Lee, S. Y. & Choi, Y. TRAF-interacting protein (TRIP): a novel component of the tumor necrosis factor receptor (TNFR)- and CD30-TRAF signaling complexes that inhibits TRAF2-mediated NF-kappaB activation. *J Exp Med* 185, 1275 (1997).
27. Cheng, G. & Baltimore, D. TANK, a co-inducer with TRAF2 of TNF- and CD 40L-mediated NF-kappaB activation. *Genes Dev* 10, 963 (1996).
28. Rothe, M., et al. I-TRAF is a novel TRAF-interacting protein that regulates TRAF-mediated signal transduction. *Proc Natl Acad Sci USA* 93, 8241 (1996).
29. Wuyts, W., et al. Mutations in the EXT1 and EXT2 Genes in Hereditary Multiple Exostoses. *Am J Hum Genet* 62, 346 (1998).
30. Wells, D. E. et al. Identification of novel mutations in the human EXT1 tumor suppressor gene. *Hum Genet* 99, 612 (1997).
31. Hecht, J. T., et al. Hereditary multiple exostoses (EXT): mutational studies of familial EXT1 cases and EXT-associated malignancies. *Am J Hum Genet* 60, 80 (1997).
32. Wu, Y. Q., et al. Assignment of a second locus for multiple exostoses to the pericentromeric region of chromosome 11. *Hum Mol Genet* 3, 167 (1994).
33. Wuyts, W., et al. Refinement of the multiple exostoses locus (EXT2) to a 3-cM interval on chromosome 11. *Am J Hum Genet* 57, 382 (1995).
34. Le Merrer, M., et al. A gene for hereditary multiple exostoses maps to chromosome 19p. *Hum Mol Genet* 3, 717 (1994).
35. Hecht, J. T., et al. Hereditary multiple exostosis and chondrosarcoma: linkage to chromosome II and loss of heterozygosity for EXT-linked markers on chromosomes II and 8. *Am J Hum Genet* 56, 1125 (1995).
36. Sato, T., Irie, S., Kitada, S. & Reed, J. C. FAP-1: a protein tyrosine phosphatase that associates with Fas. *Science* 268, 411 (1995).
37. Sato, T., et al. Interactions among members of the Bcl-2 protein family analyzed with a yeast two-hybrid system [published erratum appears in Proc Natl Acad Sci USA 1995 Feb 28;92(5):2016]. *Proc Natl Acad Sci USA* 91, 9238 (1994).

Second Series of Experiments

Hereditary multiple exostoses (EXT) is an autosomal dominant disorder characterized by short stature and the development of multiple bone tumour (1-3). Three genetic loci have been identified by genetic linkage analysis at chromosome 8q24.1 (EXT1) (4), 11p11-13 (EXT2) (5) and 19p (EXT3) (6). The putative tumour suppressor gene EXT1 and EXT2 were identified and characterized (7,8). Recently, two EXT-like genes, EXTL1 (9) and EXTL2 (10) have also been identified. EXTL1 and EXTL2 were mapped to chromosome 1p36.1 and 1p11-12, respectively, a region that frequently deleted in various tumour types. Previously reported was the isolation of a novel member of EXT gene family, designated TREX from mouse (11). Reported here is the isolation of TREX from human and located it at chromosome 8p11-12 by fluorescence in situ hybridization, a region that also frequently deleted in various tumours. In preliminary screens, TREX alterations were observed in some human cancers. This gene, TREX, therefore, may be a novel member of EXT gene family and may be a potential candidate which appears to be associated with the oncogenesis of multiple human genes.

Hereditary multiple exostoses (EXT) is an inherited multiple disorder characterized by the presence of exostoses, bony outgrowth capped by cartilage and with the most serious complication of chondrosarcomas or osteosarcomas (1-3). EXT1 and EXT2 were cloned (7, 8) and shown to harbor mutations in affected members of multiple exostoses families, defining two candidates as the genes responsible for multigene family of proteins with potential tumour suppressor activity. Recently, another two members of EXT-like genes, EXTL1 and EXTL2 were also identified (9, 10). Both genes were mapped to the short arm of chromosome 1, in bands 1p36 and 1p11-12, respectively, a region that frequently loss of heterozygosity in breast (12-13), gastric cancer (14), colorectal polyps (15), multiple endocrine neoplasia (16), and cervical carcinoma (17). Nevertheless, chromosome localization of EXT1 and EXTL2 exclude them as candidates for EXT3. However, EXT1 and EXTL2 may play a role in those cases of multiple exostoses that cannot be linked to chromosome 8, 11 or 19. It is also possible that EXTLs might function as tumor suppressors in an entirely different cell type, due to their striking difference of chromosome locations. Therefore, searching for additional members of EXTL gene family in man and other species will be very important.

A novel member of multiple exostoses gene family was previously isolated and characterized by yeast-two hybrid approaches from mouse, which is also a novel component of TRAF signal complex, named mTREX (mouse TRAF-interaction EXT protein) (11). To identify potential coding sequences of human TREX, a 500 bp of mouse cDNA which does not show homology to EXT gene family was used to screen a human adult brain cDNA library (Clontech) at low stringency condition, two overlapping positive clones were identified. Clone 1, contains an insert size of 1614 bp with a partial open reading frame of 1590 (530 amino acids) followed by a stop codon and a 24 bp 3'-untranslated region. Clone 2 contains an insert size of 1430 bp with 118 bp overlapping with Clone 1 at the 3'-untranslated region, resulting in 2926 bp of the total cDNA sequence. This cDNA sequence was used to search the GenBank using BLAST search program and demonstrated a near identity and overlapping with human chromosome 8 BAC clone CIT987SK-2A8 (HSU96629, NCBI sequence ID g2341008, briefly as BAC 8). This clone was obtained and a complete sequence determined. To obtain cDNA covering additional portions of the gene a PCR-based method was used. Primers were designed from the sequence of BAC 8. PCR of a randomly primed, Jurkat total RNA with these primers produced multiple, specific bands of different sizes, which were individually cloned to yield the cDNA clones. The longest clone contains a 1197 bp insert. Sequencing revealed that this clone overlapped with the cDNA clone 1 from brain cDNA library by 51 nucleotides at the 5' direction. To extend the hTREX to a full-length cDNA sequence, a modification of the 3' and 5'-rapid amplifications of cDNA ends (RACE) were performed, producing a series of overlapping RACE products which extended the cDNA sequence 637 base pairs in the 5' direction and 1527 bp in the 3' direction. The combination of cDNA isolation from cDNA library, PCR extension and RACE extension resulted in the complete sequence of the hTREX candidate gene of 6236 bp. The whole cDNA sequence was sent to GenBank (the accession number is AF083551 for human TREX). The longest continuous coding region is 2760 bp starting at nucleotide 638, and is preceded by 6 in frame stop codons upstream. The predicted 5' and 3'-untranslated region (UTR) is unusually long as compared with the 5' and 3' UTR sequences which have been found in some proto-oncogenes as well as human transforming growth factor-s (18).

Figure 5B:
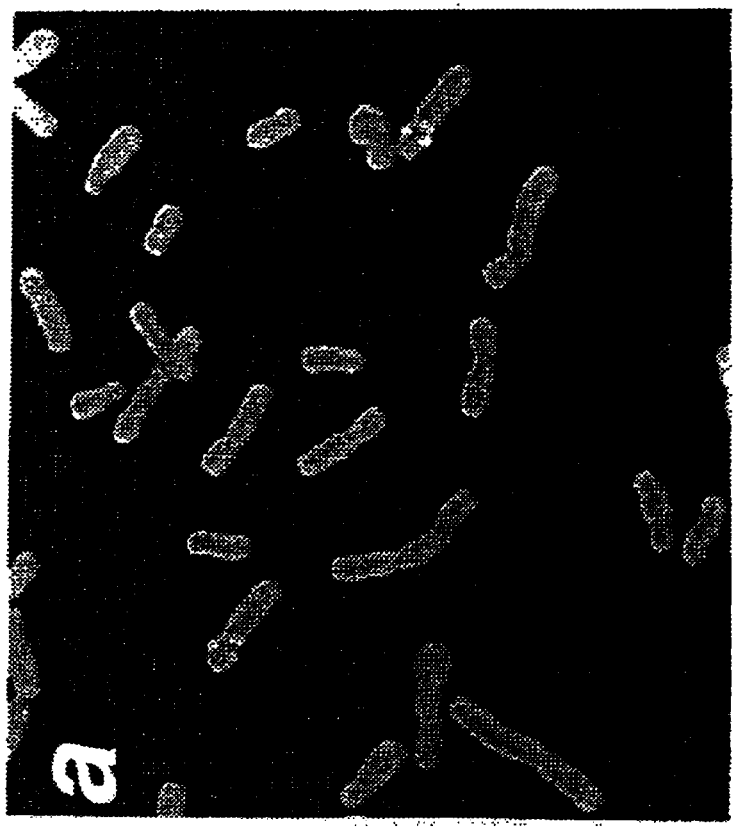
FIGS. 5A–5B. Chromosomal mapping of the TREX gene on chromosome 8p12-p21. The biotin-labeled TREX cDNA probe and the digoxigenin-labeled chromosome 8 centromere-specific probe were cohybridized and detected. Chromosomes were counterstained with DAPI (blue).
Figure 5A:
Figure 6:
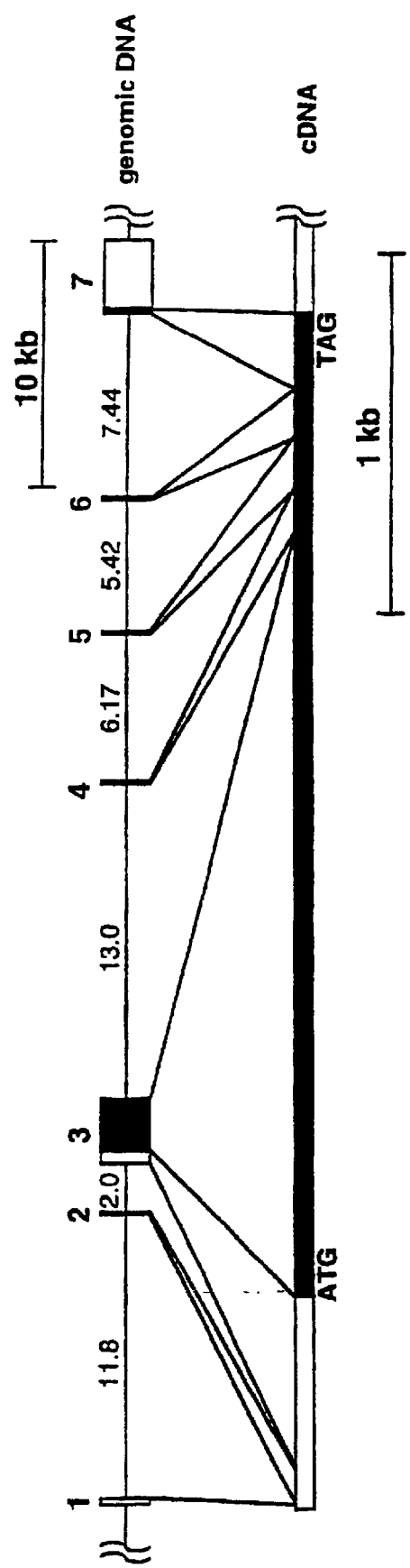
FIG. 6. Genomic organization of TREX gene. Exon-intron distribution is shown in upper panel. The 7 exons are indicated by box and numbered. The size of intron is also indicated in kilobases. The middle panel represents the TREX cDNA with translation initiation site (ATG) and termination site (TAG). Closed box and open box in these represent the coding region and non-coding region, respectively.

The cDNA sequence is identical to BAC 8 which had previously been mapped to chromosome 8p. To further determine the finest chromosome location of TREX, cDNA clone containing the whole open reading frame was purified and hybridized to metaphase chromosome spreads using fluorescence in situ hybridization (FISH). This analysis positioned TREX on chromosome 8p11-12 (FIG. 5), a region of the genome is frequently deleted in tumors from human squamous cell carcinomas of the head and neck (SCCHN) (19), prostate carcinomas (20), breast cancers (21), papillary bladder cancers (22) and colon cancers (23), and is thus believed to contain one or more tumor suppressor loci.

To further characterize the hTREX gene and to determine the intron/exon boundaries for mutational analysis, hTREX sequences were compared to BAC 8 genomic sequences. The TREX gene totally consists of 7 exons. The exact intron and exon sizes have been determined. All exon-intron splice junctions conform to the eukaryotic 5'-donor and 3'-acceptor consensus splice junction sequence GT-AG (24) (Table 1). Of the 6 splice junctions, 3 occurred between codons, and 3 interrupted codons.

TABLE 1

The sizes and junction sequences for exon/introns of hTREX

| | Size (bp) | | Sequences at exon-intron junction | |
|---|---|---|---|---|
| No. | Exon | Intron | 3' splicing acceptor | 5' splicing donor |
| 1 | 71 | 11800 | | AGCCGgtaggac |
| 2 | 94 | 2033 | aaatcagGAGAG | ACATGgtgagga |
| 3 | 2623 | 13035 | tttgcagGCCTG | TCATGgtaatag |
| 4 | 128 | 6167 | atacaagGTGGT | TTCCGgtgagag |
| 5 | 145 | 5421 | tttcaagGGTGT | ACAAGgtaagaa |
| 6 | 129 | 7433 | ctgacagTATTA | TCAAGgtgaggt |
| 7 | 3029 | | tttccagGTGAC | |

The fact that the TREX candidate gene showed significant similarity with EXT gene family and mapped within the region deleted in a variety of tumor types, strongly suggests that it is therefore a novel member of the EXT gene family as well as a potential candidate for several tumor phenotypes. To facilitate the search for mutations of whole open reading form of TREX, 5 sets of primer pairs for PCR amplification and 12 sequencing primers were selected from the flanking intronic or extronic sequences (Table 2).

TABLE 2

Primers for PCR amplification and Sequencing of human TREX

| Exon 3 | 5' forward primer | 5' TTATGGCGAGTGACCCGACGTG 3' |
|---|---|---|
| | 3' reverse primer | 5' TTGCTAAAGTGAAGGAAGTTGG 3' |
| | sequencing primers (forward) | 5' ACCCGACGTGATCTGG 3' |
| | | 5' AAGAGCTCCTGCAGCTGG |
| | | 5' TTCTCGTTGCCCTCTCAC 3' |
| | | 5' ATCATCAATCTGTCACG 3' |
| | | 5' ACTACGATGACCGGATC 3' |
| | | 5' TTCCCTACCAGGACATGC 3' |
| | | 5' AACATGGCTGACAACG 3' |
| | | 5' TATTGGTGGTGGAGCTGG 3' |
| Exon 4 | 5' forward primer | 5' AATCCAGCCATGGTCTCCTTGG 3' |
| | 3' reverse primer | 5' AGTCGATGCCATTATTACCAGC 3' |
| | sequencing primers (forward) | 5' TTCCTTCCTCATCACAG 3' |
| Exon 5 | 5' forward primer | 5' AGGTCTGTGTATGCACTTGTG 3' |
| | 3' reverse primer | 5' AGTCGATGCCATTATTACCAGC 3' |
| | sequencing | 5' TTCAAGGGTGTGGAGAG 3' |

TABLE 2-continued

Primers for PCR amplification and Sequencing of human TREX

|  | primers (forward) |  |  |
|---|---|---|---|
| Exon 6 | 5' forward primer | 5' | TTGGCTGAAAGCCAACAACCTG 3' |
|  | 3' reverse primer | 5' | AACATGCACGCATCCACAGC 3' |
|  | sequencing primers (forward) | 5' | TTGTAACACAGCATGTGG 3' |
| Exon 7 | 5' forward primer | 5' | GGTTCTGTCAGTATTAGCTGGG 3' |
|  | 3' reverse primer | 5' | TTCCTCCCTCTGCTCATCCTC 3' |
|  | sequencing primers (forward) | 5' | TTCCCACTCTGTCTCTC 3' |

Genetic alterations of TREX were further analyzed in breast cancers as wells as various tumors in which frequent LOHs were observed on 8p. A total of 315 primary tumors originated from a variety of organs and 14 cancer cell lines were analyzed. Mutations in the entire coding regions as well as surrounding intron-exon boundaries, were analyzed, but no somatic mutations were detected. In Case 9, a thyroid cancer patient, had a 9-bp insertion in her constitutional DNA. This 9-bp has been inserted at a direct repeat with a T as a spacer: 5'-GATGAGGC-T-GATGAGGC-A-3'resulting 5'-GATGAGGC-T-GATGAGGC-T-GATGAGGC-A-3', and amino acid sequence would change from Asp-Glu-Ala-Asp-Glu-Ala to Asp-Glu-Ala-Asp-Glu-Ala-Asp-Glu-Ala.

A G to A transition at the third nucleotide of codon 171 was also observed in one lung cancer cell line EBC-1. This base substitution does not change amino acid coding. Since the constitutional DNA of this cell line was not available, it is not possible to determine whether or not this base substitution occurred somatically. Although other 328 tumors did not harbor this base substitution, the possibility of a rare polymorphism cannot be excluded. A C to T transition at codon 605 was found only in two of 329 tumors. Again this base substitution does not affect amino acid coding. Constitutional DNAs of the patients of these two tumors also harbored this base substitution. 50 normal volunteers were also analyzed but none of them had this base substitution. However, this base substitution is thought to be a rare polymorphism rather than germline mutation. Besides these alterations, three polymorphisms were found: a polymorphism with no amino acid change in exon 3, at codon 409, and two polymorphisms in introns 4 and 5. These results are summarized in Table 3.

TABLE 3

Genetic alterations detected in HTRFX

| Position[a] | Alteration | Predicted effect |
|---|---|---|
| Exon 3 55 | 9 bp insertion[b] | 3 amino acid insertion |
| Exon 3 171 | CCG/CCA | silent (?) |
| Exon 3 409 | CCA/CCG | polymorphism (CCA/CCG 15/13) |
| Exon 3 605 | AAC/AAT | polymorphism (?) (AAC/AAT 100/0) |
| Intron 4 +36 | A/G | polymorphism (A/G - 29/17) |
| Intron 5 −30 | G/C | polymorphism (G/C - 16/30) |

[a]In exons, positions were indicated by the codons.
[b]In introns, + and − indicate downstream from the donor site and upstream from the acceptor site, respectively. This 9-bp insertion was observed in the constitutional DNA of one thyroid cancer (papillary carcinoma) patient.

Methods and Materials cDNA library screening. A 500 bp of cDNA insert of mouse TREX was purified from a digest of pBluescript DNA by agarose gel electrophoresis, labeled by random priming, and used to screen $1 \times 10^{10}$ plaques of an oligo(dT)+random primed human adult brain cDNA library (Clontech) at reduced stringency condition. Inserts from the clones identified in this way were transferred into pBluescript plasmids.

RT-PCR cDNA extension. Total RNA prepared from Jurkat cells was used for in vitro transcription. About 10 μg of total RNA was used as a template in a 25 μl RT reaction containing 40 μg of hexamer random primers. 10 μl of RT product was then used as a template in a 100 μl PCR reaction. Thirty cycles of amplification (1 min at 94° C., 1 min at 50° C., 2 min at 72° C.) were performed, and the products were analyzed on agarose gels. Products with unique sizes were produced from several primers. Individual products were excised from the gel, purified form QIAquick Gel Extracrion Kit (OIAGEN), and cloned into the pCR II vector (InVitrogen).

3' and 5'-RACE-Ready™ cDNAs from human brain and muscle were obtained from Clontech. PCR reactions were performed according to the manufacturer's protocol using the primers supplied with the cDNAs. PCR products were cloned to pCR II vectors as describe above.

DNA sequencing and analysis. DNA sequences were determined using ThermoSequenase (Amersham), α-$^{33}$P-ddNTP labeling, and autoradiographic detection. Complete sequences for both sense and antisense strands were determined for the cDNA. DNA and protein sequence analysis and database searches were performed using MacVector™ sequence analysis software (Osford Molicular Group) and by BLAST program.

Fish Analysis

Metaphase or prophase spreads were prepared from phytohemagglutinin-stimulated peripheral blood lymphocytes of a normal healthy female volunteer (Inazawa et al., 1994) (25). Slides were denatured at 75° C. for 3 min in 70% formamide/2×SSC (0.3M NaCl, 0.03M sodium citrate, pH7), immersed in 70% ethanol at −20° C., and dehydrated in 100% ethanol. Two-color FISH, using pBSIISK(+)–TREX, a plasmid clone which contains TREX cDNA and RMC08L009 (pJM128), a plasmid clone which contains chromosome 8 centromere sequence (Donlon et al., 1986) (26), was performed essentially as described previously (Inazawa et al., 1993) (27). RMC08L009 was obtained from the Resource for Molecular Cytogenetics, LBNL/UCSF. Briefly, 0.5 μg of pBSIISK(+)--TREX or 0.5 μg of RMCO8L009 was labeled with biotin-16-dUTP (Boehringer Mannheim GmbH, Mannheim, Germany) or digoxigenin-11-dUTP (Boehringer Mannheim) by nick translation, respectively. The mean fragment size of the nick-translated probes was between 300 bp and 600 bp. DNA probes were precipitated with 20 μg of sonicated salmon sperm DNA and 20 μg of *Escherichia coli* tRNA and then dissolved in 30 μl of formamide. The biotin- and digoxigenin-labeled probes were mixed at a ratio of 5/5.5 (v/v), and human Cot-1 DNA (Gibco BRL, Gaithersburg, Md.) dissolved in formamide was added to the mixed solution at a concentration of 0.4 $\mu/\mu l$. This mixture was heat-denatured at 75° C. for 10 min and mixed with an equal volume of 4×SSC/20% dextran sulfate, and hybridized to slides of normal metaphase or prophase chromosomes at 37° C. for 2 days in a humid chamber. After hybridization, the slides were washed for 15 min sequentially with 50% formamide/2×SSC at 37° C., 2×SSC, 1×SSC, and 4×SSC at room temperature, and incubated in 4×SSC/1% Block Ace (Dainippon Pharmaceutical Co., Ltd., Osaka Japan) containing avidin-FITC (15 $\mu g/ml$) and anti-digoxigenin-rhodamine (1 $\mu g/ml$) Boehringer Mannheim) at 37° C. for 40 min. Slides were washed for 10 min each in 4×SCC, 4×SSC/0.05% Triton X-100 and 4×SSC at room temperature, and for 5 min each in 2×SSC and distilled water at room temperature. Slides were then counterstained with 0.15 $\mu g/ml$ of 4,6-diamidino-2 phenylindole (DAPI) in an antifade solution.

A Nikon Eclipse E800 microscope was used for visualization of DAPI banding patterns and the hybridization signals. Digital images were acquired using a COHU high performance CCD camera (San Diego, Calif.) controlled with Mac Probe 3.4 software (Perceptive Scientific Instruments, Inc., Chester, UK). At least 50 metaphase or prophase cells were examined to determine the chromosomal location of TREX gene.

Western blotting. Proteins were separated by electrophoresis in 7.5% polyacrylamide/SDS gels, and electrophoretically transferred to membranes for 1 h. The membranes were blocked in TBS (100 mM Tris, 150 mM NaCl) containing 10% nonfat dried milk and 0.1% Tween-20 for 2 h. Incubation of the membranes with anti-TREX monoantibody was performed in TBS containing 5% nonfat milk and 0.1% Tween 20 for 1 h and then membranes were washed with TBS containing 0.1% Tween 20 for 30 min and detected with ECL detection kit.

DNA and RNA preparation. All the tumor and normal tissues were obtained from Department of Otolaryngology, CPMC, Columbia University. The histopathological classification was as suggested by the WHO committee. Both normal and tumor tissues were collected at the time of surgery and snap-frozen. High molecular weight DNAs were obtained from the tissue by phenol-chloroform extraction and ethanol precipitation. Total RNAs were prepared by using TRIzol Reagent (GIBCOBRL). Sections from each of the tumors were histopathologically examined. All tumor samples contained greater than 90% tumor cells.

Mutational analysis. 10 PCR primers and 12 sequencing primers were designed to analyze the whole ORF of TREX. A 50 $\mu l$ reaction contained 150 ng genomic DNA, 20 pmol of each primer, 1X Expand™ High Fidelity PCR buffer (Boehringer Mannheim), and 2.6 U Expand™ High Fidelity PCR System enzyme mix (Boehringer Mannheim). After an initial denaturation for 2 min at 94° C., 30 cycles of 20 S at 94° C., 30 s at 60° C., and 3 min at 68° C., and final extension for 7 min at 68° C. were carried out in a PCR microtube thermal Cycler (Perkin Elmer) . Direct sequencing of PCR products was performed after pre-treatment by Pre-PCR sequencing kit (Amersham) using the sequencing primers as described above. All mutations were confirmed by sequencing a newly amplified product.

References for the Second Series of Experiments

1. Schmale, G. A., Conrad, E. U. & Raskind, W. H. The natural history of hereditary multiple exostoses. *J. Bone Joint Surg. Am.* 76, 986-992 (1994).
2. Leone, N. C. et al. Genetic heterogeneity in families with hereditary multiple exostoses. *Am. J. hum. Genet.* 53, 71-79 (1993).
3. Luckert-Wichlund, C. L. et al. Natural history study of hereditary multiple exostoses. *Am. J. Med. Genet.* 55, 43-46 (1995).
4. Ludecke, H. J. et al. Molecular dissection of a contiguous gene syndrome: localization of the genes involved in the Langer-Giedion Synchrome. *Hum. Mol. Genet.* 4, 31-36 (1995).
5. Wuyts, W. et al. Refinement of the multiple exostoses locus (EXT2) to a 3-cM interval on chromosome 11. *Am. J. Hum. Genet.* 57, 382-387 (1995).
6. Le Merrer, M. et al. A gene for hereditary multiple exostoses maps to chromosome 19p. *Hum. Mol. Genet.* 3, 717-722 (1994).
7. Ahn, J. et al. Cloning of the putative tumour suppressor gene for hereditary multiple exostoses (EXT1). *Nature Genet.* 11, 137-143 (1995).
8. Sticken, D. et al. The EXT2 multiple exostoses gene defines a family of putative tumour suppressor genes. *Nature Genet.* 14, 25-32 (1996).
9. Wise, C. et al. Identification and localization of the gene for EXTL, a third member of the multiple exostoses gene family. *Genome Res.* 7, 10-16 (1997).
10. Wuyts, W., et al. Identification and characterization of a novel member of the EXT gene family, EXTL2. *Eur. J. Hum. Genet.* 5, 382-389 (1997).
11. Kashiwada, M. et al. TREX, a Novel Gene of Hereditary Multiple Extoses (EXT) Gene Family, Involved in TRAF-mediated Signaling (in press).
12. Haggard, N. et al. Allelic imbalance on chromosome 1 in human breast cancer. Microsatellite repeat analysis. *Genes Chromosomes Cancer* 12, 24-31 (1995).
13. Nagai, H. et al. Detection and cloning of a common region of loss of heterozygosity at chromosome 1p in breast cancer. *Cancer Res.* 55, 1752-1757 (1995).
14. Ezaki, T., et al. Deletion mapping on chromosome 1p in well-differentiated gastric cancer. *Br. J. Cancer* 73, 424-428 (1996).
15. Mulligan, J. M. et al. Genetic events in tumour initiation and progression in multiple endocrine neoplasia type 2. *Genes Chromosomes Cancer* 6,166-177 (1993).
16. Lothe, R. A. et al. Deletion of 1p loci and microsatellite instability in colorectal polyps. *Genes Chromosomes Cancer* 14, 182-188 (1995).
17. Zimonjic, D. B. et al. Molecular cytogenetics of human papillomavirus negative cervical carcinoma cell lines. *Cancer Genet. Catogenet.* 82, 1-8 (1995).
18. Kazak., M. An analysis of 5'-noncoding sequences from 699 vertebrate messenger RNAs. *Nucl. Acids Res.* 15, 8125-8148 (1987).
19. Cowan, J. M., Beckett, M. A., Weichselbaum, R. R. Chromosome changes characterizing in vitro response to radiation in human squamous cell carcinoma lines. *Cancer Res.* 53, 5542-5547 (1993).
20. Vocke, C. D. et al. Analysis of 99 microdissected prostate cardinoma reveals a high frequency of allelic loss on chromosome 8p12-21. *Cancer Res.,* 56, 2411-2416 (1996).
21. Courjal F. et al. Mapping of DNA amplifications at 15 chromosomal localizations in 1875 breast tumors: definition of phenotypic groups. *Cancer Res.* 57, 4360-4367 (1997).
22. Richter J., et al. Marked genetic differences between stage pTa and stage pT1 papillary bladder cancer detected by comparative genomic hybridization. *Cancer Res.* 57, 2860-2864 (1997).

23. Tanaka, K. et al. Suppression of tumorigenicity and invasiveness of colon carcinoma cells by introduction of normal chromosome 8p12-pter. *Oncogene.* 12, 405-410 (1996).
24. Shapiro, M. B. and Senapathy, P. RNA splicing junctions of different classes of eukaryotes: sequence statistics and functional implications in expression. *Nucleic Acids Res.* 15, 7155-7174 (1987).
25. Inazawa J., Ariyama T., Tokina T., Tanigami A., Nakamura Y., Abe T. (1994) High resolution ordering of DNA markers by multi-color fluorescent in situ hybridization of prophase Chromosomes. Cytogenet Cell Genet 65:130-135.
26. Donlon T., Wyman A. R., Mulholland J., Barker D., Bruns G., Latt S., Botstein D. (1986) Alpha satellite-like sequences at the centromere of chromosome #8 Am. J. Hum. Genet. 39: A196.
27. Inazawa J., Saito H., Ariyama T., Abe T., Nakamura Y. (1993) High resolution cytogenetic mapping of 342 new cosmid markers including 43 RFLP markers on human chromosome 17 by fluorescence in situ hybridization. Genomics 17:153-162.

THIRD SERIES OF EXPERIMENTS

Abbreviations used herein: TNF-α, tumor necrosis factor-α; NF-κB, nuclear factor-κB, TRAF, tumor necrosis factor receptor-associated factor; PCR, polymerase chain reaction; RACE, rapid amplification of cDNA ends; PBS, phosphate-buffered saline; luc, luciferase; HEK, human embryo kidney; HA, hemgglutinin; PMSF, phenylmethylsulfonyl fluoride; TRITC, trimethylrhodamineisothiocynate; EGFP, enhanced green fluorescent protein.

EXTL3 is a member of the EXT gene family and a putative tumor suppressor gene. Here we identified the cDNA encoding mouse homolog of EXTL3 and examined the effect of its expression on nuclear factor-κB (NF-κB) activity. The mouse EXTL3 protein is 97% homologous to the human EXTL3. Northern blot analysis indicated that mouse EXTL3 is ubiquitously expressed in tissues, with highest expression in the heart, brain, and skeletal muscle. Over expression of EXTL3 enhanced tumor necrosis factor-α (TNF-α)- and tumor necrosis factor receptor-associated factor 2 (TRAF2)-induced NF-κB activation. Structure-functional analysis revealed that the transmembrane region near the amino terminus was required for this effect of mouse EXTL3 on NF-KB activity. The results of subcellular localization studies revealed that EXTL3 was expressed predominantly at the endoplasmic reticulum. Interestingly, co-expression of EXTL3 with TRAF2 facilitates to change in distribution of EXTL3 and TRAF2 surrounded the EXTL3-containing vesicle caused by TRAF2. These results strongly suggest that EXTL3 may modulate a signal cascade mediated by TNF-α.

Tumor necrosis factor a (TNF-α)[3] is a potent inflammatory cytokine that generates two different signals: it induces apoptosis, and it activates the transcription factor NF-κB (1, 2). The inhibition of NF-κB during TNF-α stimuli results in apoptosis in various cell lines which are originally resistant to TNF-α-induced cell death (3-5).

Therefore, activation of NF-κB likely induces the expression of genes that counteract apoptotic signals and prevent cell death.

Hereditary multiple exostoses syndrome (EXT) is an autosomal dominant disorder characterized by the formation of multiple cartilage-capped tumors that develop from the outgrowth plate of endochondral bone (6). Genetic linkage analysis has mapped loci for EXT at chromosomes 8q24. 1 (EXT1) (7, 8), 11p11-13 (EXT2) (9, 10), and 19p (EXT3) (11). Both EXT1 (12) and EXT2 (13) genes have been identified; these proteins share extensive sequence similarity, especially at the carboxyl terminus. The three EXT-like genes, EXT1 (14), EXTL2/EXTR2 (15, 16), and EXTL3/EXTR1 (16, 17), which also share considerable homology, have been assigned to human chromosomes 1p36. 1, 1p21, 8p21, respectively. Because these chromosomal regions have been associated with high frequent loss of heterozygosity in various human cancers, it has been thought that putative tumor suppressor genes exist in these loci (18-20). Therefore, the EXT family including EXTL3 may represent a class of putative tumor suppressors.

Recently, EXT1 and EXT 2 were identified as glycosyl-transferases required for biosynthesis of heparin sulfate (21, 22). However, functional role to another member of the family is still not defined. Here we report that mouse EXTL3 affects NF-kB activity stimulated by TNF-α. We also describe the subcellular localization of this protein at the endoplasmic reticulum.

Materials and Methods

Materials. Recombinant human tumor necrosis factor-α (TNF-α) was obtained from R&D Systems, Inc. (Minneapolis, Minn.). TRITC-conjugated concanavalin A was obtained from Sigma (St. Louis, Mo.). Fetal calf serum (FCS) was obtained from HyClone (Logan, Utah). The NF-κB-dependent reporter gene construct pELAM-luc, in which the human E-selectin promoter region (−730/+52) has been inserted into pGL3 by using SacI/BqlII sites, was kindly provided by MBL (Nagoya, Japan).

cDNA cloning of mouse EXTL3. Mouse EXTL3 cDNA was isolated from the Mouse Brain 5'-Strech Plus cDNA library (Clontech, California, Calif.) by using human EXTL3 as a probe. To extend the partial sequence, RACE was carried out as described in the manufacturer's manual (Clontech)

Northern blot analysis. A Northern blot filter containing mouse poly(A)+ RNAs from eight different tissues was purchased from Clontech. The filter was hybridized with the 1.2 kb EXTL3 cDNA fragment that contains the entire open reading frame as reconstructed from the RACE product.

Plasmid construction and transfection. To construct the expression plasmid, we PCR-amplified the full length EXTL3 cDNA fragment by using the forward primer (5'-CGCGGATCCACCATGACAGGCTATACCATGTTG CGGA-3'), which contains a BamHI site, and the reverse primer (5'-CCCAAGCTTTAGATGAACTTGAAGCACTTGGT-3'), which contains a HindIII site. To construct the deletion mutant lacking the N-terminal region (ΔN), the ΔN fragment was amplified by using the forward primer (5-'-CGCGGATCCACCATGTCCTACAAGGAGCTGAT GGCCCA-3') and the reverse primer used for the full-length fragment. To construct the deletion mutant lacking the c-terminal region (ΔC), the ΔC fragment was amplified by using the reverse primer 5'-CCCAAGCTTGCTACCTCTTCCCGGATGGGAGCA-3' and the same forward primer as that for the full-length fragment. For the deletion mutant lacking both the N- and C-terminal portions (N&C), the ΔN&C fragment was amplified by using the same forward primer as that for the ΔN fragment and the reverse primer used to generate the ΔC fragment. After digestion with BamHI and HindIII, full-length and truncated EXTL3 PCR products were ligated into pcDNA3.1(−)/Myc-His B (invitrogen, Carlsbad, Calif.) such that the myc epitope tag and the 6xhis tag were in-frame for subsequent translation.

For construction of EGFP-tagged EXTL3 expression plasmids, the full-length coding region for mouse EXTL3 and the ΔN region was PCR-amplified by using the forward primer 5'-CCCAAGCTTACCATGACAGGCTATACCATGTTG CGGA-3' and the reverse primer used for the full-length fragment described previously. In addition, the ΔN region was generated by using the forward primer 5"-CCCAAGCTTACCATGTCCTACAAGGAGCTGAT GGCCCA-3' and the same reverse primer used for the full-length fragment. After digestion with HindIII, the full-length and ΔN EXTL3 PCR products were ligated into pEGFP-N2 (Clontech) such that EGFP was in-frame for subsequent translation.

Full-length coding regions of mouse TRAF2 and TRAF3 were amplified by PCR and subcloned into FLAG-tagged pCR3.1 (Invitrogen). Full-length coding regions of human TRAF2 were amplified and subcloned into hemagglutinin (HA)-tagged pcDNA3 (Invitrogen).

Cellculture and transfection. Human embryo kidney 293 (HEK293) cells were maintained in Eagle's minimum essential medium containing 10% fetal calf serum, 100 U/mL penicillin, and 100 μg/mL streptomycin (GIBCO-BRL, Grand Island, N.Y.). For experiments, HEK293 cells were seeded at a density of $10^6$ cells/dish in 10-cm culture dishes and were cultured for 3 days. Then, the cells were transfected by standard calcium phosphate co-precipitation method using commercial solution (5prime 3prime inc. ).

Preparation of nuclear extracts. For nuclear extracts, cells were treated with or without TNF-α (20 ng/mL) for 1 h, washed with ice-cold PBS, and detached by using 5 mM EDTA in PBS. After pelleting, the cells were resuspended in wash buffer (10 mM Tris-HCl [pH 7. 5], 130 mM NaCl, 5 mM KCl, 8 mM $MgCl_2$, then pelleted and resuspended in hypotonic buffer (20 mM HEPES-KOH [pH 7. 9], 5 mM KCl, 0.5 mM $MgCl_2$, 0.5 mM DTT, 0.5 mM PMSF). After incubation for 10 min on ice, the cell suspension was homogenized by using five strokes in a Dounce homogenizer. The homogenate was centrifuged for 10 min at 4000 rpm. Sedimented nuclei were resuspended in extraction buffer (20 MM HEPES-KOH [pH7. 9], 25% glycerol, 500 mM NaCl, 1.5 mM $MgCl_2$, 0.2 mM EDTA, 0.5 mM DTT, 0.5 mM PMSF, 0.5 μg/ml pepstatin A, 1.3 μg/ml spermidine) and broken by using five strokes in a Dounce homogenizer. After vortexing for 1 h, the nuclear suspension was centrifuged for 10 min at 15,000 rpm. The supernatant was dialyzed against binding buffer (20 mM HEPES-KOH [pH 7.9], 10% glycerol, 50 mM KCl, 1.5 mM $MgCl_2$, 0.5 mM EDTA, 0.5 mM DTT, 0.5 mM PMSF). After centrifugation, the supernatant was used as the nuclear extract.

Electrophoretic mobility shift assays. Electrophoretic mobility shift assays were performed by incubating an aliquot of nuclear extract containing 5 μg protein with 2 μg poly (dI-dC) Amersham Pharmacia, Uppsala, Sweden) in assay buffer (13 mM HEPES [pH 7. 8], 50 mM KCl, 4.3 mM $MgCl_2$, 10% glycerol, 0.3 mM DTT, 0.3 mM PMSF [final volume, 30 μl]). The binding reaction was started by adding endo-labeled NF-κB-specific oligonucleotide (Promega, Madison, Wis.) with [$Y^{32}P$]ATP (Amersham Pharmacia) and T4 polynucleotide kinase and the reaction mixture was incubated for 30 min at room temperature. The samples were separated by polyacrylamide gel electrophoresis in low ionic-strength buffer (0.25xTris-borate-EDTA). Activated NF-κB complexes were identified by using super-shift analysis with an antibody that recognizes NF-KB subunit (Santa Cruz, California, Calif.).

Luciferase assay. For a reporter gene assay, HEK293 cells were transfected with 500 ng of the NF-κB-dependent reporter gene construct pELAM-luc, 500 ng of the internal control construct pRL-TK (Promega) and 10 μg of each expression construct needed. DNA concentrations were kept constant by supplementation with empty vector. Cells were lysed 24 h after transfection, and reporter gene activity was determined by using the Dual luciferase assay system (Promega). Luminescence was measured in a Lumat LB 9507 (BERTHOLD GmbH & Co. KG, Bad Wildbad, Germany).

Fluorescence microscopy. HEK293 cells cultured on cover glasses were transfected with the EGFP-tagged EXTL3 construct and the FLAG-tagged TRAFs constructs by a standard calcium phosphate co-precipitation method. The cells were fixed with 3.7% formalin in PBS for 10 min at room temperature 24 h after transfection. The cells were washed three times with PBS and treated with 0.2% Triton X-100 in PBS for 5 min, followed by a 30 min incubation in blocking solution (PBS containing 5% BSA). After blocking, the cells were incubated with 100 μg/mL TRITC-conjugated concanavalin A for 30 min. The cells were washed three times with PBS and then incubated with M2 anti-FLAG monoclonal antibody (Sigma) at 20 μg/ml in 0.1% BSA in PBS for 1 h. Cells were washed three times with PBS then incubated with Cy5-conjugated anti-mouse IgG antibody (Jackson ImmunoResearch Laboratories, Inc., West Grove, Pa.) at 20 μg/ml in 0.1% BSA and 0.1% Tween 20 in PBS for 1 h. The cells were then washed with PBS and mounted on slide glasses. Fluorescence was visualized by using a Carl Zeiss LSM510 confocal laser scanning microscope (Oberkochen, Germany).

Accession Number. The Genbank accession number for mouse EXTL3 is AF083550.

RESULTS

Cloning of murine EXTL3 cDNA and distribution of its mRNA in various tissues. From the mouse brain cDNA library, several colonies were selected by using human EXTL3 cDNA as a probe. To extend the partial sequence, RACE were carried out as described in the manufacturer's manual. An open reading frame encoding a predicted protein of 918 amino acids was obtained. Mouse EXTL3 protein is 97% homologous to the human protein (FIG. 9A).

Figure 9B:
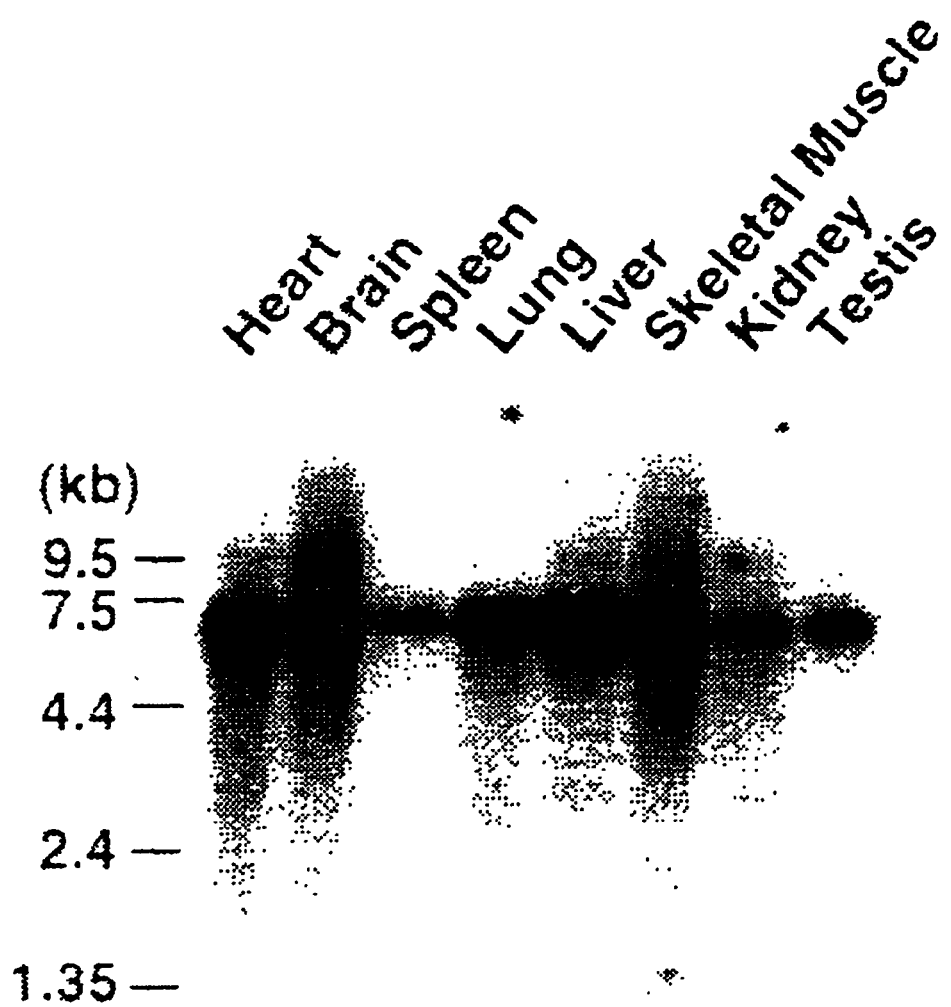

A Northern blot filter containing mouse poly(A)+RNAs from eight different tissues was hybridized with a 1.2 kb fragment of mouse EXTL3 cDNA. A single transcript of 6.0 kb was detected in all tissues examined, with highest expression in heart, brain, and skeletal muscle (FIG. 9B). The results are consistent with those associated with human EXTL3.

Figure 10A:
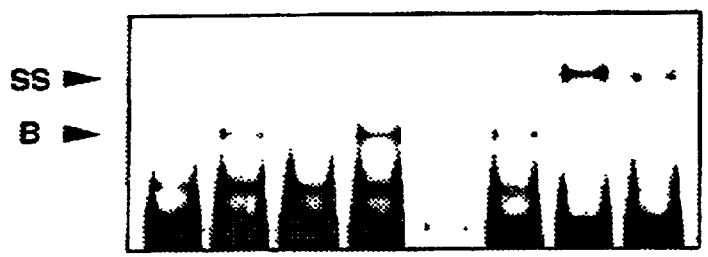
FIGS. 10A-10C. Enhancement of NF-κB activation stimulated by TNF-α in HEK293 cells overexpressing EXTL3.
Figure 10B:
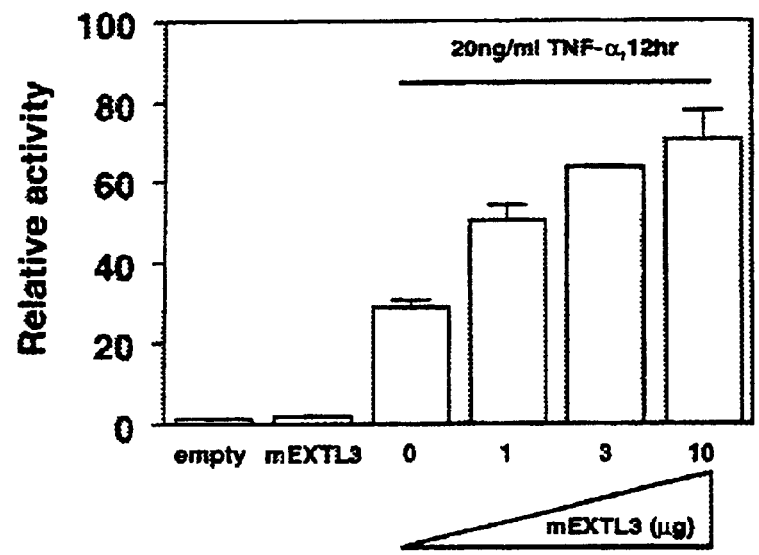
Figure 10C:
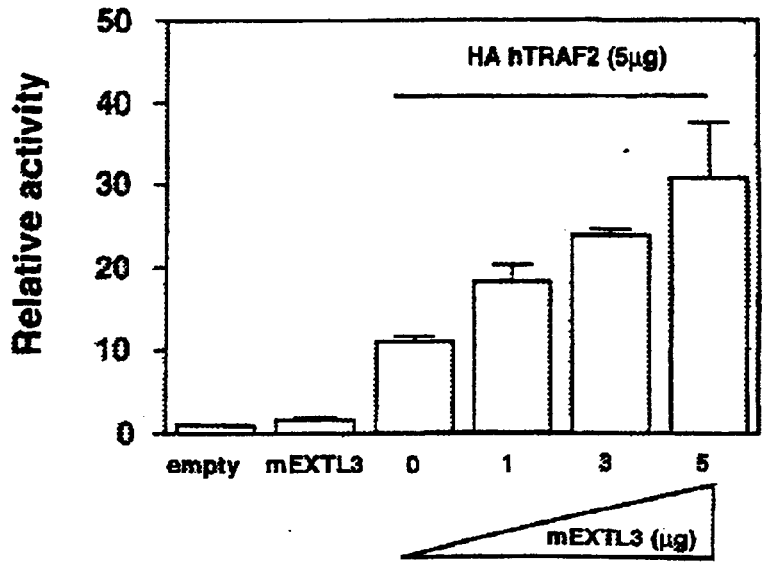

Effect of EXTL3 protein expression on NF-κB activity. To investigate the effects of EXTL3 on TNF-α-induced NF-κB activation, an electrophoretic mobility shift assay was carried out. NF-κB activation was detected in the nuclear extract stimulated by TNF-α (FIG. 10A). The super shift of the band with anti-NF-kB p50 subunit antibody or anti-NF-kB p65 subunit antibody was observed. These results might indicate that the p65/p50 heterodimer was formed in TNF-α-treated HEK293 cells. In EXTL3-transfected cells, TNF-α-induced NF-κB activation was enhanced markedly (FIG. 10A). To confirm this finding, we also examined the effect of EXTL3 on NF-κB activation by using a luciferase assay. Over expression of EXTL3 enhanced TNF-α-induced NF-κB activation in a concentration-dependent manner (FIG. 10B). Similar results were obtained when EXTL3 was co-expressed with TRAF2 (FIG. 10C).

EXTL3 has a putative transmembrane region at its N-terminus and the EXT domain at its C-terminus (FIG.

Figure 11A:
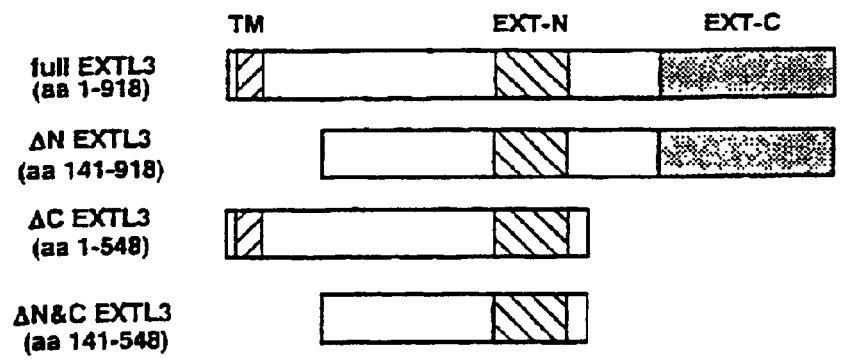
Figure 11B:
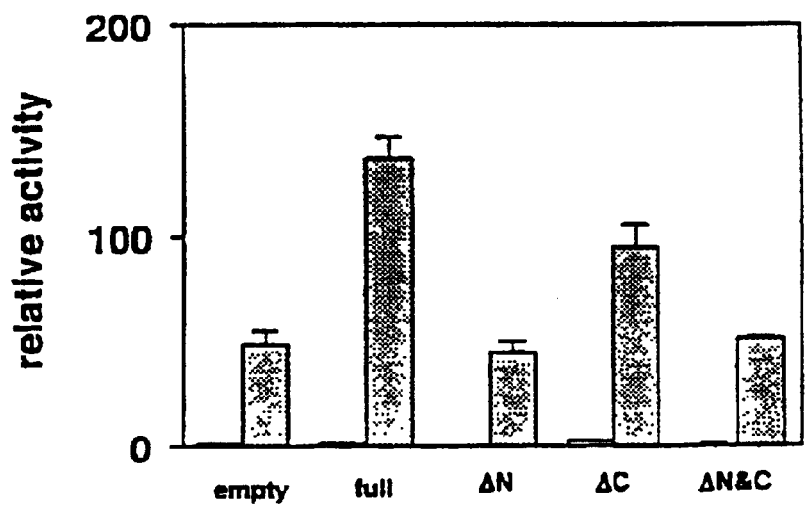
Figure 11C:
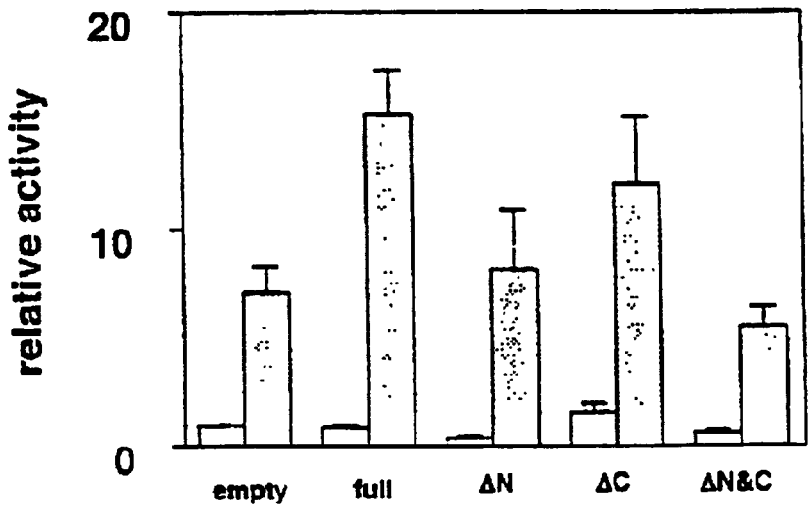

11A). The EXT domain comprises two subdomains, EXT-N and EXT-C. To determine the region necessary for the enhancement of NF-κB activation, we constructed a series of EXTL3 deletion mutants and investigated their effect on NF-κB activation. The results revealed that enhancement of NF-κB activation was not detected in N-terminal truncated EXTL3 expressed HEK293 cells, but the C-terminal truncation mutant enhanced NF-κB activation (FIG. 11B and 11C). These results showed that the transmembrane region closer to the N-terminus was required for modulation of NF-κB activation induced by TNF-α or TRAF2.

Cellular location of EXTL3 protein. To determine the subcellular localization of EXTL3, HEK293 cells were transiently transfected with the EGFP-tagged EXTL3 expression plasmid. As shown in FIG. 11D-b, EXTL3 protein is detected at the endoplasmic reticulum. By contrast, the localization pattern of the N-terminal deletion mutant is similar to that of EGFP (FIG. 11D-a and 11D-c). These results suggested that the transmembrane region closer to the N-terminus is necessary for pre-nuclear localization. To elucidate the role of the EXTL3 protein in TNF-A signaling, we examined the effects of TRAF2 and TRAF3 on the subcellular distribution of EXTL3. Although no change in EXTL3 localization was observed in HEK293 cells co-transfected with TRAF3, TRAF2 affected the subcellular distribution of EXTL3 (FIG. 12). TRAF2 caused the formation of vesicles containing EXTL3. As shown in FIG. 12H, the EXTL3 localization and the region stained with TRITC-conjugated concanavalin A clearly overlap. This result is consistent with localization of EXTL3 at the endoplasmic reticulum. However, EXTL3-containing vesicles appeared in cells co-expressing TRAF2 cells that were not stained with concanavalin A (FIG. 12D). Interestingly, TRAF2 existed at the surface of these vesicles.

DISCUSSION

In the present study, we demonstrate that EXTL3 markedly enhances both TNF-α- and TRAF2-induced NF-κB activation, although EXTL3 slightly stimulates NF-κB activity in itself. The study using EXTL3 truncation mutants demonstrates that the N-terminal region containing a putative transmembrane domain is required for EXTL3-associated enhancement of NF-κB. Indeed, EXTL3 locates at endoplasmic reticulum, which consists with prediction based on the amino acid sequence (17). Therefore, the correct sorting of EXTL3 may be necessary for the enhancement of TNF-α- and TRAF2-induced NF-κB activation.

Previous studies demonstrated that several TRAFs associate with the TNF receptor and initiate signal transduction. TRAF2, but not TRAF3, is responsible for the activation of NF-κB (23). We demonstrated that EXTL3-contented vesicles appear in TRAF2 co-transfected cells but not in TRAF3 co-transfected cells. Moreover, TRAF2 exists on the surface of these vesicles. These also implicate EXTL3 in TNF-α-induced signal transduction. Recently, numerous protein mediating signals initiated by TNF-α have been identified (24). There is a possibility that EXTL3 affects the function of these proteins such as TRAF2. Several groups reported that the activation of NF-κB prevents apoptosis (3-5). Here, we report that EXTL3 may involved in the TNF-α-induced NF-κB activating pathway, which may help to understand the tumor suppressor activity of EXTL3.

Heparin sulfate proteoglycans are ubiquitously present on the cell surface and in the extracellular matrix. Heparin sulfate chains interact with a variety of proteins and are therefore implicated not only in various cellular responses but also in diverse physiological phenomena (25). The role of glycosaminoglycan in the transmembrane signaling induced by fibroblast growth factor is well documented (28-30). Recently, it has been reported that EXT1 and EXT 2 encode glycosyltransferases involved in the chain-elongation step of heparin sulfate (21, 22). Therefore, another member of EXT family, perhaps EXTL3, also may be involved in glycosaminoglycan synthesis. Indeed, EXTL3 localizes to the endoplasmic reticulum, as EXT1 does (21, 26). Beside this, TNF-α has an affinity for heparin (27) . These let us speculate that glycosaminoglycan may play a pivotal role in TNF-α-induced signal transduction as well as in fibroblast growth factor-induced signaling, but further studies are required to confirm our hypothesis.

The chromosomal localization of EXTL3 has been assigned to 8p21 (16, 17, 31) and the EXTL3 gene was mapped in the common region of deletion in primary breast cancer (31). The extensive mutation search was performed using the 329 primary human cancers including chondrosarcomas, breast and lung cancers and the results revealed that the frequent somatic mutation was not detected in the sporadic human cancers (31d), suggesting that EXTL3 may not be involved in tumor development and/or progression. However, loss of hetrozygosity in the EXTL3 gene may cause unbalance of the regulation of NF-κB activation by TNFR-mediated signal transduction and eventually its loss of EXTL3 function may contribute to inhibition of apoptosis in primary human cancers. Further studies will be necessary to better understandings of association between EXTL3 function and tumor development and/or progression.

References for Third Series of Experiments

1. Hale, A. J., Smith, C. A., Sutherland, L. C., Stoneman, V. E. A., Longthorne, V. L., Culhane, A. C. and Williams, G. T. Apoptosis: Molecular regulation of cell death. Eur. J. Biochem., 236: 1-26, 1996.
2. Barinaga, M. Forging a path to cell death. Science, 273: 753-737, 1996.
3. Beg, A. A. and Baltimore, D. An essential role for NF-κB in preventing TNF-α-induced cell death. Science, 274: 782-784, 1996.
4. Wang, C. Y., Mayo M. W. and Baldwin, A. S. TNF- and cancer therapy-induced apoptosis: Potentiation by inhibition of NF-κB. Science, 274: 784-787, 1996.
5. Van Antowerpen, D. J., Martin S. J., Trafri, T., Green, D. R. and Verma, I. M. Suppression of TNF-α-induced apoptosis by NF-κB. Science, 274:787-789, 1996.
6. Solomon, L. Hereditary multipule exostoses. Am. J. Hum. Genet., 16: 351-365, 1964.
7. Cook, A., Raskind, W., Blanton, S. H., Pauli, R. M., Greed, R. C., Francomano, C. A., Puffenberger, E., Conrad, E. U., Schmale, G., Schellenberg, G., Wijsman, E., Hecht, J. T. Wells, D. and Wagner, M. J. Genetic heterogeneity in families with hereditary multiple exostoses. Am. J. Hum. Genet., 53: 71-79, 1993.
8. Ludecke, H. J., Ahn, J., Lin, X., Hill, A., Wagner, M. J., Schomburg, L., Horsthemke, B., and Wells. Genomic organization and promoter structure of the human EXT1 gene. Genomics, 4: 31-36, 1995.
9. Wu, Y. Q., Heutink, P. de Vries, B. B. Sandkujil, L. A., van den ouweland, A. M., Niemeijer, M. F., Galjaad H., Reyniers, E., Willems, P. J. and Halley, D. J. Assignment of a second locus for multiple exostoses to the pericentromeric region of chromosome 11. Hum. Mol. Genet., 3: 167-171, 1994.
10. Wuyts, W., Van Hul, W., Wauters, J., Nemtsova, M., Reyniers, E., Van Hul, E. V., De Boulle, K., de Vries, B. B., Hendrickx, J., Herrygers, I., Bossuyt, P., Balemans, W., Fransen, E., Vits, L., Coucke, P., Nowak, N. J., Shows, T. B., Mallet, L., van den Ouweland, A. M., McGaughran, J., Halley, D. J. and Willems, P. J. Positional cloning of a gene involved in hereditary multiple exostoses. Hum. Mol. Genet., 5: 1547-1557, 1996.

11. Le Merrer, M., Legeai-Mallet, L., Jeannin, P. M., Horsthemke, B., Schinzel, A., Plauchu, H., Tourain, A., Achard, F., Munnich, A. and Maroteaux, P. A gene for hereditary multiple exostoses maps to chromosome 19p. Hum. Mol. Genet., 3: 717-722, 1994.

12. Ahn, J., Ludecke, H-J, Lindow, S., Horton, W., Lee, B., Wanger, M. J., Horsthemke, B. and Wells, D. Cloning of the putative tumor suppressor gene for hereditary multiple exostoses (EXT1). Nature Genet., 11: 137-141, 1995.

13. Sticken, D., Clines, G., Burbee, D., Ramos, P., Thomas, S., Hogue, D., Hecht, J. T., Lovett, M. and Evans, G. A. The EXT2 multiple exostoses gene defines a family of putative tumour suppressor genes. Nature Genet., 14: 25-32, 1996.

14. Wise, C. A., Clines, G. A., Massa, H., Trask, B. J. and Lovett, M. Identification and localization of the gene for EXTL, a third member of the multiple exostoses gene family. Genome Res., 7: 10-16, 1997.

15. Wuyts, W., Van Hul, W., Hendrickx, J., Wauters, J., Spelemen, F., De Boulle, K., Bossuyt, P., Van Agtmael, T. and Willems, P. J. Identification and characterization of nevel member of the EXT gene family, EXTL2. Eur. J. Hum. Genet., 5: 382-389, 1997.

16. Saito, T., Seki, N., Yamauchi, M., Tsuji, S., Hayashi, A., Kozuma, A. and Hori, T. Structure, chromosomal location, and expression profile of EXTR1 and EXTR2, new member of the multiple exosotses gene family. Biochem. Biophy. Res. Comm., 243: 61-66, 1998.

17. Van Hul, W., Wutys, W., Hendrickx, J., Speleman, F., Wauters, J., De Boulle, K., Van Roy, N., Bossuyt, P. and Willems, P. Identification of a third EXT-like gene (EXTL3) belonging to the EXT gene family. Genomics, 47: 230-237, 1998.

18. Caron, H., Peter, M., Van Sluis, P., Speleman F., De Kraker, J., Laureys, G., Michon, J., Brugieres, L., Voute, P. A., Westerveld, A., Slater, R., Delattre, O. and Versteeg, R. Evidence for two tumour suppressor loci on chromosomal bands 1p35-36 involved in neuroblastoma: One plobably imprinted, another associated with N-myc amplication. Hum. Mol. Genet., 4: 535-539, 1995.

19. Becker, S. A., Zhou, Y-Z. and Slagle, B. L. Frequent loss of chromosome 8p in hepatitis B virus-positive hepatocellular carcinoma from china. Cancer Res., 56: 5092-5097, 1996.

20. Seitz, S., Rohde, K., Bender, E., Nothnagel, A., Koble, K., Schlag, P. M. and Scherneck, S. Strong indication for breast cancer suspectibility gene on chromosome 8p12-p22: Linkage in German breast cancer families. Oncogene, 14: 741-743, 1997.

21. McCormick, C., Leduc, Y., Martindale, D., Mattison, K., Esford, L. E., Dyer, A. P. and Tufaro, F. the putative tumor suppressor EXT1 alters the expression of cell-surface haparan sulfate. Nature Genet., 19: 158-161, 1998.

22. Lind, T., Tufaro, T., McCormick, C., Lindahl, U. and Lindholt, K. The putative tumor suppressors EXT1 and EXT2 are glycosyltransferases required for biosynthesis. J. Biol. Chem., 273: 26265-26268, 1998.

23. Rothe, M., Sarma, V., Dixit, V. M. and Goeddel, D. V. TRAF2-maddiated activation of NF-κB by TNF-receptor2 and CD40. Science, 269: 1424-1427, 1995.

24. Baker, S. J. and Reddy, E. P. Modulation of life and death by TNF receptor superfamily. Oncogene, 17: 3261-3270, 1998.

25. Bernfield, M., Kokenyesi, R., Kato, M., Hinkes, M. T., Spring, J., Gallo, R. L. and Lose, E. J. Biology of the syndecans: A family of thensmembrane heparan sulfate proteoglycans. Annu. Rev. Cell Biol., 8: 369-393, 1992.

26. Yayon, A., Klagsbrun, M., Esko, J. D., Leder, P. and Ornitz, D. M. Cell surface, heparin-like molecules are required for binding of basic fibrobrast growth factor to its high affinity receptor. Cell, 64: 841-848, 1991.

27. Kan, M., Wang, F., Xu, Jianming, Crabb, J. B., Hou, J. and McKeehan, W. L. An essential heparin-binding domain in the fibribrast growth factor receptor kinase. Science, 259: 1918-1921, 1993.

28. Spivak-Kroizman, T., Lemmon, M. A., Dikic, I., Ladbury, J. E., Pinchasi, D., Huang, J., Jaye, M., Crumley, G., Schleesinger, L. and J. and Lax, I. Heparin-induced oligomerization of FGF molecules is responsible for FGF receptor dimerization, activation, and cell proliferation. Cell, 79: 1015-1024, 1994.

29. Lin, X., Gan, L., Klein, W. H. and Wells, D. Expression and functional analysis of mouse EXT1, a homolog of the human multiple exostoses type 1 gene. Biochem. Biophy. Res. Commun., 248: 738-743, 1998.

30. Lantz, M., Thysell, H., Nilsson, E. and Olsson, I. On the binding of the tumor necrosis factor (TNF) to heparin and the release in vivo of the TNF-binding protein I by heparin. J. Clin. Invest., 88: 2026-2031, 1991.

31. Suzuki, A., Shao, X., Song, X.-Q., Hanaoka, T., Irie, S., Kashiwada, M., Ghassan, S., Close, L. G., Aoki, T., Fujimori, M., Ishikawa, Y., Hatori, M., Hosaka, M., Sakurada, A., Sato, M., Ohuchi, N., Satomi, S., Fukushige, S., Horii, A., and Sato, T. Identification of a 5-cM region of common allelic loss on 8p12-p21 in human breast cancer and genomic analysis of the hEXT1L/EXTR1/EXTL3 gene in this locus. Int. J. Oncol. in press

What is claimed is:

1. An isolated nucleic acid molecule encoding a human Tumor necrosis factor Receptor-Associated Factor (TRAF) protein-interacting hereditary multiple extoses (TREX) protein whiuch comprises the nucleic acid sequence set forth in SEQ ID NO:3.

2. The isolated nucleic acid molecule of claim 1, wherein the nucleic acid molecule is a DNA molecule.

3. An isolated RNA molecule encoding a human Tumor necrosis factor Receptor-Associated Factor (TRAF) proetin-interacting hereditary multiple extoses (TREX) protein which comprises the RNA sequence corresponding to that set forth in SEQ ID NO:3.

4. An isolated nucleic acid molecule wherein the nucleic acid molecule encodes a Tumor necrosis factor Receptor-Associated Factor (TRAF) protein-interacting hereditary multiple extoses (TREX) protein comprising the amino acid sequence as set forth in SEQ ID NO:4.

5. An isolated nucleic acid molecule encoding a mutant homolog of the human Tumor necrosis factor Receptor-Associated Factor (TRAF) protein-interacting hereditary multiple extoses (TREX) protein comprising the nucleic acid sequence as set forth in SEQ ID NO:3 having a genetic alteration thereof selected from the group consisting of a 9-bp insertion between nucleotide 758 and nucleotide 759, a base substitution of nucleotide 1106 from G to A, a base substitution of nucleotide 1820 from A to G, and a base substitution of nucleotide 2408 From C to T.

6. A vector comprising the nucleic acid molecule of claim 1.

7. The vector of claim 6 adapted for expression in a host cell in vitro which comprises the regulatory elements necessary for expression of the nucleic acid molecule in the host cell operatively linked to the nucleic acid molecule encoding the Tumor necrosis factor Receptor-Associated Factor (TRAF) protein-interacting hereditary multiple extoses (TREX) protein, so as to permit the expression of the TREX protein.

8. The vector of claim 7, wherein the host cell is a eukaryotic, bacterial, insect or yeast cell.

9. The vector of claim 8, wherein the eukaryotic cell is a mammalian cell.

10. The vector of claim 9, wherein the vector is a plasmid.

11. A host cell comprising the vector of claim 7.

12. The host cell of claim 11, wherein the host cell is a eukaryotic, bacterial, insect or yeast cell.

* * * * *

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 3479 base pairs
      (B) TYPE: nucleic acid
      (C) STRANDEDNESS: single -continued

```
       (D) TOPOLOGY: linear (ii) MOLECULE TYPE: DNA (genomic)

(ix) FEATURE:
       (A) NAME/KEY: CDS
       (B) LOCATION: 458..3211

(xi) SEQUENCE DESCRIPTION: SEQ ID NO: 1:

CCTGATCGTT GGTAGTGGCA TGGAGGACGG GGCTGGCATT TCAGACTGCC AGCTGTTTTT        60

ACCAGCCGCT GCATCACTTG AATAGAAGCT ATGCATATTG GCTGGCCGAC AAAGCCAAGG       120

GACAAAAGCT ATGGCCGTTA AAATGGTCCC TCTGAGTCCA GGGCTCTTTC CCTGGCTTTT       180

AGCACCATGG ATCTCTTCCT TTTCATCCCA TCAGCAATGT GGTACCTTCT TCTACTTGAT       240

GATGACAGCT GATACTTCAG ATTTGCCTGA CTAAGGTTAG AAACCTGAAT CGCTGTGAGG       300

AAGATGAAAT TTCCATTTTA CTTGGTGCCT TGTGCAGGGA GCACACTGAT CCTTCCAGAA       360

ACTTGTGTGT GAAAAGAGGT TGCGTTTTGT CAGACAGACT CATGGTTATG GCGAGCGATC       420

CGACGTGATC AGAGTGGGCA AGAGGCACAG CGAACTC ATG ACA GGC TAT ACC ATG        475
                                         Met Thr Gly Tyr Thr Met
                                         1               5

TTG CGG AAT GGG GGA GTG GGG AAC GGT GGT CAG ACC TGT ATG CTG CGC        523
Leu Arg Asn Gly Gly Val Gly Asn Gly Gly Gln Thr Cys Met Leu Arg
         10                  15                  20

TGG TCC AAT CGC ATC CGG CTG ACA TGG CTG AGT TTC ACG CTG TTC ATC        571
Trp Ser Asn Arg Ile Arg Leu Thr Trp Leu Ser Phe Thr Leu Phe Ile
     25                  30                  35

ATC CTC GTC TTC TTC CCC CTC ATT GCT CAC TAT TAC CTC ACC ACT CTG        619
Ile Leu Val Phe Phe Pro Leu Ile Ala His Tyr Tyr Leu Thr Thr Leu
 40                  45                  50

GAC GAG GCA GAC GAG GCT GGC AAG CGC ATC TTC GGC CCT CGG GCT GGC        667
Asp Glu Ala Asp Glu Ala Gly Lys Arg Ile Phe Gly Pro Arg Ala Gly
55                  60                  65                  70

AGT GAG CTC TGT GAG GTA AAG CAT GTC CTT GAT CTC TGT CGG ATT CGT        715
Ser Glu Leu Cys Glu Val Lys His Val Leu Asp Leu Cys Arg Ile Arg
             75                  80                  85

GAG TCT GTG AGC GAA GAG CTT CTA CAG CTC GAA GCC AAG CGG CAG GAG        763
Glu Ser Val Ser Glu Glu Leu Leu Gln Leu Glu Ala Lys Arg Gln Glu
         90                  95                 100

CTG AAC AGC GAG ATT GCC AAG CTG AAC CTC AAG ATT GAA GCC TGT AAG        811
Leu Asn Ser Glu Ile Ala Lys Leu Asn Leu Lys Ile Glu Ala Cys Lys
     105                 110                 115

AAG AGC ATA GAG AAT GCC AAG CAG GAC CTG CTG CAG CTC AAG AAT GTC        859
Lys Ser Ile Glu Asn Ala Lys Gln Asp Leu Leu Gln Leu Lys Asn Val
 120                 125                 130

ATT AGC CAG ACA GAG CAC TCC TAC AAG GAG CTG ATG GCC CAG AAC CAG        907
Ile Ser Gln Thr Glu His Ser Tyr Lys Glu Leu Met Ala Gln Asn Gln
135                 140                 145                 150

CCC AAA CTG TCC CTG CCC ATC CGA CTG CTC CCT GAG AAG GAC GAT GCC        955
Pro Lys Leu Ser Leu Pro Ile Arg Leu Leu Pro Glu Lys Asp Asp Ala
             155                 160                 165

GGC CTT CCA CCC CCC AAG GTC ACT CGG GGT TGC CGC CTT CAC AAC TGC       1003
Gly Leu Pro Pro Pro Lys Val Thr Arg Gly Cys Arg Leu His Asn Cys
         170                 175                 180

TTT GAT TAC TCT CGT TGT CCT CTG ACG TCT GGC TTT CCC GTC TAC GTC       1051
Phe Asp Tyr Ser Arg Cys Pro Leu Thr Ser Gly Phe Pro Val Tyr Val
     185                 190                 195

TAT GAC AGT GAC CAG TTT GCC TTT GGG AGC TAC CTG GAC CCT TTG GTC       1099
Tyr Asp Ser Asp Gln Phe Ala Phe Gly Ser Tyr Leu Asp Pro Leu Val
 200                 205                 210
```

-continued

| | | |
|---|---|---|
| AAG CAG GCT TTT CAG GCT ACA GTG AGA GCC AAC GTT TAT GTT ACA GAA<br>Lys Gln Ala Phe Gln Ala Thr Val Arg Ala Asn Val Tyr Val Thr Glu<br>215                    220                        225                        230 | 1147 |
| AAT GCG GCC ATC GCC TGC CTG TAT GTG GTG TTA GTG GGA GAA ATG CAA<br>Asn Ala Ala Ile Ala Cys Leu Tyr Val Val Leu Val Gly Glu Met Gln<br>235                    240                        245 | 1195 |
| GAG CCC ACT GTG CTG CGG CCT GCC GAC CTT GAA AAG CAG CTG TTT TCT<br>Glu Pro Thr Val Leu Arg Pro Ala Asp Leu Glu Lys Gln Leu Phe Ser<br>250                    255                        260 | 1243 |
| CTG CCA CAC TGG AGG ACA GAT GGG CAC AAC CAC GTC ATT ATC AAC CTG<br>Leu Pro His Trp Arg Thr Asp Gly His Asn His Val Ile Ile Asn Leu<br>265                    270                        275 | 1291 |
| TCC CGG AAG TCA GAC ACA CAG AAT CTA CTG TAC AAC GTC AGT ACA GGC<br>Ser Arg Lys Ser Asp Thr Gln Asn Leu Leu Tyr Asn Val Ser Thr Gly<br>280                    285                        290 | 1339 |
| CGC CAT GTG GCC CAG TCC ACC CTC TAT GCT GCC CAG TAC AGA GCT GGC<br>Arg His Val Ala Gln Ser Thr Leu Tyr Ala Ala Gln Tyr Arg Ala Gly<br>295                    300                        305                        310 | 1387 |
| TTT GAC CTG GTC GTG TCA CCC CTT GTC CAT GCT ATG TCT GAA CCC AAC<br>Phe Asp Leu Val Val Ser Pro Leu Val His Ala Met Ser Glu Pro Asn<br>315                    320                        325 | 1435 |
| TTC ATG GAA ATC CCA CCG CAG GTG CCA GTT AAG CGG AAA TAT CTC TTC<br>Phe Met Glu Ile Pro Pro Gln Val Pro Val Lys Arg Lys Tyr Leu Phe<br>330                    335                        340 | 1483 |
| ACT TTC CAG GGC GAG AAG ATC GAG TCT CTG AGA TCT AGC CTT CAG GAG<br>Thr Phe Gln Gly Glu Lys Ile Glu Ser Leu Arg Ser Ser Leu Gln Glu<br>345                    350                        355 | 1531 |
| GCC CGT TCC TTC GAG GAA GAG ATG GAG GGC GAC CCT CCG GCC GAC TAT<br>Ala Arg Ser Phe Glu Glu Glu Met Glu Gly Asp Pro Pro Ala Asp Tyr<br>360                    365                        370 | 1579 |
| GAC GAT CGC ATC ATT GCC ACC CTA AAG GCT GTA CAG GAC AGC AAG CTG<br>Asp Asp Arg Ile Ile Ala Thr Leu Lys Ala Val Gln Asp Ser Lys Leu<br>375                    380                        385                        390 | 1627 |
| GAT CAG GTG CTG GTA GAA TTC ACT TGC AAA AAC CAG CCG AAG CCT AGC<br>Asp Gln Val Leu Val Glu Phe Thr Cys Lys Asn Gln Pro Lys Pro Ser<br>395                      400                        405 | 1675 |
| CTG CCG ACT GAG TGG GCA CTG TGT GGG GAG CGG GAA GAC CGC CTG GAG<br>Leu Pro Thr Glu Trp Ala Leu Cys Gly Glu Arg Glu Asp Arg Leu Glu<br>410                    415                        420 | 1723 |
| TTA CTG AAG CTC TCC ACC TTC GCC CTC ATC ATC ACT CCC GGG GAC CCG<br>Leu Leu Lys Leu Ser Thr Phe Ala Leu Ile Ile Thr Pro Gly Asp Pro<br>425                    430                        435 | 1771 |
| CGC CTG CTC ATT TCA TCT GGG TGT GCC ACG CGG CTC TTC GAG GCC CTG<br>Arg Leu Leu Ile Ser Ser Gly Cys Ala Thr Arg Leu Phe Glu Ala Leu<br>440                    445                        450 | 1819 |
| GAG GTG GGG GCC GTG CCG GTG GTG CTC GGG GAG CAG GTG CAG CTC CCG<br>Glu Val Gly Ala Val Pro Val Val Leu Gly Glu Gln Val Gln Leu Pro<br>455                    460                        465                        470 | 1867 |
| TAC CAC GAC ATG CTG CAG TGG AAC GAG GCC GCC CTG GTG GTG CCC AAG<br>Tyr His Asp Met Leu Gln Trp Asn Glu Ala Ala Leu Val Val Pro Lys<br>475                    480                        485 | 1915 |
| CCT CGC GTC ACA GAG GTC CAC TTC CTG TTA CGA AGT CTT TCA GAC AGT<br>Pro Arg Val Thr Glu Val His Phe Leu Leu Arg Ser Leu Ser Asp Ser<br>490                    495                        500 | 1963 |
| GAT CTG TTG GCC ATG AGG CGG CAA GGC CGC TTT CTC TGG GAG ACC TAC<br>Asp Leu Leu Ala Met Arg Arg Gln Gly Arg Phe Leu Trp Glu Thr Tyr<br>505                    510                        515 | 2011 |
| TTC TCC ACC GCA GAC AGT ATT TTT AAT ACC GTG CTG GCC ATG ATT AGG<br>Phe Ser Thr Ala Asp Ser Ile Phe Asn Thr Val Leu Ala Met Ile Arg | 2059 |

-continued

```
                    520                     525                     530
ACT CGA ATT CAG ATC CCA GCT GCT CCC ATC CGG GAA GAG GTA GCG GCT        2107
Thr Arg Ile Gln Ile Pro Ala Ala Pro Ile Arg Glu Glu Val Ala Ala
535                     540                     545                     550

GAG ATC CCC CAT CGT TCA GGC AAA GCA GCT GGA ACT GAC CCC AAC ATG        2155
Glu Ile Pro His Arg Ser Gly Lys Ala Ala Gly Thr Asp Pro Asn Met
                    555                     560                     565

GCT GAC AAT GGG GAC CTG GAC CTG GGG CCG GTA GAG ACA GAA CCA CCC        2203
Ala Asp Asn Gly Asp Leu Asp Leu Gly Pro Val Glu Thr Glu Pro Pro
                570                     575                     580

TAT GCC TCA CCT AAA TAC CTC CGC AAT TTC ACT CTG ACT GTC ACA GAC        2251
Tyr Ala Ser Pro Lys Tyr Leu Arg Asn Phe Thr Leu Thr Val Thr Asp
            585                     590                     595

TGT TAC CGT GGC TGG AAC TCT GCC CCG GGA CGG TTC CAT CTT TTT CCC        2299
Cys Tyr Arg Gly Trp Asn Ser Ala Pro Gly Arg Phe His Leu Phe Pro
        600                     605                     610

CAC ACA CCC TTT GAT CCT GTG TTG CCC TCT GAG GCC AAA TTC TTG GGC        2347
His Thr Pro Phe Asp Pro Val Leu Pro Ser Glu Ala Lys Phe Leu Gly
615                     620                     625                     630

TCA GGG ACT GGA TTT CGG CCG ATC GGT GGC GGG GCT GGG GGC TCT GGC        2395
Ser Gly Thr Gly Phe Arg Pro Ile Gly Gly Gly Ala Gly Gly Ser Gly
                    635                     640                     645

AAG GAG TTC CAG GCA GCG CTC GGA GGC AAT GTC CAG CGG GAG CAG TTC        2443
Lys Glu Phe Gln Ala Ala Leu Gly Gly Asn Val Gln Arg Glu Gln Phe
                650                     655                     660

ACA GTT GTG ATG CTG ACC TAC GAG CGG GAG GAA GTG CTC ATG AAC TCC        2491
Thr Val Val Met Leu Thr Tyr Glu Arg Glu Glu Val Leu Met Asn Ser
            665                     670                     675

CTG GAG AGA CTC AAC GGC CTC CCC TAC CTG AAC AAG GTA GTG GTG GTG        2539
Leu Glu Arg Leu Asn Gly Leu Pro Tyr Leu Asn Lys Val Val Val Val
        680                     685                     690

TGG AAC TCT CCC AAG CTG CCC TCG GAG GAC CTT TTG TGG CCA GAC ATT        2587
Trp Asn Ser Pro Lys Leu Pro Ser Glu Asp Leu Leu Trp Pro Asp Ile
695                     700                     705                     710

GGT GTC CCC ATC ATG GTC GTC CGT ACT GAG AAG AAC AGT TTG AAC AAT        2635
Gly Val Pro Ile Met Val Val Arg Thr Glu Lys Asn Ser Leu Asn Asn
                    715                     720                     725

CGG TTC TTG CCC TGG AAT GAG ATT GAG ACA GAG GCC ATA CTG TCC ATC        2683
Arg Phe Leu Pro Trp Asn Glu Ile Glu Thr Glu Ala Ile Leu Ser Ile
                730                     735                     740

GAC GAT GAT GCT CAC CTC CGC CAT GAT GAA ATC ATG TTT GGG TTT TGG        2731
Asp Asp Asp Ala His Leu Arg His Asp Glu Ile Met Phe Gly Phe Trp
            745                     750                     755

GTG TGG AGA GAA GCA CGT GAT CGC ATT GTG GGT TTC CCT GGC CGG TAC        2779
Val Trp Arg Glu Ala Arg Asp Arg Ile Val Gly Phe Pro Gly Arg Tyr
        760                     765                     770

CAT GCG TGG GAC ATC CCG CAC CAG TCC TGG CTC TAC AAT TCC AAC TAC        2827
His Ala Trp Asp Ile Pro His Gln Ser Trp Leu Tyr Asn Ser Asn Tyr
775                     780                     785                     790

TCC TGT GAG CTG TCC ATG GTG CTG ACG GGC GCT GCC TTC TTT CAC AAG        2875
Ser Cys Glu Leu Ser Met Val Leu Thr Gly Ala Ala Phe Phe His Lys
                    795                     800                     805

TAT TAT GCC TAC CTG TAT TCT TAT GTG ATG CCC CAG GCC ATC CGG GAC        2923
Tyr Tyr Ala Tyr Leu Tyr Ser Tyr Val Met Pro Gln Ala Ile Arg Asp
                810                     815                     820

ATG GTG GAC GAG TAC ATC AAC TGT GAG GAT ATC GCC ATG AAC TTC CTT        2971
Met Val Asp Glu Tyr Ile Asn Cys Glu Asp Ile Ala Met Asn Phe Leu
            825                     830                     835

GTC TCC CAC ATC ACA CGG AAA CCC CCC ATC AAG GTG ACA TCA AGG TGG        3019
```

```
Val Ser His Ile Thr Arg Lys Pro Pro Ile Lys Val Thr Ser Arg Trp
    840                 845                 850

ACT TTT CGA TGC CCA GGG TGC CCT CAG GCC CTG TCC CAT GAT GAC TCT      3067
Thr Phe Arg Cys Pro Gly Cys Pro Gln Ala Leu Ser His Asp Asp Ser
855                 860                 865                 870

CAT TTT CAC GAG CGG CAC AAG TGT ATC AAC TTT TTT GTC AAG GTG TAC      3115
His Phe His Glu Arg His Lys Cys Ile Asn Phe Phe Val Lys Val Tyr
                875                 880                 885

GGC TAT ATG CCT CTC TTG TAC ACA CAG TTC AGG GTG GAC TCC GTG CTC      3163
Gly Tyr Met Pro Leu Leu Tyr Thr Gln Phe Arg Val Asp Ser Val Leu
            890                 895                 900

TTC AAG ACC CGC CTG CCC CAT GAC AAG ACC AAG TGC TTC AAG TTC ATC      3211
Phe Lys Thr Arg Leu Pro His Asp Lys Thr Lys Cys Phe Lys Phe Ile
        905                 910                 915

TAGGGCCTTG CAGTTCTGAG GAGACAATGA GCAGAGCGAG GGGGAGTCAC CCTCAAGGTT    3271

CCCAAGGTGT CGAAGGTCCT TGGGACATC TGTCGGGCAG GGCCAAGACC CTTTGCTGGG     3331

AGAGGCAGCA GGAAGAGTGG AAAGGGATAG CTGTCTTTCA TTTTGAAGTC AGCCACACTG    3391

GGCCTGGGAT CCTGGTCAGA GACTCAGGNC GTCTGCACAG GGCACTGACT GATAGCGAAC    3451

ACTGAGGACT GTTCATAAGC CCAGGACA                                      3479

(2) INFORMATION FOR SEQ ID NO: 2:

(i) SEQUENCE CHARACTERISTICS:
        (A) LENGTH: 918 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Gly Tyr Thr Met Leu Arg Asn Gly Gly Val Gly Asn Gly Gly
1               5                   10                  15

Gln Thr Cys Met Leu Arg Trp Ser Asn Arg Ile Arg Leu Thr Trp Leu
            20                  25                  30

Ser Phe Thr Leu Phe Ile Ile Leu Val Phe Phe Pro Leu Ile Ala His
        35                  40                  45

Tyr Tyr Leu Thr Thr Leu Asp Glu Ala Asp Glu Ala Gly Lys Arg Ile
    50                  55                  60

Phe Gly Pro Arg Ala Gly Ser Glu Leu Cys Glu Val Lys His Val Leu
65                  70                  75                  80

Asp Leu Cys Arg Ile Arg Glu Ser Val Ser Glu Leu Leu Gln Leu
                85                  90                  95

Glu Ala Lys Arg Gln Glu Leu Asn Ser Glu Ile Ala Lys Leu Asn Leu
                100                 105                 110

Lys Ile Glu Ala Cys Lys Lys Ser Ile Glu Asn Ala Lys Gln Asp Leu
            115                 120                 125

Leu Gln Leu Lys Asn Val Ile Ser Gln Thr Glu His Ser Tyr Lys Glu
        130                 135                 140

Leu Met Ala Gln Asn Gln Pro Lys Leu Ser Leu Pro Ile Arg Leu Leu
145                 150                 155                 160

Pro Glu Lys Asp Asp Ala Gly Leu Pro Pro Lys Val Thr Arg Gly
                165                 170                 175

Cys Arg Leu His Asn Cys Phe Asp Tyr Ser Arg Cys Pro Leu Thr Ser
            180                 185                 190

Gly Phe Pro Val Tyr Val Tyr Asp Ser Asp Gln Phe Ala Phe Gly Ser
        195                 200                 205
```

-continued

```
Tyr Leu Asp Pro Leu Val Lys Gln Ala Phe Gln Ala Thr Val Arg Ala
    210                 215                 220
Asn Val Tyr Val Thr Glu Asn Ala Ala Ile Ala Cys Leu Tyr Val Val
225                 230                 235                 240
Leu Val Gly Glu Met Gln Glu Pro Thr Val Leu Arg Pro Ala Asp Leu
                245                 250                 255
Glu Lys Gln Leu Phe Ser Leu Pro His Trp Arg Thr Asp Gly His Asn
            260                 265                 270
His Val Ile Ile Asn Leu Ser Arg Lys Ser Asp Thr Gln Asn Leu Leu
        275                 280                 285
Tyr Asn Val Ser Thr Gly Arg His Val Ala Gln Ser Thr Leu Tyr Ala
    290                 295                 300
Ala Gln Tyr Arg Ala Gly Phe Asp Leu Val Val Ser Pro Leu Val His
305                 310                 315                 320
Ala Met Ser Glu Pro Asn Phe Met Glu Ile Pro Pro Gln Val Pro Val
                325                 330                 335
Lys Arg Lys Tyr Leu Phe Thr Phe Gln Gly Glu Lys Ile Glu Ser Leu
            340                 345                 350
Arg Ser Ser Leu Gln Glu Ala Arg Ser Phe Glu Glu Glu Met Glu Gly
        355                 360                 365
Asp Pro Pro Ala Asp Tyr Asp Asp Arg Ile Ile Ala Thr Leu Lys Ala
    370                 375                 380
Val Gln Asp Ser Lys Leu Asp Gln Val Leu Val Glu Phe Thr Cys Lys
385                 390                 395                 400
Asn Gln Pro Lys Pro Ser Leu Pro Thr Glu Trp Ala Leu Cys Gly Glu
                405                 410                 415
Arg Glu Asp Arg Leu Glu Leu Leu Lys Leu Ser Thr Phe Ala Leu Ile
            420                 425                 430
Ile Thr Pro Gly Asp Pro Arg Leu Leu Ile Ser Ser Gly Cys Ala Thr
        435                 440                 445
Arg Leu Phe Glu Ala Leu Glu Val Gly Ala Val Pro Val Val Leu Gly
    450                 455                 460
Glu Gln Val Gln Leu Pro Tyr His Asp Met Leu Gln Trp Asn Glu Ala
465                 470                 475                 480
Ala Leu Val Val Pro Lys Pro Arg Val Thr Glu Val His Phe Leu Leu
                485                 490                 495
Arg Ser Leu Ser Asp Ser Asp Leu Leu Ala Met Arg Arg Gln Gly Arg
            500                 505                 510
Phe Leu Trp Glu Thr Tyr Phe Ser Thr Ala Asp Ser Ile Phe Asn Thr
        515                 520                 525
Val Leu Ala Met Ile Arg Thr Arg Ile Gln Ile Pro Ala Ala Pro Ile
    530                 535                 540
Arg Glu Glu Val Ala Ala Glu Ile Pro His Arg Ser Gly Lys Ala Ala
545                 550                 555                 560
Gly Thr Asp Pro Asn Met Ala Asp Asn Gly Asp Leu Asp Leu Gly Pro
                565                 570                 575
Val Glu Thr Glu Pro Pro Tyr Ala Ser Pro Lys Tyr Leu Arg Asn Phe
            580                 585                 590
Thr Leu Thr Val Thr Asp Cys Tyr Arg Gly Trp Asn Ser Ala Pro Gly
        595                 600                 605
Arg Phe His Leu Phe Pro His Thr Pro Phe Asp Pro Val Leu Pro Ser
    610                 615                 620
```

```
Glu Ala Lys Phe Leu Gly Ser Gly Thr Gly Phe Arg Pro Ile Gly Gly
625                 630                 635                 640

Gly Ala Gly Gly Ser Gly Lys Glu Phe Gln Ala Ala Leu Gly Gly Asn
            645                 650                 655

Val Gln Arg Glu Gln Phe Thr Val Val Met Leu Thr Tyr Glu Arg Glu
        660                 665                 670

Glu Val Leu Met Asn Ser Leu Glu Arg Leu Asn Gly Leu Pro Tyr Leu
    675                 680                 685

Asn Lys Val Val Val Trp Asn Ser Pro Lys Leu Pro Ser Glu Asp
690                 695                 700

Leu Leu Trp Pro Asp Ile Gly Val Pro Ile Met Val Val Arg Thr Glu
705                 710                 715                 720

Lys Asn Ser Leu Asn Asn Arg Phe Leu Pro Trp Asn Glu Ile Glu Thr
                725                 730                 735

Glu Ala Ile Leu Ser Ile Asp Asp Ala His Leu Arg His Asp Glu
            740                 745                 750

Ile Met Phe Gly Phe Trp Val Trp Arg Glu Ala Arg Asp Arg Ile Val
        755                 760                 765

Gly Phe Pro Gly Arg Tyr His Ala Trp Asp Ile Pro His Gln Ser Trp
    770                 775                 780

Leu Tyr Asn Ser Asn Tyr Ser Cys Glu Leu Ser Met Val Leu Thr Gly
785                 790                 795                 800

Ala Ala Phe Phe His Lys Tyr Tyr Ala Tyr Leu Tyr Ser Tyr Val Met
                805                 810                 815

Pro Gln Ala Ile Arg Asp Met Val Asp Glu Tyr Ile Asn Cys Glu Asp
            820                 825                 830

Ile Ala Met Asn Phe Leu Val Ser His Ile Thr Arg Lys Pro Pro Ile
        835                 840                 845

Lys Val Thr Ser Arg Trp Thr Phe Arg Cys Pro Gly Cys Pro Gln Ala
    850                 855                 860

Leu Ser His Asp Asp Ser His Phe His Glu Arg His Lys Cys Ile Asn
865                 870                 875                 880

Phe Phe Val Lys Val Tyr Gly Tyr Met Pro Leu Leu Tyr Thr Gln Phe
                885                 890                 895

Arg Val Asp Ser Val Leu Phe Lys Thr Arg Leu Pro His Asp Lys Thr
            900                 905                 910

Lys Cys Phe Lys Phe Ile
        915

(2) INFORMATION FOR SEQ ID NO: 3:

(i) SEQUENCE CHARACTERISTICS:
        (A) LENGTH: 6172 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 594..3350

(xi) SEQUENCE DESCRIPTION: SEQ ID NO: 3:

GGCGGGTCCC TGAGCTGGAA GCCGGAGAGC AAGCCCTGGA GGTTCACTCT TTCAAGAAGT      60

CGTGTGCTGA GGTGTAATGC TACACAAGTC AGAGGAAGGA AGGGTCCTGA AACACATGGC     120

CTGATTGTTG GCAAAGGCAT CATAAGAAGC TGGCATTTAT TTCTGTTCTA ACCTATTACT     180
```

-continued

```
GTATAACTGT GAATAGACAC TATGCATATT TGTTGGTCAG CAAAACCAAG AAACAAGAGC    240

TATGGCATTT GAAAAGTCT GTCTGATTCC AGGGTGTTTT TCCTGGGTTT CATCATCAGG     300

TACCTCCTCC CTTTCATCTC AGCAAGAATG TGGCACCTTT TATCGTTTGA TAAAGATTAA    360

GGACATGTTC TTTGGTCAAC AGCCAGAACT TAAAATCTGC TGGAATAGGG TCAGAGACCA    420

TTTCAGCTGC AGCTGAGGAA AATGAAATGT TCATTTTATT TGGTGCCTTG TCTGGGGAGC    480

ACACTAACTC TTCTGGAAAC GTGTCAGTGA ACAGAGATC GTTTTGTGGA ATAGCAACCC    540

ATGGTTATGG CGAGTGACCC GACGTGATCT GGGGGGCAGG CTGCAGAGGA CTC ATG      596
                                                                Met
```

```
ACA GGC TAT ACC ATG CTG CGG AAT GGG GGC GCG GGG AAC GGA GGT CAG     644
Thr Gly Tyr Thr Met Leu Arg Asn Gly Gly Ala Gly Asn Gly Gly Gln
920             925                 930                 935

ACC TGC ATG CTG CGC TGG TCC AAC CGC ATC CGC CTC ACG TGG CTC AGC     692
Thr Cys Met Leu Arg Trp Ser Asn Arg Ile Arg Leu Thr Trp Leu Ser
                940                 945                 950

TTC ACG CTC TTT GTC ATC CTG GTC TTC TTC CCG CTC ATC GCC CAC TAT     740
Phe Thr Leu Phe Val Ile Leu Val Phe Phe Pro Leu Ile Ala His Tyr
                    955                 960                 965

TAC CTC ACC ACT CTG GAT GAG GCT GAT GAG GCA GGC AAG CGG ATT TTT     788
Tyr Leu Thr Thr Leu Asp Glu Ala Asp Glu Ala Gly Lys Arg Ile Phe
                970                 975                 980

GGT CCC CGG GTG GGG AAC GAG CTG TGC GAG GTG AAG CAC GTG CTG GAT     836
Gly Pro Arg Val Gly Asn Glu Leu Cys Glu Val Lys His Val Leu Asp
985                 990                 995

CTG TGC CGC ATC CGG GAG TCG GTG AGT GAA GAG CTC CTG CAG CTG GAG     884
Leu Cys Arg Ile Arg Glu Ser Val Ser Glu Glu Leu Leu Gln Leu Glu
1000                1005                1010                1015

GCC AAG CGC CAA GAG CTG AAC AGC GAG ATC GCC AAG CTG AAT CTG AAG     932
Ala Lys Arg Gln Glu Leu Asn Ser Glu Ile Ala Lys Leu Asn Leu Lys
                    1020                1025                1030

ATC GAA GCC TGT AAG AAG AGC ATT GAG AAC GCC AAG CAG GAC CTG CTC     980
Ile Glu Ala Cys Lys Lys Ser Ile Glu Asn Ala Lys Gln Asp Leu Leu
                1035                1040                1045

CAG CTC AAG AAT GTC ATC AGC CAG ACC GAG CAT TCC TAC AAG GAG CTC    1028
Gln Leu Lys Asn Val Ile Ser Gln Thr Glu His Ser Tyr Lys Glu Leu
            1050                1055                1060

ATG GCC CAG AAC CAG CCC AAG CTG TCC CTG CCC ATC CGA CTG CTC CCA    1076
Met Ala Gln Asn Gln Pro Lys Leu Ser Leu Pro Ile Arg Leu Leu Pro
        1065                1070                1075

GAG AAG GAC GAT GCC GGC CTC CCT CCC CCG AAG GCC ACT CGG GGC TGC    1124
Glu Lys Asp Asp Ala Gly Leu Pro Pro Pro Lys Ala Thr Arg Gly Cys
1080                1085                1090                1095

CGG CTA CAC AAC TGC TTT GAT TAT TCT CGT TGC CCT CTC ACC TCT GGC    1172
Arg Leu His Asn Cys Phe Asp Tyr Ser Arg Cys Pro Leu Thr Ser Gly
                    1100                1105                1110

TTC CCG GTC TAC GTC TAT GAC AGT GAC CAG TTT GTC TTT GGC AGC TAC    1220
Phe Pro Val Tyr Val Tyr Asp Ser Asp Gln Phe Val Phe Gly Ser Tyr
                1115                1120                1125

CTG GAT CCC TTG GTC AAG CAG GCT TTT CAG GCG ACA GCA CGA GCT AAC    1268
Leu Asp Pro Leu Val Lys Gln Ala Phe Gln Ala Thr Ala Arg Ala Asn
            1130                1135                1140

GTT TAT GTT ACA GAA AAT GCA GAC ATC GCC TGC CTT TAC GTG ATA CTA    1316
Val Tyr Val Thr Glu Asn Ala Asp Ile Ala Cys Leu Tyr Val Ile Leu
        1145                1150                1155

GTG GGA GAG ATG CAG GAG CCC GTG GTG CTG CGG CCT GCT GAG CTG GAG    1364
Val Gly Glu Met Gln Glu Pro Val Val Leu Arg Pro Ala Glu Leu Glu
1160                1165                1170                1175
```

-continued

| | |
|---|---|
| AAG CAG TTG TAT TCC CTG CCA CAC TGG CGG ACG GAT GGA CAC AAC CAT<br>Lys Gln Leu Tyr Ser Leu Pro His Trp Arg Thr Asp Gly His Asn His<br>                      1180                            1185                          1190 | 1412 |
| GTC ATC ATC AAT CTG TCA CGT AAG TCA GAT ACA CAG AAC CTT CTC TAT<br>Val Ile Ile Asn Leu Ser Arg Lys Ser Asp Thr Gln Asn Leu Leu Tyr<br>                1195                       1200                         1205 | 1460 |
| AAC GTC AGT ACT GGC CGT GCC ATG GTG GCC CAG TCC ACC TTC TAC ACT<br>Asn Val Ser Thr Gly Arg Ala Met Val Ala Gln Ser Thr Phe Tyr Thr<br>         1210                     1215                     1220 | 1508 |
| GTC CAG TAC AGA CCT GGC TTT GAC TTG GTC GTA TCA CCG CTG GTC CAT<br>Val Gln Tyr Arg Pro Gly Phe Asp Leu Val Val Ser Pro Leu Val His<br>    1225                     1230                     1235 | 1556 |
| GCC ATG TCT GAG CCC AAC TTC ATG GAA ATC CCA CCA CAG GTG CCG GTG<br>Ala Met Ser Glu Pro Asn Phe Met Glu Ile Pro Pro Gln Val Pro Val<br>1240                   1245                     1250                     1255 | 1604 |
| AAG CGG AAA TAT CTC TTC ACC TTC CAG GGC GAG AAG ATT GAG TCT CTG<br>Lys Arg Lys Tyr Leu Phe Thr Phe Gln Gly Glu Lys Ile Glu Ser Leu<br>                1260                     1265                     1270 | 1652 |
| AGG TCT AGC CTT CAG GAG GCC CGC TCC TTC GAA GAG GAA ATG GAG GGC<br>Arg Ser Ser Leu Gln Glu Ala Arg Ser Phe Glu Glu Glu Met Glu Gly<br>        1275                     1280                     1285 | 1700 |
| GAC CCT CCC GCC GAC TAC GAT GAC CGG ATC ATT GCC ACC CTG AAG GCG<br>Asp Pro Pro Ala Asp Tyr Asp Asp Arg Ile Ile Ala Thr Leu Lys Ala<br>            1290                     1295                     1300 | 1748 |
| GTG CAG GAC AGC AAG CTG GAT CAG GTC CTG GTG GAA TTC ACC TGC AAA<br>Val Gln Asp Ser Lys Leu Asp Gln Val Leu Val Glu Phe Thr Cys Lys<br>    1305                     1310                     1315 | 1796 |
| AAC CAG CCC AAA CCC AGC CTG CCG ACT GAG TGG GCA CTG TGT GGA GAG<br>Asn Gln Pro Lys Pro Ser Leu Pro Thr Glu Trp Ala Leu Cys Gly Glu<br>1320                   1325                     1330                     1335 | 1844 |
| CGG GAG GAC CGC TTG GAA TTG CTG AAG CTC TCC ACC TTC GCC CTC ATC<br>Arg Glu Asp Arg Leu Glu Leu Leu Lys Leu Ser Thr Phe Ala Leu Ile<br>                1340                     1345                     1350 | 1892 |
| ATT ACC CCC GGG GAC CCT CGC TTG GTT ATT TCC TCT GGG TGT GCA ACA<br>Ile Thr Pro Gly Asp Pro Arg Leu Val Ile Ser Ser Gly Cys Ala Thr<br>        1355                     1360                     1365 | 1940 |
| CGG CTC TTC GAA GCC CTG GAA GTC GGT GCC GTC CCG GTG GTG CTG GGG<br>Arg Leu Phe Glu Ala Leu Glu Val Gly Ala Val Pro Val Val Leu Gly<br>            1370                     1375                     1380 | 1988 |
| GAG CAG GTC CAG CTT CCC TAC CAG GAC ATG CTG CAG TGG AAC GAG GCG<br>Glu Gln Val Gln Leu Pro Tyr Gln Asp Met Leu Gln Trp Asn Glu Ala<br>    1385                     1390                     1395 | 2036 |
| GCC CTG GTG GTG CCA AAG CCT CGT GTT ACC GAG GTT CAT TTC CTG CTC<br>Ala Leu Val Val Pro Lys Pro Arg Val Thr Glu Val His Phe Leu Leu<br>1400                   1405                     1410                     1415 | 2084 |
| AGA AGC CTC TCC GAT AGT GAC CTC CTG GCT ATG AGG CGG CAA GGC CGC<br>Arg Ser Leu Ser Asp Ser Asp Leu Leu Ala Met Arg Arg Gln Gly Arg<br>                1420                     1425                     1430 | 2132 |
| TTT CTC TGG GAG ACT TAC TTC TCC ACT GCT GAC AGT ATT TTT AAT ACC<br>Phe Leu Trp Glu Thr Tyr Phe Ser Thr Ala Asp Ser Ile Phe Asn Thr<br>            1435                     1440                     1445 | 2180 |
| GTG CTG GCT ATG ATT AGG ACT CGC ATC CAG ATC CCA GCC GCT CCC ATC<br>Val Leu Ala Met Ile Arg Thr Arg Ile Gln Ile Pro Ala Ala Pro Ile<br>        1450                     1455                     1460 | 2228 |
| CGG GAA GAG GCG GCA GCT GAG ATC CCC CAC CGT TCA GGC AAG GCG GCT<br>Arg Glu Glu Ala Ala Ala Glu Ile Pro His Arg Ser Gly Lys Ala Ala<br>    1465                     1470                     1475 | 2276 |
| GGA ACT GAC CCC AAC ATG GCT GAC AAC GGG GAC CTG GAC CTG GGG CCA<br>Gly Thr Asp Pro Asn Met Ala Asp Asn Gly Asp Leu Asp Leu Gly Pro | 2324 |

-continued

```
1480              1485              1490              1495

GTG GAG ACG GAG CCG CCC TAC GCC TCA CCC AGA TAC CTC CGC AAT TTC      2372
Val Glu Thr Glu Pro Pro Tyr Ala Ser Pro Arg Tyr Leu Arg Asn Phe
                1500              1505              1510

ACT CTG ACT GTC ACT GAC TTT TAC CGC AGC TGG AAC TGT GCT CCA GGG      2420
Thr Leu Thr Val Thr Asp Phe Tyr Arg Ser Trp Asn Cys Ala Pro Gly
                1515              1520              1525

CCT TTC CAT CTT TTC CCC CAC ACT CCC TTT GAC CCT GTG TTG CCC TCA      2468
Pro Phe His Leu Phe Pro His Thr Pro Phe Asp Pro Val Leu Pro Ser
                1530              1535              1540

GAG GCC AAA TTC TTG GGC TCA GGG ACT GGC TTT CGG CCT ATT GGT GGT      2516
Glu Ala Lys Phe Leu Gly Ser Gly Thr Gly Phe Arg Pro Ile Gly Gly
            1545              1550              1555

GGA GCT GGG GGT TCT GGC AAG GAA TTT CAG GCA GCG CTT GGA GGC AAT      2564
Gly Ala Gly Gly Ser Gly Lys Glu Phe Gln Ala Ala Leu Gly Gly Asn
1560              1565              1570              1575

GTT CCC CGA GAG CAG TTC ACG GTG GTG ATG TTG ACT TAT GAG CGG GAG      2612
Val Pro Arg Glu Gln Phe Thr Val Val Met Leu Thr Tyr Glu Arg Glu
                1580              1585              1590

GAA GTG CTT ATG AAC TCT TTA GAG AGG CTG AAT GGC CTC CCT TAC CTG      2660
Glu Val Leu Met Asn Ser Leu Glu Arg Leu Asn Gly Leu Pro Tyr Leu
                1595              1600              1605

AAC AAG GTC GTG GTG GTG TGG AAT TCT CCC AAG CTG CCA TCA GAG GAC      2708
Asn Lys Val Val Val Val Trp Asn Ser Pro Lys Leu Pro Ser Glu Asp
            1610              1615              1620

CTT CTG TGG CCT GAC ATT GGC GTT CCC ATC ATG GTG GTC CGT ACT GAG      2756
Leu Leu Trp Pro Asp Ile Gly Val Pro Ile Met Val Val Arg Thr Glu
            1625              1630              1635

AAG AAC AGT TTG AAC AAC CGA TTC TTA CCC TGG AAT GAA ATT GAG ACA      2804
Lys Asn Ser Leu Asn Asn Arg Phe Leu Pro Trp Asn Glu Ile Glu Thr
1640              1645              1650              1655

GAG GCC ATC CTG TCC ATT GAT GAC GAT GCT CAC CTC CGC CAT GAC GAA      2852
Glu Ala Ile Leu Ser Ile Asp Asp Asp Ala His Leu Arg His Asp Glu
                1660              1665              1670

ATC ATG TTT GGG TTC CGG GTG TGG AGA GAA GCT CGG GAC CGC ATC GTG      2900
Ile Met Phe Gly Phe Arg Val Trp Arg Glu Ala Arg Asp Arg Ile Val
                1675              1680              1685

GGC TTC CCT GGC CGT TAC CAC GCA TGG GAC ATC CCC CAT CAG TCC TGG      2948
Gly Phe Pro Gly Arg Tyr His Ala Trp Asp Ile Pro His Gln Ser Trp
                1690              1695              1700

CTC TAC AAC TCC AAC TAC TCC TGT GAG CTG TCC ATG GTG CTG ACA GGT      2996
Leu Tyr Asn Ser Asn Tyr Ser Cys Glu Leu Ser Met Val Leu Thr Gly
            1705              1710              1715

GCT GCC TTC TTT CAC AAG TAT TAT GCC TAC CTG TAT TCT TAT GTG ATG      3044
Ala Ala Phe Phe His Lys Tyr Tyr Ala Tyr Leu Tyr Ser Tyr Val Met
1720              1725              1730              1735

CCC CAG GCC ATC CGG GAC ATG GTG GAT GAA TAC ATC AAC TGT GAG GAC      3092
Pro Gln Ala Ile Arg Asp Met Val Asp Glu Tyr Ile Asn Cys Glu Asp
                1740              1745              1750

ATT GCC ATG AAC TTC CTT GTC TCC CAC ATC ACT CGG AAG CCC CCC ATC      3140
Ile Ala Met Asn Phe Leu Val Ser His Ile Thr Arg Lys Pro Pro Ile
                1755              1760              1765

AAG GTG ACC TCA CGG TGG ACA TTC CGA TGC CCA GGA TGC CCT CAG GCC      3188
Lys Val Thr Ser Arg Trp Thr Phe Arg Cys Pro Gly Cys Pro Gln Ala
                1770              1775              1780

CTG TCT CAT GAT GAC TCC CAC TTC CAC GAG CGG CAC AAG TGC ATC AAC      3236
Leu Ser His Asp Asp Ser His Phe His Glu Arg His Lys Cys Ile Asn
                1785              1790              1795

TTC TTC GTG AAG GTG TAC GGC TAC ATG CCC CTC CTG TAC ACG CAG TTC      3284
```

```
                                                              -continued
Phe Phe Val Lys Val Tyr Gly Tyr Met Pro Leu Leu Tyr Thr Gln Phe
1800            1805                1810                1815

AGG GTG GAT TCT GTG CTC TTC AAG ACA CGC CTG CCC CAT GAC AAG ACC        3332
Arg Val Asp Ser Val Leu Phe Lys Thr Arg Leu Pro His Asp Lys Thr
                1820                1825                1830

AAG TGC TTC AAG TTC ATC TAGGGGCAGC GCACGGTCTG GGGAAGAGGA               3380
Lys Cys Phe Lys Phe Ile
                1835

TGAGCAGAGG GAGGAAGATG GCTCCCAAGG TTCCTAGGCA TTGCAGGACC TTGGGCACAT      3440

CTGCTGGTGG GTGGCCCAGA GCCTCTGCTG GAAGGGGCAG CAGGAGGAGT GGAAGGAAAC      3500

CGCTGCCTTT ATCTTGAAGT CAGCCACACT GGGCCTGGAG CCCTGGGCGG AGTCCCCGGG      3560

GTTCCCCACA CAGGGCACTG ACTGATAGCT TACACTGAGG ACTGTGGCGA CTCTGCAGAG      3620

TCACTCACAC CGTTCGTACG CCCAGGACAG CTGGTTCGTG GTTTTTACAT TCAATAACAA      3680

CTATTATGAT TATTTAAAAA GAGAAAGTTT CAGATTTGCC ATTCAAGGCT TATTTATATA      3740

TATGTGTGTG TATATAAATA CATGCACACA CTTGCATACA TATATATTTT TGGCTGGGGG      3800

AGTGTGAGTT TTGCCTTTCT AAGGGAGGGA CCGCGCAGGC TCCTTTGTTC TGTATTCTGG      3860

CGGAGATGGG TCCTGGCCTT GTGTCACTGG CTTATCCTTA AAGATCATCT CCCATCCTCC      3920

CCAGCGCCAT CTGTGTGCAG CAACCAGAAA GGGATGAACT TGGCCCTCTT GCGGGCCTGG      3980

ACAAGGTCTC TTCCTTACCC TTTCTGTTGC CAGTCAGCAA CCTGTAACTC ACATTCTCTT      4040

CCCAGTGAAT CCCTGGGAGC GCCTGACCCT GGTGGGCTGT TCAGCTTCCT GCTGCTGGGG      4100

CCAGCGATTT TTGAGGATTT ATCTTTAGGC CAGGCTTGCC TCCGTACTTA TCCCTGCTCT      4160

CCCATTTCTC TCTTGTTTGA GAGAGAATGA GGAAGCAAAG AGTGAGAAAG AATAGGGGCT      4220

GAAGACGCCA CTCCCAGATG GCTCTTTCTA TCCTGCTCTT CTGTTGAAAC ACACGTGCTG      4280

TGGGCCTCAG GCGTTTCTGA AGTGCTCTTT CTTGGATTGG ACAGGAGATC AGCAGCGTGC      4340

ACATCTGCTG TGGTCTGAAG TGGTTTGCAG GTCAGCCTCC TCTCCCTAGT GTAGAGCAAG      4400

CCAGTGTCCT TCGAGGAACC CACCCGGCTG GCCGGGAAGT TTTACAGCAA GGCGCCTGCC      4460

TTGGGATAAT TCCTTGGTGA AATTCACCTT CCCCCCGCCT CTGTCTGGAG CCCCATCCTG      4520

TGTTATCTGT GGTTTTTGGA CCCCTAATGT CAGCTTGGCT GTAGGACTCC CCGAGGTTTG      4580

GTATGTGCTA GAACAATGGG AGGCTGTGAT TTGCTGTGTA AGCTCACATC CAGCCTTGGA      4640

ATCTAACGGG CATTCACAAC CCGAGTTACC ACTTTCCACT CCCTGCTTAG GATTCTGTTC      4700

CCTGGGCTGA AACTGAAATA AGCTAATTTT TTGGGTCACG GTGGCAGTAG GGAACCTAG      4760

GAGGGTGTGA GTGGCATTTG TCAGGGATTT AGCCCATGAC GTGTTTCTTG AACCCTACTT      4820

TCTGGAAGTG GAGTTGACTC TGGAAGTTTT CTAGCAACTG AACAAAAGCT CAGGTTTGTC      4880

CTGGTCATGC ACATGCCTTA AGCCAGTTCC GTCTTCCCTA GACCTTGGCA TCCTGTGCTT      4940

CTATTTCTTG GAATACGTTC TCCTCTGACC TGCCTGTACC ACGTGGGTCC TCTTCAAGTA      5000

CTGTTTTGAA GCTGGGCTCT TTTGTGTAGC TCCCACCCAC CTGTAGGGCT AGCTCGGCTT      5060

AAGGGAACTC TCCCCATTGG CAAACCGGAC CCGGCCGCCG CCAGGACTGT GTTTCCAAAG      5120

GTTCCCCGCC CCCAACCCCA GCATCAGCCT GTAGCTCCCC TGCTGAGGCA GTGTGGTTAT      5180

GTCCCAGCA GTGGGGGTCA GACGCCCTTC CTCAGAACTT TCTAGTTGCC CTCTACCTGA      5240

CTCCTGACTT GTATTCCTTT TAGCAGTAGC CTTCTTCCCT CGGGGAGCCA AGAGTGTGG      5300

TGTGTGGCGC TATATTGTGG CTGCTATTTC ATCTGGTTTC TTTTAATGTG AGGAACTCAC      5360

ATACTGACTT CAGTGGGACT CGGTGAGCCG GGGCCGTCTG TGTGGTGGGA CCCCCTTTAG      5420
```

-continued

```
CGGGACTCAG TGAGCTGGGG CCGTCTGTGT GGTGGAGCCA GGGCCTCTCC CTTTAGTGGA    5480

GCCAGGTTGT CGGGCCCCGA ATGTCACTGG TGGATCTAAG AAGGGCTGAG TGGTCTGACA    5540

CCAAAACATG CCGCAGGGAG GGCTGTGGTG CCGGTGCTTC CAACAAGGAC AGCCCTCCTT    5600

GACCCTGAAA GGAACACTGG CTTGAAGGAC TGCAGACAGG CTCTGAGGGG CACGCCCTCC    5660

TCAGCGAGAG GCAGCAAGGT GGCCACAGTG TCACTGGTCA GGTGCTTCTC ACCACGGGAA    5720

AGCCGCCGAC CTGTGACTCG CTTGAGATGG GAAAGCGGCG CCACAGACCC CGGGTCTCCT    5780

TGGCTGTCTG TGGGCCGCCC CTGGCCACCT TGTCCTGGCT CGCAGGGTGC AGGAGCGCCT    5840

CGTTCTCTGG GTGGCCGGCT TGCTGCTCCG GTTTGGGCTG TCTTACCATA ACACCGTCCC    5900

AGGGCTCTGC AGGCCACTGT GAGCGCTGGC TCCCTGGGCA GTGCTCCTCC GTGTGGACTG    5960

TGCCTCAGGC CAGGGCTCAC CAGCTGGGGT CCTGTCCGGA AGGATGGGAT CTTTCTGGGA    6020

GCTGCGCCGG ACAGAGTGGG GAGCTCCTAG TTTGTGGGGG AAGCTTTGA TATCCATGCC    6080

ACGTCCATCC ACCCCACCCC TTTTCGTCAC GAGCACAATG GTCTTACATT GGATTTTTGT    6140

AAAAAAATAA AATAAATGG AGACTTTAAC TC                                    6172
```

(2) INFORMATION FOR SEQ ID NO: 4:

(i) SEQUENCE CHARACTERISTICS:
        (A) LENGTH: 919 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Thr Gly Tyr Thr Met Leu Arg Asn Gly Gly Ala Gly Asn Gly Gly
1               5                   10                  15

Gln Thr Cys Met Leu Arg Trp Ser Asn Arg Ile Arg Leu Thr Trp Leu
            20                  25                  30

Ser Phe Thr Leu Phe Val Ile Leu Val Phe Phe Pro Leu Ile Ala His
        35                  40                  45

Tyr Tyr Leu Thr Thr Leu Asp Glu Ala Asp Glu Ala Gly Lys Arg Ile
    50                  55                  60

Phe Gly Pro Arg Val Gly Asn Glu Leu Cys Glu Val Lys His Val Leu
65                  70                  75                  80

Asp Leu Cys Arg Ile Arg Glu Ser Val Ser Glu Leu Leu Gln Leu
                85                  90                  95

Glu Ala Lys Arg Gln Glu Leu Asn Ser Glu Ile Ala Lys Leu Asn Leu
            100                 105                 110

Lys Ile Glu Ala Cys Lys Lys Ser Ile Glu Asn Ala Lys Gln Asp Leu
        115                 120                 125

Leu Gln Leu Lys Asn Val Ile Ser Gln Thr Glu His Ser Tyr Lys Glu
    130                 135                 140

Leu Met Ala Gln Asn Gln Pro Lys Leu Ser Leu Pro Ile Arg Leu Leu
145                 150                 155                 160

Pro Glu Lys Asp Asp Ala Gly Leu Pro Pro Lys Ala Thr Arg Gly
            165                 170                 175

Cys Arg Leu His Asn Cys Phe Asp Tyr Ser Arg Cys Pro Leu Thr Ser
        180                 185                 190

Gly Phe Pro Val Tyr Val Tyr Asp Ser Asp Gln Phe Val Phe Gly Ser
    195                 200                 205

Tyr Leu Asp Pro Leu Val Lys Gln Ala Phe Gln Ala Thr Ala Arg Ala
    210                 215                 220
```

-continued

```
Asn Val Tyr Val Thr Glu Asn Ala Asp Ile Ala Cys Leu Tyr Val Ile
225                 230                 235                 240

Leu Val Gly Glu Met Gln Glu Pro Val Val Leu Arg Pro Ala Glu Leu
            245                 250                 255

Glu Lys Gln Leu Tyr Ser Leu Pro His Trp Arg Thr Asp Gly His Asn
        260                 265                 270

His Val Ile Ile Asn Leu Ser Arg Lys Ser Asp Thr Gln Asn Leu Leu
    275                 280                 285

Tyr Asn Val Ser Thr Gly Arg Ala Met Val Ala Gln Ser Thr Phe Tyr
290                 295                 300

Thr Val Gln Tyr Arg Pro Gly Phe Asp Leu Val Val Ser Pro Leu Val
305                 310                 315                 320

His Ala Met Ser Glu Pro Asn Phe Met Glu Ile Pro Pro Gln Val Pro
                325                 330                 335

Val Lys Arg Lys Tyr Leu Phe Thr Phe Gln Gly Glu Lys Ile Glu Ser
            340                 345                 350

Leu Arg Ser Ser Leu Gln Glu Ala Arg Ser Phe Glu Glu Glu Met Glu
        355                 360                 365

Gly Asp Pro Pro Ala Asp Tyr Asp Asp Arg Ile Ile Ala Thr Leu Lys
    370                 375                 380

Ala Val Gln Asp Ser Lys Leu Asp Gln Val Leu Val Glu Phe Thr Cys
385                 390                 395                 400

Lys Asn Gln Pro Lys Pro Ser Leu Pro Thr Glu Trp Ala Leu Cys Gly
                405                 410                 415

Glu Arg Glu Asp Arg Leu Glu Leu Leu Lys Leu Ser Thr Phe Ala Leu
            420                 425                 430

Ile Ile Thr Pro Gly Asp Pro Arg Leu Val Ile Ser Ser Gly Cys Ala
        435                 440                 445

Thr Arg Leu Phe Glu Ala Leu Glu Val Gly Ala Val Pro Val Val Leu
    450                 455                 460

Gly Glu Gln Val Gln Leu Pro Tyr Gln Asp Met Leu Gln Trp Asn Glu
465                 470                 475                 480

Ala Ala Leu Val Val Pro Lys Pro Arg Val Thr Glu Val His Phe Leu
                485                 490                 495

Leu Arg Ser Leu Ser Asp Ser Asp Leu Leu Ala Met Arg Arg Gln Gly
            500                 505                 510

Arg Phe Leu Trp Glu Thr Tyr Phe Ser Thr Ala Asp Ser Ile Phe Asn
        515                 520                 525

Thr Val Leu Ala Met Ile Arg Thr Arg Ile Gln Ile Pro Ala Ala Pro
    530                 535                 540

Ile Arg Glu Glu Ala Ala Ala Glu Ile Pro His Arg Ser Gly Lys Ala
545                 550                 555                 560

Ala Gly Thr Asp Pro Asn Met Ala Asp Asn Gly Asp Leu Asp Leu Gly
                565                 570                 575

Pro Val Glu Thr Glu Pro Pro Tyr Ala Ser Pro Arg Tyr Leu Arg Asn
            580                 585                 590

Phe Thr Leu Thr Val Thr Asp Phe Tyr Arg Ser Trp Asn Cys Ala Pro
        595                 600                 605

Gly Pro Phe His Leu Phe Pro His Thr Pro Phe Asp Pro Val Leu Pro
    610                 615                 620

Ser Glu Ala Lys Phe Leu Gly Ser Gly Thr Gly Phe Arg Pro Ile Gly
625                 630                 635                 640
```

```
Gly Gly Ala Gly Gly Ser Gly Lys Glu Phe Gln Ala Ala Leu Gly Gly
                645                 650                 655

Asn Val Pro Arg Glu Gln Phe Thr Val Val Met Leu Thr Tyr Glu Arg
            660                 665                 670

Glu Glu Val Leu Met Asn Ser Leu Glu Arg Leu Asn Gly Leu Pro Tyr
        675                 680                 685

Leu Asn Lys Val Val Val Trp Asn Ser Pro Lys Leu Pro Ser Glu
690                 695                 700

Asp Leu Leu Trp Pro Asp Ile Gly Val Pro Ile Met Val Val Arg Thr
705                 710                 715                 720

Glu Lys Asn Ser Leu Asn Asn Arg Phe Leu Pro Trp Asn Glu Ile Glu
                725                 730                 735

Thr Glu Ala Ile Leu Ser Ile Asp Asp Ala His Leu Arg His Asp
            740                 745                 750

Glu Ile Met Phe Gly Phe Arg Val Trp Arg Glu Ala Arg Asp Arg Ile
        755                 760                 765

Val Gly Phe Pro Gly Arg Tyr His Ala Trp Asp Ile Pro His Gln Ser
770                 775                 780

Trp Leu Tyr Asn Ser Asn Tyr Ser Cys Glu Leu Ser Met Val Leu Thr
785                 790                 795                 800

Gly Ala Ala Phe Phe His Lys Tyr Tyr Ala Tyr Leu Tyr Ser Tyr Val
                805                 810                 815

Met Pro Gln Ala Ile Arg Asp Met Val Asp Glu Tyr Ile Asn Cys Glu
            820                 825                 830

Asp Ile Ala Met Asn Phe Leu Val Ser His Ile Thr Arg Lys Pro Pro
        835                 840                 845

Ile Lys Val Thr Ser Arg Trp Thr Phe Arg Cys Pro Gly Cys Pro Gln
850                 855                 860

Ala Leu Ser His Asp Asp Ser His Phe His Glu Arg His Lys Cys Ile
865                 870                 875                 880

Asn Phe Phe Val Lys Val Tyr Gly Tyr Met Pro Leu Leu Tyr Thr Gln
                885                 890                 895

Phe Arg Val Asp Ser Val Leu Phe Lys Thr Arg Leu Pro His Asp Lys
            900                 905                 910

Thr Lys Cys Phe Lys Phe Ile
        915

(2) INFORMATION FOR SEQ ID NO: 5:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Leu Cys Gly Glu Arg Glu Asp Arg Leu Glu Leu Leu Lys Leu Ser Thr
1               5                   10                  15

Phe Ala Leu Ile Ile Thr Pro Gly Asp Pro Arg Leu Val Ile Ser Ser
                20                  25                  30

Gly Cys Ala Thr Arg Leu Phe Glu Ala Leu Glu Val Gly Ala Val Pro
            35                  40                  45

Val Val Leu Gly Glu Gln Val Gln Leu Pro Tyr Gln Asp Met Leu Gln
        50                  55                  60
```

```
Trp Asn Glu Ala Ala Leu Val Val Pro Lys Pro Arg Val Thr Glu Val
 65                  70                  75                  80

His Phe Leu Leu Arg Ser Leu Ser Asp Ser Asp Leu Leu Ala Met Arg
                 85                  90                  95

Arg Gln Gly Arg Phe Leu Trp Glu Thr Tyr Phe Pro Thr Ala Asp Ser
            100                 105                 110

Ile Phe Asn Thr Val Leu Ala Met Ile Arg Thr Arg Ile
        115                 120                 125

(2) INFORMATION FOR SEQ ID NO: 6:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Arg Cys His Lys His Gln Val Phe Asp Tyr Pro Gln Val Leu Gln Glu
  1               5                  10                  15

Ala Thr Phe Cys Val Val Leu Arg Gly Ala Arg Leu Gly Gln Ala Val
                 20                  25                  30

Leu Ser Asp Val Leu Gln Ala Gly Cys Val Pro Val Val Ile Ala Asp
             35                  40                  45

Ser Tyr Ile Leu Pro Phe Ser Glu Val Leu Asp Trp Lys Arg Ala Ser
 50                  55                  60

Val Val Val Pro Glu Glu Lys Met Ser Asp Val Tyr Ser Ile Leu Gln
 65                  70                  75                  80

Ser Ile Pro Gln Arg Gln Ile Glu Glu Met Gln Arg Gln Ala Arg Trp
                 85                  90                  95

Phe Trp Glu Ala Tyr Phe Gln Ser Ile Lys Ala Ile Ala Leu Ala Thr
            100                 105                 110

Leu Gln Ile Ile Asn Asp Arg Ile
        115                 120

(2) INFORMATION FOR SEQ ID NO: 7:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Arg Cys Asp Arg Asp Asn Thr Glu Tyr Glu Lys Tyr Asp Tyr Arg Glu
  1               5                  10                  15

Met Leu His Asn Ala Thr Phe Cys Leu Val Pro Arg Gly Arg Arg Leu
                 20                  25                  30

Gly Ser Phe Arg Phe Leu Glu Ala Leu Gln Ala Ala Cys Val Pro Val
            35                  40                  45

Met Leu Ser Asn Gly Trp Glu Leu Pro Phe Ser Glu Val Ile Asn Trp
 50                  55                  60

Asn Gln Ala Ala Val Ile Gly Asp Glu Arg Leu Leu Leu Gln Ile Pro
 65                  70                  75                  80

Ser Thr Ile Arg Ser Ile His Gln Asp Lys Ile Leu Ala Leu Arg Gln
                 85                  90                  95
```

Gln Thr Gln Phe Leu Trp Glu Ala Tyr Phe Ser Ser Val Glu Lys Ile
            100                 105                 110

Val Leu Thr Thr Leu Glu Ile Ile Gln Asp Arg Ile
            115                 120

(2) INFORMATION FOR SEQ ID NO: 8:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Arg Cys Glu Gln Asp Pro Gly Pro Gly Gln Thr Gln Arg Gln Glu Thr
1                   5                   10                  15

Leu Pro Asn Ala Thr Phe Cys Leu Ile Ser Gly His Arg Pro Glu Ala
            20                  25                  30

Ala Ser Arg Phe Leu Gln Ala Leu Gln Ala Gly Cys Ile Pro Val Leu
            35                  40                  45

Leu Ser Pro Arg Trp Glu Leu Pro Phe Ser Glu Val Ile Asp Trp Thr
        50                  55                  60

Lys Ala Ala Ile Val Ala Asp Glu Arg Leu Pro Leu Gln Val Leu Ala
65                  70                  75                  80

Ala Leu Gln Glu Met Ser Pro Ala Arg Val Leu Ala Leu Arg Gln Gln
            85                  90                  95

Thr Gln Phe Leu Trp Asp Ala Tyr Phe Ser Ser Val Glu Lys Val Ile
            100                 105                 110

His Thr Thr Leu Glu Val Ile Gln Asp Arg Ile
            115                 120

(2) INFORMATION FOR SEQ ID NO: 9:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Lys Cys Ser Gln Glu Asn Cys Ser Leu Glu Arg Arg Gln Leu Ile
1                   5                   10                  15

Gly Ser Ser Thr Phe Cys Phe Leu Pro Ser Glu Met Phe Phe Gln
            20                  25                  30

Asp Phe Leu Ser Ser Leu Gln Leu Gly Cys Ile Pro Ile Leu Leu Ser
            35                  40                  45

Asn Ser Gln Leu Leu Pro Phe Gln Asp Leu Ile Asp Trp Arg Arg Ala
        50                  55                  60

Thr Tyr Arg Leu Pro Leu Ala Arg Leu Pro Glu Ala His Phe Ile Val
65                  70                  75                  80

Gln Ser Phe Glu Ile Ser Asp Ile Ile Glu Met Arg Arg Val Gly Arg
            85                  90                  95

Leu Phe Tyr Glu Thr Tyr Leu Ala Asp Arg His Leu Leu Ala Arg Ser
            100                 105                 110

Leu Leu Ala Ala Leu Arg Tyr Lys Leu

```
               115                 120

(2) INFORMATION FOR SEQ ID NO: 10:

(i) SEQUENCE CHARACTERISTICS:
        (A) LENGTH: 262 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Val Pro Arg Glu Gln Phe Thr Val Val Met Leu Thr Tyr Glu Arg Glu
1               5                   10                  15

Glu Val Leu Met Asn Ser Leu Glu Arg Leu Asn Gly Leu Pro Tyr Leu
            20                  25                  30

Asn Lys Val Val Val Trp Asn Ser Pro Lys Leu Pro Ser Glu Asp
        35                  40                  45

Leu Leu Trp Pro Asp Ile Gly Val Pro Ile Met Val Val Arg Thr Glu
50                  55                  60

Lys Asn Ser Leu Asn Asn Arg Phe Leu Pro Trp Asn Glu Ile Glu Thr
65                  70                  75                  80

Glu Ala Ile Leu Ser Ile Asp Asp Ala His Leu Arg His Asp Glu
                85                  90                  95

Ile Met Phe Gly Phe Arg Val Trp Arg Glu Ala Arg Asp Arg Ile Val
                100                 105                 110

Gly Phe Pro Gly Arg Tyr His Ala Trp Asp Ile Pro His Gln Ser Trp
            115                 120                 125

Leu Tyr Asn Ser Asn Tyr Ser Cys Glu Leu Ser Met Val Leu Thr Gly
    130                 135                 140

Ala Ala Phe Phe His Lys Tyr Tyr Ala Tyr Leu Tyr Ser Tyr Val Met
145                 150                 155                 160

Pro Gln Ala Ile Arg Asp Met Val Asp Glu Tyr Ile Asn Cys Glu Asp
                165                 170                 175

Ile Ala Met Asn Phe Leu Val Ser His Ile Thr Arg Lys Pro Pro Ile
                180                 185                 190

Lys Val Thr Ser Arg Trp Thr Phe Arg Cys Pro Gly Cys Pro Gln Ala
            195                 200                 205

Leu Ser His Asp Asp Ser His Phe His Glu Arg His Lys Cys Ile Asn
    210                 215                 220

Phe Phe Val Lys Val Tyr Gly Tyr Met Pro Leu Leu Tyr Thr Gln Phe
225                 230                 235                 240

Arg Val Asp Ser Val Leu Phe Lys Thr Arg Leu Pro His Asp Lys Thr
                245                 250                 255

Lys Cys Phe Lys Phe Ile
            260

(2) INFORMATION FOR SEQ ID NO: 11:

(i) SEQUENCE CHARACTERISTICS:
        (A) LENGTH: 269 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:
```

```
Pro Gln Ser Gln Gly Phe Thr Gln Ile Val Leu Thr Tyr Asp Arg Val
1               5                   10                  15

Glu Ser Leu Phe Arg Val Ile Thr Glu Val Ser Lys Val Pro Ser Leu
                20                  25                  30

Ser Lys Leu Leu Val Val Trp Asn Asn Gln Asn Lys Asn Pro Pro Glu
            35                  40                  45

Asp Ser Leu Trp Pro Lys Ile Arg Val Pro Leu Lys Val Val Arg Thr
        50                  55                  60

Ala Glu Asn Lys Leu Ser Asn Arg Phe Phe Pro Tyr Asp Glu Ile Glu
65                  70                  75                  80

Thr Glu Ala Val Leu Ala Ile Asp Asp Ile Ile Met Leu Thr Ser
                85                  90                  95

Asp Glu Leu Gln Phe Gly Tyr Glu Val Trp Arg Glu Phe Pro Asp Arg
                100                 105                 110

Leu Val Gly Tyr Pro Gly Arg Leu His Leu Trp Asp His Glu Ala Met
            115                 120                 125

Asn Lys Trp Lys Tyr Glu Ser Glu Trp Thr Asn Glu Val Ser Met Val
            130                 135                 140

Leu Thr Gly Ala Ala Phe Tyr His Lys Tyr Phe Asn Tyr Leu Tyr Thr
145                 150                 155                 160

Lys Met Pro Gly Asp Ile Lys Asn Trp Val Asp Ala His Met Asn Cys
                165                 170                 175

Tyr Glu Asp Ile Ala Met Asn Phe Leu Val Ala Asn Val Thr Gly Lys
                180                 185                 190

Ala Val Ile Lys Val Thr Pro Arg Lys Lys Phe Lys Cys Pro Glu Cys
        195                 200                 205

Thr Ala Ile Asp Gly Leu Ser Leu Asp Gln Thr His Met Val Glu Arg
    210                 215                 220

Ser Glu Cys Ile Asn Lys Phe Ala Ser Val Phe Gly Thr Met Pro Leu
225                 230                 235                 240

Lys Val Val Glu His Arg Ala Asp Pro Val Leu Tyr Lys Asp Asp Phe
                245                 250                 255

Pro Glu Lys Leu Lys Ser Phe Pro Asn Ile Gly Ser Leu
                260                 265

(2) INFORMATION FOR SEQ ID NO: 12:

(i) SEQUENCE CHARACTERISTICS:
        (A) LENGTH: 270 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Pro Pro Ser Lys Phe Thr Ala Val Ile His Ala Val Thr Pro Leu Val
1               5                   10                  15

Ser Gln Ser Gln Pro Val Leu Lys Leu Leu Val Ala Ala Lys Ser
                20                  25                  30

Gln Tyr Cys Ala Gln Ile Ile Val Leu Trp Asn Cys Asp Lys Pro Leu
            35                  40                  45

Pro Ala Lys His Arg Trp Pro Ala Thr Ala Val Pro Val Val Val Ile
        50                  55                  60

Glu Gly Glu Ser Lys Val Met Ser Ser Arg Phe Leu Pro Tyr Asp Asn
65                  70                  75                  80
```

```
Ile Ile Thr Asp Ala Val Leu Ser Leu Asp Glu Asp Thr Val Leu Ser
                85                  90                  95

Thr Thr Glu Val Asp Phe Ala Phe Thr Val Trp Gln Ser Phe Pro Glu
            100                 105                 110

Arg Ile Val Gly Tyr Pro Ala Arg Ser His Phe Trp Asp Asn Ser Lys
        115                 120                 125

Glu Arg Trp Gly Tyr Thr Ser Lys Trp Thr Asn Asp Tyr Ser Met Val
    130                 135                 140

Leu Thr Gly Ala Ala Ile Tyr His Lys Tyr Tyr His Tyr Leu Tyr Ser
145                 150                 155                 160

His Tyr Leu Pro Ala Ser Leu Lys Asn Met Val Asp Gln Leu Ala Asn
                165                 170                 175

Cys Glu Asp Ile Leu Met Asn Phe Leu Val Ser Ala Val Thr Lys Leu
            180                 185                 190

Pro Pro Ile Lys Val Thr Gln Lys Lys Gln Tyr Lys Glu Thr Met Met
        195                 200                 205

Gly Gln Thr Ser Arg Ala Ser Arg Trp Ala Asp Pro Asp His Phe Ala
    210                 215                 220

Gln Arg Gln Ser Cys Met Asn Thr Phe Ala Ser Trp Phe Gly Tyr Met
225                 230                 235                 240

Pro Leu Ile His Ser Gln Met Arg Leu Asp Pro Val Leu Lys Asp Gln
                245                 250                 255

Val Ser Ile Leu Arg Lys Lys Tyr Arg Asp Ile Glu Arg Leu
                260                 265                 270

(2) INFORMATION FOR SEQ ID NO: 13:

(i) SEQUENCE CHARACTERISTICS:
        (A) LENGTH: 262 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Pro Glu Gly Arg Phe Ser Ala Leu Ile Trp Val Gly Pro Pro Gly Gln
1               5                   10                  15

Pro Pro Leu Lys Leu Ile Gln Ala Val Ala Gly Ser Gln His Cys Ala
            20                  25                  30

Gln Ile Leu Val Leu Trp Ser Asn Glu Arg Pro Leu Pro Ser Arg Trp
        35                  40                  45

Pro Glu Thr Ala Val Pro Leu Thr Val Ile Asp Gly His Arg Lys Val
    50                  55                  60

Ser Asp Arg Phe Tyr Pro Tyr Ser Thr Ile Arg Thr Asp Ala Ile Leu
65                  70                  75                  80

Ser Leu Asp Ala Arg Ser Ser Leu Ser Thr Ser Glu Val Asp Phe Ala
                85                  90                  95

Phe Leu Val Trp Gln Ser Phe Pro Glu Arg Met Val Gly Phe Leu Thr
            100                 105                 110

Ser Ser His Phe Trp Asp Glu Ala His Gly Gly Trp Gly Tyr Thr Ala
        115                 120                 125

Glu Arg Thr Asn Glu Phe Ser Met Val Leu Thr Ala Ala Phe Tyr
    130                 135                 140

His Arg Tyr Tyr His Thr Leu Phe Thr His Ser Leu Pro Lys Ala Leu
145                 150                 155                 160
```

```
Arg Thr Leu Ala Asp Glu Ala Pro Thr Cys Val Asp Val Leu Met Asn
                165                 170                 175

Phe Ile Val Ala Ala Val Thr Lys Leu Pro Ile Lys Val Pro Tyr
            180                 185                 190

Gly Lys Gln Arg Gln Glu Ala Ala Pro Leu Ala Pro Gly Gly Pro Gly
            195                 200                 205

Pro Arg Pro Lys Pro Pro Ala Pro Ala Pro Asp Cys Ile Asn Gln Ile
210                 215                 220

Ala Ala Ala Phe Gly His Met Pro Leu Leu Ser Ser Arg Leu Arg Leu
225                 230                 235                 240

Asp Pro Val Leu Phe Lys Asp Pro Val Ser Val Gln Arg Lys Lys Tyr
                245                 250                 255

Arg Ser Leu Glu Lys Pro
            260
```

(2) INFORMATION FOR SEQ ID NO: 14:

(i) SEQUENCE CHARACTERISTICS:
        (A) LENGTH: 270 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

```
Ser Thr Met Asp Ser Phe Thr Leu Ile Met Gln Thr Tyr Asn Arg Thr
1               5                   10                  15

Asp Leu Leu Leu Lys Leu Leu Asn His Tyr Gln Ala Val Pro Asn Leu
                20                  25                  30

His Lys Val Ile Val Val Trp Asn Asn Ile Gly Glu Lys Ala Pro Asp
            35                  40                  45

Glu Leu Trp Asn Ser Leu Gly Pro His Pro Ile Pro Val Ile Phe Lys
50                  55                  60

Gln Gln Thr Ala Asn Arg Met Arg Asn Arg Leu Gln Val Phe Pro Glu
65                  70                  75                  80

Leu Glu Thr Asn Ala Val Leu Met Val Asp Asp Thr Leu Ile Ser
                85                  90                  95

Thr Pro Asp Leu Val Phe Ala Phe Ser Val Trp Gln Gln Phe Pro Asp
                100                 105                 110

Gln Ile Val Gly Phe Val Pro Arg Lys His Val Ser Thr Ser Ser Gly
            115                 120                 125

Ile Tyr Ser Tyr Gly Ser Phe Glu Met Gln Ala Pro Gly Ser Gly Asn
130                 135                 140

Gly Asp Gln Tyr Ser Met Val Leu Ile Gly Ala Ser Phe Phe Asn Ser
145                 150                 155                 160

Lys Tyr Leu Glu Leu Phe Gln Arg Gln Pro Ala Val His Ala Leu
            165                 170                 175

Ile Asp Asp Thr Gln Asn Cys Asp Asp Ile Ala Met Asn Phe Ile Ile
                180                 185                 190

Ala Lys His Ile Gly Lys Thr Ser Gly Ile Phe Val Lys Pro Val Asn
            195                 200                 205

Met Asp Asn Leu Glu Lys Glu Thr Asn Ser Gly Tyr Ser Gly Met Trp
                210                 215                 220

His Arg Ala Glu His Ala Leu Gln Arg Ser Tyr Cys Ile Asn Lys Leu
225                 230                 235                 240
```

```
Val Asn Ile Tyr Asp Ser Met Pro Leu Arg Tyr Ser Asn Ile Met Ile
            245                 250                 255

Ser Gln Phe Gly Phe Pro Tyr Ala Asn Tyr Lys Arg Lys Ile
            260                 265                 270
```

(2) INFORMATION FOR SEQ ID NO: 15:

(i) SEQUENCE CHARACTERISTICS:
        (A) LENGTH: 259 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

```
Arg Gln Arg Glu Gln Phe Thr Val Val Leu Leu Thr Tyr Glu Arg Asp
1               5                   10                  15

Ala Val Leu Thr Gly Ala Leu Glu Arg Leu His Gln Leu Pro Tyr Leu
            20                  25                  30

Asn Lys Ile Ile Val Val Trp Asn Asn Val Asn Arg Asp Pro Pro Asp
            35                  40                  45

Ser Trp Pro Ser Leu His Ile Pro Val Glu Phe Ile Arg Val Ala Glu
50                  55                  60

Asn Asn Leu Asn Asn Arg Phe Val Pro Trp Asp Arg Ile Glu Thr Glu
65                  70                  75                  80

Ala Val Leu Ser Leu Asp Asp Asp Ile Asp Leu Met Gln Gln Glu Ile
            85                  90                  95

Ile Leu Ala Phe Arg Val Trp Arg Glu Asn Arg Asp Arg Ile Val Gly
            100                 105                 110

Phe Pro Ala Arg His His Ala Arg Tyr Gly Asp Ser Met Phe Tyr Asn
            115                 120                 125

Ser Asn His Thr Cys Gln Met Ser Met Ile Leu Thr Gly Ala Ala Phe
            130                 135                 140

Ile His Lys Asn Tyr Leu Thr Ala Tyr Thr Tyr Glu Met Pro Ala Glu
145                 150                 155                 160

Ile Arg Glu His Val Asn Ser Ile Lys Asn Cys Glu Asp Ile Ala Met
                165                 170                 175

Asn Tyr Leu Val Ser His Leu Thr Arg Lys Pro Pro Ile Lys Thr Thr
            180                 185                 190

Ser Arg Trp Thr Leu Lys Cys Pro Thr Cys Thr Glu Ser Leu Tyr Lys
            195                 200                 205

Glu Gly Thr His Phe Glu Lys Arg His Glu Cys Met Arg Leu Phe Thr
            210                 215                 220

Lys Ile Tyr Gly Tyr Asn Pro Leu Lys Phe Ser Gln Phe Arg Ala Asp
225                 230                 235                 240

Ser Ile Leu Phe Lys Thr Arg Leu Pro Gln Asn His Gln Lys Cys Phe
            245                 250                 255

Lys Tyr Val
```

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

TTATGGCGAG TGACCCGACG TG                                              22

(2) INFORMATION FOR SEQ ID NO: 17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

TTGCTAAAGT GAAGGAAGTT GG                                              22

(2) INFORMATION FOR SEQ ID NO: 18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

ACCCGACGTG ATCTGG                                                     16

(2) INFORMATION FOR SEQ ID NO: 19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

AAGAGCTCCT GCAGCTGG                                                   18

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

TTCTCGTTGC CCTCTCAC                                                   18

(2) INFORMATION FOR SEQ ID NO: 21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

ATCATCAATC TGTCACG                                                    17

(2) INFORMATION FOR SEQ ID NO: 22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ACTACGATGA CCGGATC                                   17

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

TTCCCTACCA GGACATGC                                  18

(2) INFORMATION FOR SEQ ID NO: 24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

AACATGGCTG ACAACG                                    16

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

TATTGGTGGT GGAGCTGG                                  18

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

AATCCAGCCA TGGTCTCCTT GG                              22

(2) INFORMATION FOR SEQ ID NO: 27:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 27:

AGTCGATGCC ATTATTACCA GC                                              22

(2) INFORMATION FOR SEQ ID NO: 28:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 28:

TTCCTTCCTC ATCACAG                                                    17

(2) INFORMATION FOR SEQ ID NO: 29:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 29:

AGGTCTGTGT ATGCACTTGT G                                               21

(2) INFORMATION FOR SEQ ID NO: 30:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 30:

AGTCGATGCC ATTATTACCA GC                                              22

(2) INFORMATION FOR SEQ ID NO: 31:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 31:

TTCAAGGGTG TGGAGAG                                                    17

(2) INFORMATION FOR SEQ ID NO: 32:

(i) SEQUENCE CHARACTERISTICS:
       (A) LENGTH: 22 base pairs
       (B) TYPE: nucleic acid
       (C) STRANDEDNESS: single (D) TOPOLOGY: linear (ii) MOLECULE TYPE: DNA (genomic)

(xi) SEQUENCE DESCRIPTION: SEQ ID NO: 32:

TTGGCTGAAA GCCAACAACC TG                                             22

(2) INFORMATION FOR SEQ ID NO: 33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 33:

AACATGCACG CATCCACAGC                                                20

(2) INFORMATION FOR SEQ ID NO: 34:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 34:

TTGTAACACA GCATGTGG                                                  18

(2) INFORMATION FOR SEQ ID NO: 35:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 35:

GGTTCTGTCA GTATTAGCTG GG                                             22

(2) INFORMATION FOR SEQ ID NO: 36:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 36:

TTCCTCCCTC TGCTCATCCT C                                              21

(2) INFORMATION FOR SEQ ID NO: 37:

(i) SEQUENCE CHARACTERISTICS:
            (A) LENGTH: 17 base pairs
            (B) TYPE: nucleic acid
            (C) STRANDEDNESS: single
            (D) TOPOLOGY: linear

```
       (ii) MOLECULE TYPE: DNA (genomic)

(xi) SEQUENCE DESCRIPTION: SEQ ID NO: 37:

TTCCCACTCT GTCTCTC                                                    17
```